(12) United States Patent
Thrippleton

(10) Patent No.: US 8,993,239 B2
(45) Date of Patent: Mar. 31, 2015

(54) NUCLEIC ACID BEACONS FOR FLUORESCENT IN-SITU HYBRIDIZATION AND CHIP TECHNOLOGY

(71) Applicant: miacom Diagnostics GmbH, Duesseldorf (DE)

(72) Inventor: Ian Thrippleton, Duesseldorf (DE)

(73) Assignee: miacom Diagnostics GmbH, Duesseldorf (DE)

( * ) Notice: Subject to any disclaimer, the term of this patent is extended or adjusted under 35 U.S.C. 154(b) by 0 days.

(21) Appl. No.: 14/198,613

(22) Filed: Mar. 6, 2014

(65) Prior Publication Data

US 2014/0255926 A1    Sep. 11, 2014

Related U.S. Application Data

(63) Continuation of application No. 12/445,202, filed as application No. PCT/EP2007/008811 on Oct. 10, 2007, now abandoned.

(30) Foreign Application Priority Data

Oct. 10, 2006  (EP) ..................................... 06021267

(51) Int. Cl.
    *C12Q 1/68*  (2006.01)
(52) U.S. Cl.
    CPC ................................... *C12Q 1/6841* (2013.01)
    USPC ........................................ 435/6.11; 536/24.3
(58) Field of Classification Search
    None
    See application file for complete search history.

(56) References Cited

U.S. PATENT DOCUMENTS

2003/0232377 A1    12/2003  Thomas
2009/0029867 A1     1/2009  Reed et al.

FOREIGN PATENT DOCUMENTS

WO    2004020625 A1    3/2004
WO    2004081520       9/2004
WO    2006060561 A2    6/2006

OTHER PUBLICATIONS

Xi et al., "Use of DNA and Peptide Nucleic Acid Molecular Beacons for Detection and Quantification of rRNA in Solution and in Whole Cells," in Applied and Environmental Microbiology, vol. 69, No. 9, Sep. 2003, pp. 5673-5678.
G. Bonnet et al., "Thermodynamic basis of the enhanced specificity of structured DNA probes", Proceedings of the National Academy of Sciences of USA, National Academy of Science, vol. 96, No. 11, May 25, 1999, pp. 6171-6176.
Natalia E. Broude, "Stem-loop oligonucleotides: a robust tool for molecular biology and biotechnology", Trends in Biotechnology, Elsevier Publications, vol. 20, No. 6, Jun. 1, 2002, pp. 249-256.
Julia F. Hopkins, et al., "Molecular Beacons as Probes of RNA Unfolding under Native Conditions", Nucleic Acids Research, vol. 33, No. 18 (2005), pp. 5763-5770.
Xiang-Hong Peng, "Real-time Detection of Gene Expression in Cancer Cells Using Molecular Beacon Imaging: New Strategies for Cancer Research", Cancer Research, American Association for Cancer Research, vol. 65, No. 5, Mar. 1, 2005, pp. 1909-1917.
Weihong Tan, "Molecular beacons: a novel DNA probe for nucleic acid and protein studies", Chemistry European Journal, vol. 6, No. 7, Apr. 3, 2000; pp. 1107-1111.
Andrew Tsourkas et al.: "Hybridization kinetics and thermodynamics of molecular beacons" Nucleic Acids Research, Oxford University Press, vol. 31, No. 4, Feb. 15, 2003, pp. 1319-1330.

*Primary Examiner* — Jim Ketter
(74) *Attorney, Agent, or Firm* — Joyce von Natzmer; Agris & von Natzmer, LLP

(57) ABSTRACT

The present invention relates to beacons for fluorescent in-situ hybridization and chip technology.

16 Claims, No Drawings

SEQUENCE LISTING

<160> NUMBER OF SEQ ID NOS: 358

<210> SEQ ID NO 1
<211> LENGTH: 40
<212> TYPE: DNA
<213> ORGANISM: Artificial Sequence
<220> FEATURE:
<223> OTHER INFORMATION: Beacon, target: Acinetobacter

<400> SEQUENCE: 1
tgccggatta ccatcctctc ccatactcta aatcccggca     40

<210> SEQ ID NO 2
<211> LENGTH: 21
<212> TYPE: DNA
<213> ORGANISM: Artificial Sequence
<220> FEATURE:
<223> OTHER INFORMATION: Probe, target: Acinetobacter

<400> SEQUENCE: 2
accatcctct cccatactct a     21

<210> SEQ ID NO 3
<211> LENGTH: 21

```
<212> TYPE: DNA
<213> ORGANIZM: Unknown
<220> FEATURE:
<223> OTHER INFORMATION: Target of SEQ ID NO: 1 and 2, organism:
      Acinetobacter

<400> SEQUENCE: 3
tagagtatgg gagaggatgg t                                              21

<210> SEQ ID NO 4
<211> LENGTH: 30
<212> TYPE: DNA
<213> ORGANISM: Artificial Sequence
<220> FEATURE:
<223> OTHER INFORMATION: Beacon, target: Acinetobacter baumannii

<400> SEQUENCE: 4
gcgcgtccgg tagcaagcta ccttccgcgc                                     30

<210> SEQ ID NO 5
<211> LENGTH: 20
<212> TYPE: DNA
<213> ORGANISM: Artificial Sequence
<220> FEATURE:
<223> OTHER INFORMATION: Probe, target: Acinetobacter baumannii

<400> SEQUENCE: 5
tccggtagca agctaccttc                                                20

<210> SEQ ID NO 6
<211> LENGTH: 20
<212> TYPE: DNA
<213> ORGANISM: Acinetobacter baumannii

<400> SEQUENCE: 6
gaaggtagct tgctaccgga                                                20

<210> SEQ ID NO 7
<211> LENGTH: 41
<212> TYPE: DNA
<213> ORGANISM: Artificial Sequence
<220> FEATURE:
<223> OTHER INFORMATION: Beacon, target: Aspergillus flavus

<400> SEQUENCE: 7
ccgccggcgt acagagttcg tggtgtctcc tcgcccagcg g                        41

<210> SEQ ID NO 8
<211> LENGTH: 20
<212> TYPE: DNA
<213> ORGANISM: Artificial Sequence
<220> FEATURE:
<223> OTHER INFORMATION: Probe, target: Aspergillus flavus

<400> SEQUENCE: 8
acagagttcg tggtgtctcc                                                20

<210> SEQ ID NO 9
<211> LENGTH: 20
<212> TYPE: DNA
<213> ORGANISM: Aspergillus flavus

<400> SEQUENCE: 9
ggagacacca cgaactctgt                                                20
```

```
<210> SEQ ID NO 10
<211> LENGTH: 23
<212> TYPE: DNA
<213> ORGANISM: Artificial sequence
<220> FEATURE:
<223> OTHER INFORMATION: Beacon, target: Aspergillus fumigatus

<400> SEQUENCE: 10
cgtcgcctac agagcaggtg acg                                           23

<210> SEQ ID NO 11
<211> LENGTH: 18
<212> TYPE: DNA
<213> ORGANISM: Artificial sequence
<220> FEATURE:
<223> OTHER INFORMATION: Probe, target: Aspergillus fumigatus

<400> SEQUENCE: 11
gcctacagag caggtgac                                                 18

<210> SEQ ID NO 12
<211> LENGTH: 18
<212> TYPE: DNA
<213> ORGANISM: Aspergillus fumigatus

<400> SEQUENCE: 12
gtcacctgct ctgtaggc                                                 18

<210> SEQ ID NO 13
<211> LENGTH: 32
<212> TYPE: DNA
<213> ORGANISM: Artificial sequence
<220> FEATURE:
<223> OTHER INFORMATION: Beacon, target: Aspergillus niger

<400> SEQUENCE: 13
ctctgaactg attgcattca atcaactcag ag                                 32

<210> SEQ ID NO 14
<211> LENGTH: 25
<212> TYPE: DNA
<213> ORGANISM: Artificial sequence
<220> FEATURE:
<223> OTHER INFORMATION: Probe, target: Aspergillus niger

<400> SEQUENCE: 14
actgattgca ttcaatcaac tcaga                                         25

<210> SEQ ID NO 15
<211> LENGTH: 25
<212> TYPE: DNA
<213> ORGANISM: Aspergillus niger

<400> SEQUENCE: 15
tctgagttga ttgaatgcaa tcagt                                         25

<210> SEQ ID NO 16
<211> LENGTH: 36
<212> TYPE: DNA
<213> ORGANISM: Artificial sequence
<220> FEATURE:
<223> OTHER INFORMATION: Beacon, target: Aspergillus terreus

<400> SEQUENCE: 16
tccgtctgat tgcaaagaat cacactcaga gacgga                             36
```

```
<210> SEQ ID NO 17
<211> LENGTH: 24
<212> TYPE: DNA
<213> ORGANISM: Artificial sequence
<220> FEATURE:
<223> OTHER INFORMATION: Probe, target: Aspergillus terreus

<400> SEQUENCE: 17
tgattgcaaa gaatcacact caga                                           24

<210> SEQ ID NO 18
<211> LENGTH: 24
<212> TYPE: DNA
<213> ORGANISM: Aspergillus terreus

<400> SEQUENCE: 18
tctgagtgtg attctttgca atca                                           24

<210> SEQ ID NO 19
<211> LENGTH: 41
<212> TYPE: DNA
<213> ORGANISM: Artificial sequence
<220> FEATURE:
<223> OTHER INFORMATION: Beacon, targets: Bacteroides/Prevotella

<400> SEQUENCE: 19
gccgccggca tccaatgtgg gggaccttct agcccagcgg c                        41

<210> SEQ ID NO 20
<211> LENGTH: 18
<212> TYPE: DNA
<213> ORGANISM: Artificial sequence
<220> FEATURE:
<223> OTHER INFORMATION: Probe, targets: Bacteroides/Prevotella

<400> SEQUENCE: 20
ccaatgtggg ggaccttc                                                  18

<210> SEQ ID NO 21
<211> LENGTH: 18
<212> TYPE: DNA
<213> ORGANISM: Unknown
<220> FEATURE:
<223> OTHER INFORMATION: Target of SEQ ID NO: 19 and 20, organisms:
      Bacteroides/Prevotella

<400> SEQUENCE: 21
gaaggtcccc cacattgg                                                  18

<210> SEQ ID NO 22
<211> LENGTH: 39
<212> TYPE: DNA
<213> ORGANISM: Artificial sequence
<220> FEATURE:
<223> OTHER INFORMATION: Beacon, target: Borrelia burgdorferi

<400> SEQUENCE: 22
tgccggattc atgcttaaga cgcactgcca atcccggca                           39

<210> SEQ ID NO 23
<211> LENGTH: 20
<212> TYPE: DNA
<213> ORGANISM: Artificial sequence
<220> FEATURE:
<223> OTHER INFORMATION: Probe, target: Borrelia burgdorferi
```

```
<400> SEQUENCE: 23
catgcttaag acgcactgcc                                              20

<210> SEQ ID NO 24
<211> LENGTH: 20
<212> TYPE: DNA
<213> ORGANISM: Borrelia burgdorferi

<400> SEQUENCE: 24
ggcagtgcgt cttaagcatg                                              20

<210> SEQ ID NO 25
<211> LENGTH: 40
<212> TYPE: DNA
<213> ORGANISM: Artificial sequence
<220> FEATURE:
<223> OTHER INFORMATION: Beacon, target: Bordetella pertussis

<400> SEQUENCE: 25
tgccggattc agcactctgc aaagacgaaa aatcccggca                        40

<210> SEQ ID NO 26
<211> LENGTH: 21
<212> TYPE: DNA
<213> ORGANISM: Artificial sequence
<220> FEATURE:
<223> OTHER INFORMATION: Probe, target: Bordetella pertussis

<400> SEQUENCE: 26
cagcactctg caaagacgaa a                                            21

<210> SEQ ID NO 27
<211> LENGTH: 21
<212> TYPE: DNA
<213> ORGANISM: Bordetella pertussis

<400> SEQUENCE: 27
tttcgtcttt gcagagtgct g                                            21

<210> SEQ ID NO 28
<211> LENGTH: 39
<212> TYPE: DNA
<213> ORGANISM: Artificial sequence
<220> FEATURE:
<223> OTHER INFORMATION: Beacon, target: Burkholderia cepacia complex
      (Option I)

<400> SEQUENCE: 28
accgctcttt ctttccggac aaaagtgctt tgagcggct                         39

<210> SEQ ID NO 29
<211> LENGTH: 24
<212> TYPE: DNA
<213> ORGANISM: Artificial sequence
<220> FEATURE:
<223> OTHER INFORMATION: Probe, target: Bukholderia cepacia complex
      (Option I)

<400> SEQUENCE: 29
tttctttccg gacaaaagtg cttt                                         24

<210> SEQ ID NO 30
<211> LENGTH: 24
<212> TYPE: DNA
<213> ORGANISM: Unknown
```

```
<220> FEATURE:
<223> OTHER INFORMATION: Target of SEQ ID NO: 28 and 29, organism:
      Burkholderia cepacia complex (Option I)

<400> SEQUENCE: 30
aaagcacttt tgtccggaaa gaaa                                            24

<210> SEQ ID NO 31
<211> LENGTH: 36
<212> TYPE: DNA
<213> ORGANISM: Artificial sequence
<220> FEATURE:
<223> OTHER INFORMATION: Beacon, target: Burkholderia cepacia complex
      (Option II = two beacons)

<400> SEQUENCE: 31
cgccttcaga accaaggatt tctttccggg aaggcg                               36

<210> SEQ ID NO 32
<211> LENGTH: 22
<212> TYPE: DNA
<213> ORGANISM: Artificial sequence
<220> FEATURE:
<223> OTHER INFORMATION: Probe, target: Burkholderia cepacia complex
      (Option II = two beacons)

<400> SEQUENCE: 32
agaaccaagg atttctttcc gg                                              22

<210> SEQ ID NO 33
<211> LENGTH: 22
<212> TYPE: DNA
<213> ORGANISM: Unknown
<220> FEATURE:
<223> OTHER INFORMATION: Target of SEQ ID NO: 31 and 32, organism:
      Burkholderia cepacia complex (Option II = two beacons)

<400> SEQUENCE: 33
ccggaaagaa atccttggtt ct                                              22

<210> SEQ ID NO 34
<211> LENGTH: 33
<212> TYPE: DNA
<213> ORGANISM: Artificial sequence
<220> FEATURE:
<223> OTHER INFORMATION: Beacon, target: Burkholderia cepacia complex
      (Option II = two beacons)

<400> SEQUENCE: 34
acgcaagagc caaggttttc tttccgcttg cgt                                  33

<210> SEQ ID NO 35
<211> LENGTH: 21
<212> TYPE: DNA
<213> ORGANISM: Artificial sequence
<220> FEATURE:
<223> OTHER INFORMATION: Probe, target: Burkholderia cepacia complex
      (Option II = two beacons)

<400> SEQUENCE: 35
agagccaagg ttttctttcc g                                               21

<210> SEQ ID NO 36
<211> LENGTH: 21
<212> TYPE: DNA
<213> ORGANISM: Unknown
<220> FEATURE:
```

<223> OTHER INFORMATION: Target of SEQ ID NO: 34 and 35, organism:
      Burkholderia cepacia complex (Option II = two beacons)

<400> SEQUENCE: 36
cggaaagaaa accttggctc t                                              21

<210> SEQ ID NO 37
<211> LENGTH: 28
<212> TYPE: DNA
<213> ORGANISM: Artificial sequence
<220> FEATURE:
<223> OTHER INFORMATION: Beacon, target: Burkholderia cepacia

<400> SEQUENCE: 37
acgctcgtca tcccccggcc atgagcgt                                       28

<210> SEQ ID NO 38
<211> LENGTH: 16
<212> TYPE: DNA
<213> ORGANISM: Artificial sequence
<220> FEATURE:
<223> OTHER INFORMATION: Probe, target: Burkholderia cepacia

<400> SEQUENCE: 38
gtcatccccc ggccat                                                    16

<210> SEQ ID NO 39
<211> LENGTH: 16
<212> TYPE: DNA
<213> ORGANISM: Burkholderia cepacia

<400> SEQUENCE: 39
atggccgggg gatgac                                                    16

<210> SEQ ID NO 40
<211> LENGTH: 29
<212> TYPE: DNA
<213> ORGANISM: Artificial sequence
<220> FEATURE:
<223> OTHER INFORMATION: Beacon, targets: Burkholderia pyrrocinia /
      stabilis / ambifaria

<400> SEQUENCE: 40
cgctccgtca tcccccggct ataggagcg                                      29

<210> SEQ ID NO 41
<211> LENGTH: 18
<212> TYPE: DNA
<213> ORGANISM: Artificial sequence
<220> FEATURE:
<223> OTHER INFORMATION: Probe, targets: Burkholderia pyrrocinia /
      stabilis / ambifaria

<400> SEQUENCE: 41
cgtcatcccc ggctata                                                   18

<210> SEQ ID NO 42
<211> LENGTH: 18
<212> TYPE: DNA
<213> ORGANISM: Unknown
<220> FEATURE:
<223> OTHER INFORMATION: Target of SEQ ID NO: 40 and 41, organisms:
      Burkholderia pyrrocinia / stabilis / ambifaria

<400> SEQUENCE: 42
tatagccggg ggatgacg                                                  18

<210> SEQ ID NO 43
<211> LENGTH: 29
<212> TYPE: DNA
<213> ORGANISM: Artificial sequence
<220> FEATURE:
<223> OTHER INFORMATION: Beacon, target: Burkholderia dolosa / anthina

<400> SEQUENCE: 43
ccgctcgtca tcccccggct gtagagcgg                                        29

<210> SEQ ID NO 44
<211> LENGTH: 17
<212> TYPE: DNA
<213> ORGANISM: Artificial sequence
<220> FEATURE:
<223> OTHER INFORMATION: Probe, target: Burkholderia dolosa / anthina

<400> SEQUENCE: 44
gtcatccccc ggctgta                                                     17

<210> SEQ ID NO 45
<211> LENGTH: 17
<212> TYPE: DNA
<213> ORGANISM: Unknown
<220> FEATURE:
<223> OTHER INFORMATION: Target of SEQ ID NO: 43 and 44, organism:
      Burkholderia dolosa / anthina

<400> SEQUENCE: 45
tacagccggg ggatgac                                                     17

<210> SEQ ID NO 46
<211> LENGTH: 41
<212> TYPE: DNA
<213> ORGANISM: Artificial sequence
<220> FEATURE:
<223> OTHER INFORMATION: Beacon, target: Burkholderia multivorans

<400> SEQUENCE: 46
gccgccggcg tcgtcatccc ccgatcgtat cgcccagcgg c                          41

<210> SEQ ID NO 47
<211> LENGTH: 18
<212> TYPE: DNA
<213> ORGANISM: Artificial sequence
<220> FEATURE:
<223> OTHER INFORMATION: Probe, target: Burkholderia multivorans

<400> SEQUENCE: 47
cgtcatcccc cgatcgta                                                    18

<210> SEQ ID NO 48
<211> LENGTH: 18
<212> TYPE: DNA
<213> ORGANISM: Burkholderia multivorans

<400> SEQUENCE: 48
tacgatcggg ggatgacg                                                    18

<210> SEQ ID NO 49
<211> LENGTH: 41
<212> TYPE: DNA
<213> ORGANISM: Artificial sequence
<220> FEATURE:
<223> OTHER INFORMATION: Beacon, target: Burkholderia cenocepacia /

-continued vietnamiensis

<400> SEQUENCE: 49
gccgccggcg tcgtcatccc ccgactgtat cgcccagcgg c                    41

<210> SEQ ID NO 50
<211> LENGTH: 18
<212> TYPE: DNA
<213> ORGANISM: Artificial sequence
<220> FEATURE:
<223> OTHER INFORMATION: Probe, target: Burkholderia cenocepacia /
      vietnamiensis

<400> SEQUENCE: 50
cgtcatcccc cgactgta                                              18

<210> SEQ ID NO 51
<211> LENGTH: 18
<212> TYPE: DNA
<213> ORGANISM: Unknown
<220> FEATURE:
<223> OTHER INFORMATION: Target of SEQ ID NO: 49 and 50, organisms:
      Burkholderia cenocepacia / vietnamiensis

<400> SEQUENCE: 51
tacagtcggg ggatgacg                                              18

<210> SEQ ID NO 52
<211> LENGTH: 18
<212> TYPE: DNA
<213> ORGANISM: Campylobacter thermophiles

<400> SEQUENCE: 52
gccctaagcg tccttcca                                              18

<210> SEQ ID NO 53
<211> LENGTH: 31
<212> TYPE: DNA
<213> ORGANISM: Artificial sequence
<220> FEATURE:
<223> OTHER INFORMATION: Beacon, target: Campylobacter lari

<400> SEQUENCE: 53
acgctcgaag tgtaagcaac taaatgagcg t                               31

<210> SEQ ID NO 54
<211> LENGTH: 19
<212> TYPE: DNA
<213> ORGANISM: Artificial sequence
<220> FEATURE:
<223> OTHER INFORMATION: Probe, target: Camplyobacter lari

<400> SEQUENCE: 54
gaagtgtaag caactaaat                                             19

<210> SEQ ID NO 55
<211> LENGTH: 19
<212> TYPE: DNA
<213> ORGANISM: Campylobacter lari

<400> SEQUENCE: 55
atttagttgc ttacacttc                                             19

<210> SEQ ID NO 56
<211> LENGTH: 30

```
<212> TYPE: DNA
<213> ORGANISM: Artificial sequence
<220> FEATURE:
<223> OTHER INFORMATION: Beacon, target: Campylobacter jejuni

<400> SEQUENCE: 56
acgctcagct aaccacttat accggagcgt                                    30

<210> SEQ ID NO 57
<211> LENGTH: 18
<212> TYPE: DNA
<213> ORGANISM: Artificial sequence
<220> FEATURE:
<223> OTHER INFORMATION: Probe, target: Campylobacter jejuni

<400> SEQUENCE: 57
agctaaccac ttataccg                                                 18

<210> SEQ ID NO 58
<211> LENGTH: 18
<212> TYPE: DNA
<213> ORGANISM: Campylobacter jejuni

<400> SEQUENCE: 58
cggtataagt ggttagct                                                 18

<210> SEQ ID NO 59
<211> LENGTH: 32
<212> TYPE: DNA
<213> ORGANISM: Artificial sequence
<220> FEATURE:
<223> OTHER INFORMATION: Beacon, target: Campylobacter upsaliensis

<400> SEQUENCE: 59
ccgctccgtg tgtcgcccta ggcgtagagc gg                                 32

<210> SEQ ID NO 60
<211> LENGTH: 20
<212> TYPE: DNA
<213> ORGANISM: Artificial sequence
<220> FEATURE:
<223> OTHER INFORMATION: Probe, target: Campylobacter upsaliensis

<400> SEQUENCE: 60
cgtgtgtcgc cctaggcgta                                               20

<210> SEQ ID NO 61
<211> LENGTH: 20
<212> TYPE: DNA
<213> ORGANISM: Campylobacter upsaliensis

<400> SEQUENCE: 61
tacgcctagg gcgacacacg                                               20

<210> SEQ ID NO 62
<211> LENGTH: 30
<212> TYPE: DNA
<213> ORGANISM: Artificial sequence
<220> FEATURE:
<223> OTHER INFORMATION: Beacon, target: Campylobacter coli

<400> SEQUENCE: 62
ccgctctcga tggcatcagg ggttgagcgg                                    30

<210> SEQ ID NO 63
```

```
<211> LENGTH: 18
<212> TYPE: DNA
<213> ORGANISM: Artificial sequence
<220> FEATURE:
<223> OTHER INFORMATION: Probe, target: Campylobacter coli

<400> SEQUENCE: 63
tcgatggcat cagggggtt                                                  18

<210> SEQ ID NO 64
<211> LENGTH: 18
<212> TYPE: DNA
<213> ORGANISM: Campylobacter coli

<400> SEQUENCE: 64
aacccctgat gccatcga                                                   18

<210> SEQ ID NO 65
<211> LENGTH: 18
<212> TYPE: DNA
<213> ORGANISM: Artificial sequence
<220> FEATURE:
<223> OTHER INFORMATION: Probe, target: Campylobacter coli (competitor)

<400> SEQUENCE: 65
tcgacggcat cagggggtt                                                  18

<210> SEQ ID NO 66
<211> LENGTH: 18
<212> TYPE: DNA
<213> ORGANISM: Campylobacter coli

<400> SEQUENCE: 66
aacccctgat gccgtcga                                                   18

<210> SEQ ID NO 67
<211> LENGTH: 39
<212> TYPE: DNA
<213> ORGANISM: Artificial sequence
<220> FEATURE:
<223> OTHER INFORMATION: Beacon, targets: Chlamydia

<400> SEQUENCE: 67
acgccggcgt tagctgatat cacatagatc gcccagcgt                            39

<210> SEQ ID NO 68
<211> LENGTH: 18
<212> TYPE: DNA
<213> ORGANISM: Artificial sequence
<220> FEATURE:
<223> OTHER INFORMATION: Probe, targets: Chlamydia

<400> SEQUENCE: 68
tagctgatat cacataga                                                   18

<210> SEQ ID NO 69
<211> LENGTH: 18
<212> TYPE: DNA
<213> ORGANISM: Unknown
<220> FEATURE:
<223> OTHER INFORMATION: Target of SEQ ID NO: 67 and 68, organisms:
      Chlamydia

<400> SEQUENCE: 69
tctatgtgat atcagcta                                                   18
```

```
<210> SEQ ID NO 70
<211> LENGTH: 41
<212> TYPE: DNA
<213> ORGANISM: Artificial sequence
<220> FEATURE:
<223> OTHER INFORMATION: Beacon, targets: Chlamydiaceae

<400> SEQUENCE: 70
tccgccggcg tctttccgcc tacacgccct cgcccagcgg a                         41

<210> SEQ ID NO 71
<211> LENGTH: 18
<212> TYPE: DNA
<213> ORGANISM: Artificial sequence
<220> FEATURE:
<223> OTHER INFORMATION: Probe, targets: Chlamydiaceae

<400> SEQUENCE: 71
ctttccgcct acacgccc                                                   18

<210> SEQ ID NO 72
<211> LENGTH: 18
<212> TYPE: DNA
<213> ORGANISM: Unknown
<220> FEATURE:
<223> OTHER INFORMATION: Target of SEQ ID NO: 70 and 71, organisms:
      Chlamydiaceae

<400> SEQUENCE: 72
gggcgtgtag gcggaaag                                                   18

<210> SEQ ID NO 73
<211> LENGTH: 41
<212> TYPE: DNA
<213> ORGANISM: Artificial sequence
<220> FEATURE:
<223> OTHER INFORMATION: Beacon, targets: Chlamydiales

<400> SEQUENCE: 73
tccgccggcg tcctccgtat taccgcagct cgcccagcgg a                         41

<210> SEQ ID NO 74
<211> LENGTH: 18
<212> TYPE: DNA
<213> ORGANISM: Artificial sequence
<220> FEATURE:
<223> OTHER INFORMATION: Probe, targets: Chlamydiales

<400> SEQUENCE: 74
cctccgtatt accgcagc                                                   18

<210> SEQ ID NO 75
<211> LENGTH: 18
<212> TYPE: DNA
<213> ORGANISM: Unknown
<220> FEATURE:
<223> OTHER INFORMATION: Target of SEQ ID NO: 73 and 74, organisms:
      Chlamydiales

<400> SEQUENCE: 75
gctgcggtaa tacggagg                                                   18

<210> SEQ ID NO 76
<211> LENGTH: 39
<212> TYPE: DNA
<213> ORGANISM: Artificial sequence
```

-continued

```
<220> FEATURE:
<223> OTHER INFORMATION: Beacon, targets: Chlamydophila

<400> SEQUENCE: 76
acgccggcgt ctaactttcc tttccgcctc gcccagcgt                              39

<210> SEQ ID NO 77
<211> LENGTH: 18
<212> TYPE: DNA
<213> ORGANISM: Artificial sequence
<220> FEATURE:
<223> OTHER INFORMATION: Probe, targets: Chlamydophila

<400> SEQUENCE: 77
ctaactttcc tttccgcc                                                     18

<210> SEQ ID NO 78
<211> LENGTH: 18
<212> TYPE: DNA
<213> ORGANISM: Unknown
<220> FEATURE:
<223> OTHER INFORMATION: Target of SEQ ID NO: 76 and 77, organisms:
      Chlamydophila

<400> SEQUENCE: 78
ggcggaaagg aaagttag                                                     18

<210> SEQ ID NO 79
<211> LENGTH: 41
<212> TYPE: DNA
<213> ORGANISM: Artificial sequence
<220> FEATURE:
<223> OTHER INFORMATION: Beacon, target: Chlamydia pneumoniae

<400> SEQUENCE: 79
tccaccggcg tctcttcctc aaccgaaagt cgcccagtgg a                           41

<210> SEQ ID NO 80
<211> LENGTH: 18
<212> TYPE: DNA
<213> ORGANISM: Artificial sequence
<220> FEATURE:
<223> OTHER INFORMATION: Probe, target: Chlamydia pneumoniae

<400> SEQUENCE: 80
ctcttcctca accgaaag                                                     18

<210> SEQ ID NO 81
<211> LENGTH: 18
<212> TYPE: DNA
<213> ORGANISM: Chlamydia pneumoniae

<400> SEQUENCE: 81
ctttcggttg aggaagag                                                     18

<210> SEQ ID NO 82
<211> LENGTH: 41
<212> TYPE: DNA
<213> ORGANISM: Artificial sequence
<220> FEATURE:
<223> OTHER INFORMATION: Beacon, targets: "Chlamydia psittaci" group

<400> SEQUENCE: 82
tcagccggcg taaggcaaaa ccaactccct cgcccagctg a                           41
```

```
<210> SEQ ID NO 83
<211> LENGTH: 18
<212> TYPE: DNA
<213> ORGANISM: Artificial sequence
<220> FEATURE:
<223> OTHER INFORMATION: Probe, targets: “Chlamydia psittaci” group

<400> SEQUENCE: 83
aaggcaaaac caactccc                                                18

<210> SEQ ID NO 84
<211> LENGTH: 18
<212> TYPE: DNA
<213> ORGANISM: Unknown
<220> FEATURE:
<223> OTHER INFORMATION: Target of SEQ ID NO: 82 and 83, organisms:
      “Chlamydia psittaci” group

<400> SEQUENCE: 84
gggagttggt tttgcctt                                                18

<210> SEQ ID NO 85
<211> LENGTH: 39
<212> TYPE: DNA
<213> ORGANISM: Artificial sequence
<220> FEATURE:
<223> OTHER INFORMATION: Beacon, targets: Subgroup of the
      Parachlamydiaceae

<400> SEQUENCE: 85
ccgccggcgt tccgttttct ccgcctactc gcccagcgg                         39

<210> SEQ ID NO 86
<211> LENGTH: 18
<212> TYPE: DNA
<213> ORGANISM: Artificial sequence
<220> FEATURE:
<223> OTHER INFORMATION: Probe, targets: Subgroup of the
      Parachlamydiaceae

<400> SEQUENCE: 86
tccgttttct ccgcctac                                                18

<210> SEQ ID NO 87
<211> LENGTH: 18
<212> TYPE: DNA
<213> ORGANISM: Unknown
<220> FEATURE:
<223> OTHER INFORMATION: Target of SEQ ID NO: 85 and 86, organisms:
      Subgroup of the Parachlamydiaceae

<400> SEQUENCE: 87
gtaggcggag aaaacgga                                                18

<210> SEQ ID NO 88
<211> LENGTH: 41
<212> TYPE: DNA
<213> ORGANISM: Artificial sequence
<220> FEATURE:
<223> OTHER INFORMATION: Beacon, targets: Chlamydia ssp.

<400> SEQUENCE: 88
tccgccggcg tgctcccctt gctttcgcgt cgcccagcgg a                      41

<210> SEQ ID NO 89
<211> LENGTH: 18
<212> TYPE: DNA
```

```
<213> ORGANISM: Artificial sequence
<220> FEATURE:
<223> OTHER INFORMATION: Probe, targets: Chlamydia ssp.

<400> SEQUENCE: 89
gctccccttg ctttcgcg                                                   18

<210> SEQ ID NO 90
<211> LENGTH: 18
<212> TYPE: DNA
<213> ORGANISM: Unknown
<220> FEATURE:
<223> OTHER INFORMATION: Target of SEQ ID NO: 88 and 89, organisms:
      Chlamydia ssp.

<400> SEQUENCE: 90
cgcgaaagca aggggagc                                                   18

<210> SEQ ID NO 91
<211> LENGTH: 30
<212> TYPE: DNA
<213> ORGANISM: Artificial sequence
<220> FEATURE:
<223> OTHER INFORMATION: Beacon, target: Chlamydia trachomatis

<400> SEQUENCE: 91
acgctctcgg atgcccaaat atcggagcgt                                      30

<210> SEQ ID NO 92
<211> LENGTH: 18
<212> TYPE: DNA
<213> ORGANISM: Artificial sequence
<220> FEATURE:
<223> OTHER INFORMATION: Probe, target: Chlamydia trachomatis

<400> SEQUENCE: 92
tcggatgccc aaatatcg                                                   18

<210> SEQ ID NO 93
<211> LENGTH: 18
<212> TYPE: DNA
<213> ORGANISM: Chlamydia trachomatis

<400> SEQUENCE: 93
cgatatttgg gcatccga                                                   18

<210> SEQ ID NO 94
<211> LENGTH: 29
<212> TYPE: DNA
<213> ORGANISM: Artificial sequence
<220> FEATURE:
<223> OTHER INFORMATION: Beacon, target: Candida albicans

<400> SEQUENCE: 94
ggaatggcta cccagaagga aaccattcc                                       29

<210> SEQ ID NO 95
<211> LENGTH: 20
<212> TYPE: DNA
<213> ORGANISM: Artificial sequence
<220> FEATURE:
<223> OTHER INFORMATION: Probe, target: Candida albicans

<400> SEQUENCE: 95
aatggctacc cagaaggaaa                                                 20
```

<210> SEQ ID NO 96
<211> LENGTH: 20
<212> TYPE: DNA
<213> ORGANISM: Candida albicans

<400> SEQUENCE: 96
tttccttctg ggtagccatt                                               20

<210> SEQ ID NO 97
<211> LENGTH: 36
<212> TYPE: DNA
<213> ORGANISM: Artificial sequence
<220> FEATURE:
<223> OTHER INFORMATION: Beacon, target: Candida krusei

<400> SEQUENCE: 97
ccgctctgta ttagctctag atttccacgg gagcgg                             36

<210> SEQ ID NO 98
<211> LENGTH: 24
<212> TYPE: DNA
<213> ORGANISM: Artificial sequence
<220> FEATURE:
<223> OTHER INFORMATION: Probe, target: Candida krusei

<400> SEQUENCE: 98
tgtattagct ctagatttcc acgg                                          24

<210> SEQ ID NO 99
<211> LENGTH: 24
<212> TYPE: DNA
<213> ORGANISM: Candida krusei

<400> SEQUENCE: 99
ccgtggaaat ctagagctaa taca                                          24

<210> SEQ ID NO 100
<211> LENGTH: 32
<212> TYPE: DNA
<213> ORGANISM: Artificial sequence
<220> FEATURE:
<223> OTHER INFORMATION: Beacon, target: Candida dubliniensis

<400> SEQUENCE: 100
gtttgccccg aaagagtaac ttgcaggcaa ac                                 32

<210> SEQ ID NO 101
<211> LENGTH: 20
<212> TYPE: DNA
<213> ORGANISM: Artificial sequence
<220> FEATURE:
<223> OTHER INFORMATION: Probe, target: Candida dubliniensis

<400> SEQUENCE: 101
ccccgaaaga gtaacttgca                                               20

<210> SEQ ID NO 102
<211> LENGTH: 20
<212> TYPE: DNA
<213> ORGANISM: Candida dubliniensis

<400> SEQUENCE: 102
tgcaagttac tctttcgggg                                               20

```
<210> SEQ ID NO 103
<211> LENGTH: 40
<212> TYPE: DNA
<213> ORGANISM: Artificial sequence
<220> FEATURE:
<223> OTHER INFORMATION: Beacon, target: Candida glabrata

<400> SEQUENCE: 103
gccgccggcg tggccaccca ggcccaaatc gcccagcggc                    40

<210> SEQ ID NO 104
<211> LENGTH: 17
<212> TYPE: DNA
<213> ORGANISM: Artificial sequence
<220> FEATURE:
<223> OTHER INFORMATION: Probe, target: Candida glabrata

<400> SEQUENCE: 104
ggccacccag gcccaaa                                             17

<210> SEQ ID NO 105
<211> LENGTH: 17
<212> TYPE: DNA
<213> ORGANISM: Candida glabrata

<400> SEQUENCE: 105
tttgggcctg ggtggcc                                             17

<210> SEQ ID NO 106
<211> LENGTH: 43
<212> TYPE: DNA
<213> ORGANISM: Artificial sequence
<220> FEATURE:
<223> OTHER INFORMATION: Beacon, target: Candida parapsilosis

<400> SEQUENCE: 106
gccgccggcg tgccaaaaag gctagccaga atcgcccagc ggc                43

<210> SEQ ID NO 107
<211> LENGTH: 20
<212> TYPE: DNA
<213> ORGANISM: Artificial sequence
<220> FEATURE:
<223> OTHER INFORMATION: Probe, target: Candida parapsilosis

<400> SEQUENCE: 107
gccaaaaagg ctagccagaa                                          20

<210> SEQ ID NO 108
<211> LENGTH: 20
<212> TYPE: DNA
<213> ORGANISM: Candida parapsilosis

<400> SEQUENCE: 108
ttctggctag ccttttttggc                                         20

<210> SEQ ID NO 109
<211> LENGTH: 24
<212> TYPE: DNA
<213> ORGANISM: Artificial sequence
<220> FEATURE:
<223> OTHER INFORMATION: Beacon, targets: Candida spp.

<400> SEQUENCE: 109
acgcgcttgg ctggccggtc gcgt                                     24
```

<210> SEQ ID NO 110
<211> LENGTH: 16
<212> TYPE: DNA
<213> ORGANISM: Artificial sequence
<220> FEATURE:
<223> OTHER INFORMATION: Probe, targets: Candida spp.

<400> SEQUENCE: 110
gaccggccag ccaagc                                                  16

<210> SEQ ID NO 111
<211> LENGTH: 16
<212> TYPE: DNA
<213> ORGANISM: Unknown
<220> FEATURE:
<223> OTHER INFORMATION: Target of SEQ ID NO: 109 and 110, organisms:
      Candida spp.

<400> SEQUENCE: 111
gcttggctgg ccggtc                                                  16

<210> SEQ ID NO 112
<211> LENGTH: 44
<212> TYPE: DNA
<213> ORGANISM: Artificial sequence
<220> FEATURE:
<223> OTHER INFORMATION: Beacon, target: Candida tropicales

<400> SEQUENCE: 112
accgccggcg ttacgcatca gaaagatgga cctcgcccag cggt                   44

<210> SEQ ID NO 113
<211> LENGTH: 21
<212> TYPE: DNA
<213> ORGANISM: Artificial sequence
<220> FEATURE:
<223> OTHER INFORMATION: Probe, target: Candida tropicales

<400> SEQUENCE: 113
tacgcatcag aaagatggac c                                            21

<210> SEQ ID NO 114
<211> LENGTH: 21
<212> TYPE: DNA
<213> ORGANISM: Candida tropicalis

<400> SEQUENCE: 114
ggtccatctt tctgatgcgt a                                            21

<210> SEQ ID NO 115
<211> LENGTH: 40
<212> TYPE: DNA
<213> ORGANISM: Artificial sequence
<220> FEATURE:
<223> OTHER INFORMATION: Beacon, target: Citrobacter freundii

<400> SEQUENCE: 115
tgccggattc tacttgttag gtgactgcgt aatcccggca                        40

<210> SEQ ID NO 116
<211> LENGTH: 21
<212> TYPE: DNA
<213> ORGANISM: Artificial sequence
<220> FEATURE:
<223> OTHER INFORMATION: Probe, target: Citrobacter freundii

```
<400> SEQUENCE: 116
ctacttgtta ggtgactgcg t                                              21

<210> SEQ ID NO 117
<211> LENGTH: 21
<212> TYPE: DNA
<213> ORGANISM: Citrobacter freundii

<400> SEQUENCE: 117
acgcagtcac ctaacaagta g                                              21

<210> SEQ ID NO 118
<211> LENGTH: 33
<212> TYPE: DNA
<213> ORGANISM: Artificial sequence
<220> FEATURE:
<223> OTHER INFORMATION: Beacon, target: Clostridium botulinum

<400> SEQUENCE: 118
tcttgtagtg ccgtttcatg cgaaactaca aga                                 33

<210> SEQ ID NO 119
<211> LENGTH: 22
<212> TYPE: DNA
<213> ORGANISM: Artificial sequence
<220> FEATURE:
<223> OTHER INFORMATION: Probe, target: Clostridium botulinum

<400> SEQUENCE: 119
gccgtttcat gcgaaactac aa                                             22

<210> SEQ ID NO 120
<211> LENGTH: 22
<212> TYPE: DNA
<213> ORGANISM: Clostridium botulinum

<400> SEQUENCE: 120
ttgtagtttc gcatgaaacg gc                                             22

<210> SEQ ID NO 121
<211> LENGTH: 46
<212> TYPE: DNA
<213> ORGANISM: Artificial sequence
<220> FEATURE:
<223> OTHER INFORMATION: Beacon, target: Clostridium difficile

<400> SEQUENCE: 121
gccgccggcg tcgaagtaaa tcgctcaact tgcatcgccc agcggc                   46

<210> SEQ ID NO 122
<211> LENGTH: 23
<212> TYPE: DNA
<213> ORGANISM: Artificial sequence
<220> FEATURE:
<223> OTHER INFORMATION: Probe, target: Clostridium difficile

<400> SEQUENCE: 122
cgaagtaaat cgctcaactt gca                                            23

<210> SEQ ID NO 123
<211> LENGTH: 23
<212> TYPE: DNA
<213> ORGANISM: Clostridium difficile

<400> SEQUENCE: 123
```

```
tgcaagttga gcgatttact tcg                                              23

<210> SEQ ID NO 124
<211> LENGTH: 29
<212> TYPE: DNA
<213> ORGANISM: Artificial sequence
<220> FEATURE:
<223> OTHER INFORMATION: Beacon, targets: Clostridium spp.

<400> SEQUENCE: 124
cgctcacacc cgtccgccgc taatgagcg                                        29

<210> SEQ ID NO 125
<211> LENGTH: 18
<212> TYPE: DNA
<213> ORGANISM: Artificial sequence
<220> FEATURE:
<223> OTHER INFORMATION: Probe, targets: Clostridium spp.

<400> SEQUENCE: 125
cacccgtccg ccgctaat                                                    18

<210> SEQ ID NO 126
<211> LENGTH: 18
<212> TYPE: DNA
<213> ORGANISM: Unknown
<220> FEATURE:
<223> OTHER INFORMATION: Target of SEQ ID NO: 124 and 125, organisms:
      Clostridium spp.

<400> SEQUENCE: 126
attagcggcg gacgggtg                                                    18

<210> SEQ ID NO 127
<211> LENGTH: 47
<212> TYPE: DNA
<213> ORGANISM: Artificial sequence
<220> FEATURE:
<223> OTHER INFORMATION: Beacon, target: Clostridium perfringens

<400> SEQUENCE: 127
gccgccggcg tgattgctcc tttggttgaa tgatgtcgcc cagcggc                    47

<210> SEQ ID NO 128
<211> LENGTH: 24
<212> TYPE: DNA
<213> ORGANISM: Artificial sequence
<220> FEATURE:
<223> OTHER INFORMATION: Probe, target: Clostridium perfringens

<400> SEQUENCE: 128
gattgctcct ttggttgaat gatg                                             24

<210> SEQ ID NO 129
<211> LENGTH: 24
<212> TYPE: DNA
<213> ORGANISM: Clostridium perfringens

<400> SEQUENCE: 129
catcattcaa ccaaaggagc aatc                                             24

<210> SEQ ID NO 130
<211> LENGTH: 31
<212> TYPE: DNA
<213> ORGANISM: Artificial sequence
```

```
<220> FEATURE:
<223> OTHER INFORMATION: Beacon, target: Clostridium perfringens

<400> SEQUENCE: 130
acgctcggtt gaatgatgat gccatgagcg t                              31

<210> SEQ ID NO 131
<211> LENGTH: 23
<212> TYPE: DNA
<213> ORGANISM: Artificial sequence
<220> FEATURE:
<223> OTHER INFORMATION: Probe, target: Clostridium perfringens

<400> SEQUENCE: 131
ggttgaatga tgatgccatc ttt                                       23

<210> SEQ ID NO 132
<211> LENGTH: 23
<212> TYPE: DNA
<213> ORGANISM: Clostridium perfringens

<400> SEQUENCE: 132
aaagatggca tcatcattca acc                                       23

<210> SEQ ID NO 133
<211> LENGTH: 27
<212> TYPE: DNA
<213> ORGANISM: Artificial sequence
<220> FEATURE:
<223> OTHER INFORMATION: Beacon, target: Clostridium tetani

<400> SEQUENCE: 133
gcggacctgt gttactcacc cgtccgc                                   27

<210> SEQ ID NO 134
<211> LENGTH: 20
<212> TYPE: DNA
<213> ORGANISM: Artificial sequence
<220> FEATURE:
<223> OTHER INFORMATION: Probe, target: Clostridium tetani

<400> SEQUENCE: 134
ctgtgttact cacccgtccg                                           20

<210> SEQ ID NO 135
<211> LENGTH: 20
<212> TYPE: DNA
<213> ORGANISM: Clostridium tetani

<400> SEQUENCE: 135
cggacgggtg agtaacacag                                           20

<210> SEQ ID NO 136
<211> LENGTH: 40
<212> TYPE: DNA
<213> ORGANISM: Artificial sequence
<220> FEATURE:
<223> OTHER INFORMATION: Beacon, targets: Enterobacteriaceae

<400> SEQUENCE: 136
tgccggattt tcgtgtttgc acagtgctgt aatcccggca                     40

<210> SEQ ID NO 137
<211> LENGTH: 21
<212> TYPE: DNA
```

```
<213> ORGANISM: Artificial sequence
<220> FEATURE:
<223> OTHER INFORMATION: Probe, targets: Enterobacteriaceae

<400> SEQUENCE: 137
ttcgtgtttg cacagtgctg t                                            21

<210> SEQ ID NO 138
<211> LENGTH: 21
<212> TYPE: DNA
<213> ORGANISM: Unknown
<220> FEATURE:
<223> OTHER INFORMATION: Target of SEQ ID NO: 136 and 137, organisms:
      Enterobacteriaceae

<400> SEQUENCE: 138
acagcactgt gcaaacacga a                                            21

<210> SEQ ID NO 139
<211> LENGTH: 37
<212> TYPE: DNA
<213> ORGANISM: Artificial sequence
<220> FEATURE:
<223> OTHER INFORMATION: Beacon, targets: Enterobacteriaceae

<400> SEQUENCE: 139
tgccggattt ctcgcgaggt cgcttctaat cccggca                           37

<210> SEQ ID NO 140
<211> LENGTH: 18
<212> TYPE: DNA
<213> ORGANISM: Artificial sequence
<220> FEATURE:
<223> OTHER INFORMATION: Probe, targets: Enterobacteriaceae

<400> SEQUENCE: 140
tctcgcgagg tcgcttct                                                18

<210> SEQ ID NO 141
<211> LENGTH: 18
<212> TYPE: DNA
<213> ORGANISM: Unknown
<220> FEATURE:
<223> OTHER INFORMATION: Target of SEQ ID NO: 139 and 140, organisms:
      Enterobacteriaceae

<400> SEQUENCE: 141
agaagcgacc tcgcgaga                                                18

<210> SEQ ID NO 142
<211> LENGTH: 39
<212> TYPE: DNA
<213> ORGANISM: Artificial sequence
<220> FEATURE:
<223> OTHER INFORMATION: Beacon, targets: Enterobacteriaceae

<400> SEQUENCE: 142
tgccggattc ccccwctttg gtcttgcgaa atcccggca                         39

<210> SEQ ID NO 143
<211> LENGTH: 20
<212> TYPE: DNA
<213> ORGANISM: Artificial sequence
<220> FEATURE:
<223> OTHER INFORMATION: Probe, targets: Enterobacteriaceae

<400> SEQUENCE: 143
```

```
cccccwcttt ggtcttgcga                                                20
```

<210> SEQ ID NO 144
<211> LENGTH: 20
<212> TYPE: DNA
<213> ORGANISM: Unknown
<220> FEATURE:
<223> OTHER INFORMATION: Target of SEQ ID NO: 142 and 143, organisms:
      Enterobacteriaceae

<400> SEQUENCE: 144

```
tcgcaagacc aaagwgggggg                                               20
```

<210> SEQ ID NO 145
<211> LENGTH: 37
<212> TYPE: DNA
<213> ORGANISM: Artificial sequence
<220> FEATURE:
<223> OTHER INFORMATION: Beacon, targets: Enterococci

<400> SEQUENCE: 145

```
tgccggatta tccatcagcg acacccgaat cccggca                             37
```

<210> SEQ ID NO 146
<211> LENGTH: 18
<212> TYPE: DNA
<213> ORGANISM: Artificial sequence
<220> FEATURE:
<223> OTHER INFORMATION: Probe, targets: Enterococci

<400> SEQUENCE: 146

```
atccatcagc gacacccg                                                  18
```

<210> SEQ ID NO 147
<211> LENGTH: 18
<212> TYPE: DNA
<213> ORGANISM: Unknown
<220> FEATURE:
<223> OTHER INFORMATION: Target of SEQ ID NO: 145 and 146, organisms:
      Enterococci

<400> SEQUENCE: 147

```
cgggtgtcgc tgatggat                                                  18
```

<210> SEQ ID NO 148
<211> LENGTH: 37
<212> TYPE: DNA
<213> ORGANISM: Artificial sequence
<220> FEATURE:
<223> OTHER INFORMATION: Beacon, target: Enterococcus faecalis

<400> SEQUENCE: 148

```
tgccggattc cctctgatgg gtaggttaat cccggca                             37
```

<210> SEQ ID NO 149
<211> LENGTH: 18
<212> TYPE: DNA
<213> ORGANISM: Artificial sequence
<220> FEATURE:
<223> OTHER INFORMATION: Probe, target: Enterococcus faecalis

<400> SEQUENCE: 149

```
ccctctgatg ggtaggtt                                                  18
```

<210> SEQ ID NO 150

-continued

<210> SEQ ID NO 150
<211> LENGTH: 18
<212> TYPE: DNA
<213> ORGANISM: Enterococcus faecalis

<400> SEQUENCE: 150
aacctaccca tcagaggg                                                 18

<210> SEQ ID NO 151
<211> LENGTH: 47
<212> TYPE: DNA
<213> ORGANISM: Artificial sequence
<220> FEATURE:
<223> OTHER INFORMATION: Beacon, target: Enterococcus faecium

<400> SEQUENCE: 151
gccgccggcg tttcaaatca aaccatgcg gtttctcgcc cagcggc                  47

<210> SEQ ID NO 152
<211> LENGTH: 24
<212> TYPE: DNA
<213> ORGANISM: Artificial sequence
<220> FEATURE:
<223> OTHER INFORMATION: Probe, target: Enterococcus faecium

<400> SEQUENCE: 152
ttcaaatcaa aaccatgcgg tttc                                          24

<210> SEQ ID NO 153
<211> LENGTH: 24
<212> TYPE: DNA
<213> ORGANISM: Enterococcus faecium

<400> SEQUENCE: 153
gaaaccgcat ggttttgatt tgaa                                          24

<210> SEQ ID NO 154
<211> LENGTH: 40
<212> TYPE: DNA
<213> ORGANISM: Artificial sequence
<220> FEATURE:
<223> OTHER INFORMATION: Beacon, target: Escherichia coli

<400> SEQUENCE: 154
tgccggattg gaagaagctt gcttctttgc aatcccggca                         40

<210> SEQ ID NO 155
<211> LENGTH: 21
<212> TYPE: DNA
<213> ORGANISM: Artificial sequence
<220> FEATURE:
<223> OTHER INFORMATION: Probe, target: Escherichia coli

<400> SEQUENCE: 155
ggaagaagct tgcttctttg c                                             21

<210> SEQ ID NO 156
<211> LENGTH: 21
<212> TYPE: DNA
<213> ORGANISM: Escherichia coli

<400> SEQUENCE: 156
gcaaagaagc aagcttcttc c                                             21

<210> SEQ ID NO 157
<211> LENGTH: 28

```
<212> TYPE: DNA
<213> ORGANISM: Artificial sequence
<220> FEATURE:
<223> OTHER INFORMATION: Beacon, targets: EU-bacteria

<400> SEQUENCE: 157
cgctcgctgc ctcccgtagg agtgagcg                                      28

<210> SEQ ID NO 158
<211> LENGTH: 18
<212> TYPE: DNA
<213> ORGANISM: Artificial sequence
<220> FEATURE:
<223> OTHER INFORMATION: Probe, targets: EU-bacteria

<400> SEQUENCE: 158
gctgcctccc gtaggagt                                                 18

<210> SEQ ID NO 159
<211> LENGTH: 18
<212> TYPE: DNA
<213> ORGANISM: Unknown
<220> FEATURE:
<223> OTHER INFORMATION: Target of SEQ ID NO: 157 and 158, organisms:
      EU-bacteria

<400> SEQUENCE: 159
actcctacgg gaggcagc                                                 18

<210> SEQ ID NO 160
<211> LENGTH: 30
<212> TYPE: DNA
<213> ORGANISM: Artificial sequence
<220> FEATURE:
<223> OTHER INFORMATION: Beacon, target: Gardnerella vaginalis

<400> SEQUENCE: 160
acgctccacc atgaagcaac ccgtgagcgt                                    30

<210> SEQ ID NO 161
<211> LENGTH: 18
<212> TYPE: DNA
<213> ORGANISM: Artificial sequence
<220> FEATURE:
<223> OTHER INFORMATION: Probe, target: Gardnerella vaginalis

<400> SEQUENCE: 161
caccatgaag caacccgt                                                 18

<210> SEQ ID NO 162
<211> LENGTH: 18
<212> TYPE: DNA
<213> ORGANISM: Gardnerella vaginalis

<400> SEQUENCE: 162
acgggttgct tcatggtg                                                 18

<210> SEQ ID NO 163
<211> LENGTH: 35
<212> TYPE: DNA
<213> ORGANISM: Artificial sequence
<220> FEATURE:
<223> OTHER INFORMATION: Beacon, target: Haemophilus influenzae

<400> SEQUENCE: 163
acccgctatt ccgataatac gcggtattag cgggt                              35
```

<210> SEQ ID NO 164
<211> LENGTH: 23
<212> TYPE: DNA
<213> ORGANISM: Artificial sequence
<220> FEATURE:
<223> OTHER INFORMATION: Probe, target: Haemophilus influenzae

<400> SEQUENCE: 164
ttccgataat acgcggtatt agc                                          23

<210> SEQ ID NO 165
<211> LENGTH: 23
<212> TYPE: DNA
<213> ORGANISM: Haemophilus influenzae

<400> SEQUENCE: 165
gctaataccg cgtattatcg gaa                                          23

<210> SEQ ID NO 166
<211> LENGTH: 39
<212> TYPE: DNA
<213> ORGANISM: Artificial sequence
<220> FEATURE:
<223> OTHER INFORMATION: Beacon, target: Haemophilus influenzae

<400> SEQUENCE: 166
cggtgctcta atacgcggta ttagcgacag agagcaccg                         39

<210> SEQ ID NO 167
<211> LENGTH: 22
<212> TYPE: DNA
<213> ORGANISM: Artificial sequence
<220> FEATURE:
<223> OTHER INFORMATION: Probe, target: Haemophilus influenzae

<400> SEQUENCE: 167
taatacgcgg tattagcgac ag                                           22

<210> SEQ ID NO 168
<211> LENGTH: 22
<212> TYPE: DNA
<213> ORGANISM: Haemophilus influenzae

<400> SEQUENCE: 168
ctgtcgctaa taccgcgtat at                                           22

<210> SEQ ID NO 169
<211> LENGTH: 42
<212> TYPE: DNA
<213> ORGANISM: Artificial sequence
<220> FEATURE:
<223> OTHER INFORMATION: Beacon, target: Klebsiella pneumoniae

<400> SEQUENCE: 169
acgccggcgt aggttattaa cctcatcgcc ttcgcccagc gt                     42

<210> SEQ ID NO 170
<211> LENGTH: 21
<212> TYPE: DNA
<213> ORGANISM: Artificial sequence
<220> FEATURE:
<223> OTHER INFORMATION: Probe, target: Klebsiella pneumoniae

<400> SEQUENCE: 170

```
aggttattaa cctcatcgcc t                                              21

<210> SEQ ID NO 171
<211> LENGTH: 21
<212> TYPE: DNA
<213> ORGANISM: Klebsiella pneumoniae

<400> SEQUENCE: 171
aggcgatgag gttaataacc t                                              21

<210> SEQ ID NO 172
<211> LENGTH: 35
<212> TYPE: DNA
<213> ORGANISM: Artificial sequence
<220> FEATURE:
<223> OTHER INFORMATION: Beacon, target: Klebsiella oxytoca

<400> SEQUENCE: 172
ggaagggata taggttatta acctcactcc cttcc                               35

<210> SEQ ID NO 173
<211> LENGTH: 24
<212> TYPE: DNA
<213> ORGANISM: Artificial sequence
<220> FEATURE:
<223> OTHER INFORMATION: Probe, target: Klebsiella oxytoca

<400> SEQUENCE: 173
aggttattaa cctcactccc ttcc                                           24

<210> SEQ ID NO 174
<211> LENGTH: 24
<212> TYPE: DNA
<213> ORGANISM: Klebsiella oxytoca

<400> SEQUENCE: 174
ggaagggagt gaggttaata acct                                           24

<210> SEQ ID NO 175
<211> LENGTH: 32
<212> TYPE: DNA
<213> ORGANISM: Artificial sequence
<220> FEATURE:
<223> OTHER INFORMATION: Beacon, target: Lactobacillus brevis

<400> SEQUENCE: 175
cgctcattca acggaagctc gttcgatgag cg                                  32

<210> SEQ ID NO 176
<211> LENGTH: 22
<212> TYPE: DNA
<213> ORGANISM: Artificial sequence
<220> FEATURE:
<223> OTHER INFORMATION: Probe, target: Lactobacillus brevis

<400> SEQUENCE: 176
tcattcaacg gaagctcgtt cg                                             22

<210> SEQ ID NO 177
<211> LENGTH: 22
<212> TYPE: DNA
<213> ORGANISM: Lactobacillus brevis

<400> SEQUENCE: 177
cgaacgagct tccgttgaat ga                                             22
```

<210> SEQ ID NO 178
<211> LENGTH: 37
<212> TYPE: DNA
<213> ORGANISM: Artificial sequence
<220> FEATURE:
<223> OTHER INFORMATION: Beacon, target: Legionella pneumophila

<400> SEQUENCE: 178
tgccggatta tctgaccgtc ccaggttaat cccggca                37

<210> SEQ ID NO 179
<211> LENGTH: 18
<212> TYPE: DNA
<213> ORGANISM: Artificial sequence
<220> FEATURE:
<223> OTHER INFORMATION: Probe, target: Legionella pneumophila

<400> SEQUENCE: 179
atctgaccgt cccaggtt                18

<210> SEQ ID NO 180
<211> LENGTH: 18
<212> TYPE: DNA
<213> ORGANISM: Legionella pneumophila

<400> SEQUENCE: 180
aacctgggac ggtcagat                18

<210> SEQ ID NO 181
<211> LENGTH: 30
<212> TYPE: DNA
<213> ORGANISM: Artificial sequence
<220> FEATURE:
<223> OTHER INFORMATION: Beacon, target: Listeria monocytogenes

<400> SEQUENCE: 181
acgctcataa gatgtggcgc atgcgagcgt                30

<210> SEQ ID NO 182
<211> LENGTH: 18
<212> TYPE: DNA
<213> ORGANISM: Artificial sequence
<220> FEATURE:
<223> OTHER INFORMATION: Probe, target: Listeria monocytogenes

<400> SEQUENCE: 182
ataagatgtg gcgcatgc                18

<210> SEQ ID NO 183
<211> LENGTH: 18
<212> TYPE: DNA
<213> ORGANISM: Listeria monocytogenes

<400> SEQUENCE: 183
gcatgcgcca catcttat                18

<210> SEQ ID NO 184
<211> LENGTH: 18
<212> TYPE: DNA
<213> ORGANISM: Artificial sequence
<220> FEATURE:
<223> OTHER INFORMATION: Probe, target: Mycoplasma hominis

<400> SEQUENCE: 184

```
attgctaacc tcgctcga                                                  18

<210> SEQ ID NO 185
<211> LENGTH: 18
<212> TYPE: DNA
<213> ORGANISM: Mycoplasma hominis

<400> SEQUENCE: 185
tcgagcgagg ttagcaat                                                  18

<210> SEQ ID NO 186
<211> LENGTH: 30
<212> TYPE: DNA
<213> ORGANISM: Artificial sequence
<220> FEATURE:
<223> OTHER INFORMATION: Beacon, targets: Proteus mirabili / vulgaris

<400> SEQUENCE: 186
ggcgtcacac cggatacgta gtgctacgcc                                     30

<210> SEQ ID NO 187
<211> LENGTH: 18
<212> TYPE: DNA
<213> ORGANISM: Artificial sequence
<220> FEATURE:
<223> OTHER INFORMATION: Probe, targets: Proteus mirabili / vulgaris

<400> SEQUENCE: 187
ggcgtcacac cggatacg                                                  18

<210> SEQ ID NO 188
<211> LENGTH: 19
<212> TYPE: DNA
<213> ORGANISM: Unknown
<220> FEATURE:
<223> OTHER INFORMATION: Target of SEQ ID NO: 186 and 187, organisms:
      Proteus mirabili / vulgaris

<400> SEQUENCE: 188
ccgtatccgg tgtgacgcc                                                 19

<210> SEQ ID NO 189
<211> LENGTH: 26
<212> TYPE: DNA
<213> ORGANISM: Artificial sequence
<220> FEATURE:
<223> OTHER INFORMATION: Beacon, target: Pneumocystis-1

<400> SEQUENCE: 189
actcggcttc atgccaacag tcgagt                                         26

<210> SEQ ID NO 190
<211> LENGTH: 18
<212> TYPE: DNA
<213> ORGANISM: Artificial sequence
<220> FEATURE:
<223> OTHER INFORMATION: Probe, target: Pneumocystis-1

<400> SEQUENCE: 190
ggcttcatgc caacagtc                                                  18

<210> SEQ ID NO 191
<211> LENGTH: 18
<212> TYPE: DNA
<213> ORGANISM: Unknown
<220> FEATURE:
```

```
<223> OTHER INFORMATION: Target of SEQ ID NO: 189 and 190, organism:
      Pneumocystis-1

<400> SEQUENCE: 191
gactgttggc atgaagcc                                                   18

<210> SEQ ID NO 192
<211> LENGTH: 28
<212> TYPE: DNA
<213> ORGANISM: Artificial sequence
<220> FEATURE:
<223> OTHER INFORMATION: Beacon, target: Pneumocystis-2

<400> SEQUENCE: 192
gacaccataa gatgccgagc gaggtgtc                                        28

<210> SEQ ID NO 193
<211> LENGTH: 18
<212> TYPE: DNA
<213> ORGANISM: Artificial sequence
<220> FEATURE:
<223> OTHER INFORMATION: Probe, target: Pneumocystis-2

<400> SEQUENCE: 193
cataagatgc cgagcgag                                                   18

<210> SEQ ID NO 194
<211> LENGTH: 18
<212> TYPE: DNA
<213> ORGANISM: Unknown
<220> FEATURE:
<223> OTHER INFORMATION: Target of SEQ ID NO: 192 and 193, organism:
      Pneumocystis-2

<400> SEQUENCE: 194
ctcgctcggc atcttatg                                                   18

<210> SEQ ID NO 195
<211> LENGTH: 43
<212> TYPE: DNA
<213> ORGANISM: Artificial sequence
<220> FEATURE:
<223> OTHER INFORMATION: Beacon, target: Pseudomonas aeruginosa

<400> SEQUENCE: 195
accgccggcg taagacgact cgtcatcacc ttcgcccagc ggt                       43

<210> SEQ ID NO 196
<211> LENGTH: 20
<212> TYPE: DNA
<213> ORGANISM: Artificial sequence
<220> FEATURE:
<223> OTHER INFORMATION: Probe, target: Pseudomonas aeruginosa

<400> SEQUENCE: 196
aagacgactc gtcatcacct                                                 20

<210> SEQ ID NO 197
<211> LENGTH: 20
<212> TYPE: DNA
<213> ORGANISM: Pseudomonas aeruginosa

<400> SEQUENCE: 197
aggtgatgac gagtcgtctt                                                 20
```

-continued

```
<210> SEQ ID NO 198
<211> LENGTH: 44
<212> TYPE: DNA
<213> ORGANISM: Artificial sequence
<220> FEATURE:
<223> OTHER INFORMATION: Beacon, target: Pseudomonas spp.

<400> SEQUENCE: 198
gccgccggcg tggcagattc ctaggcatta cttcgcccag cggc         44

<210> SEQ ID NO 199
<211> LENGTH: 21
<212> TYPE: DNA
<213> ORGANISM: Artificial sequence
<220> FEATURE:
<223> OTHER INFORMATION: Probe, target: Pseudomonas spp.

<400> SEQUENCE: 199
ggcagattcc taggcattac t                                   21

<210> SEQ ID NO 200
<211> LENGTH: 21
<212> TYPE: DNA
<213> ORGANISM: Unknown
<220> FEATURE:
<223> OTHER INFORMATION: Target of SEQ ID NO: 198 and 199, organism:
      Pseudomonas spp.

<400> SEQUENCE: 200
agtaatgcct aggaatctgc c                                   21

<210> SEQ ID NO 201
<211> LENGTH: 31
<212> TYPE: DNA
<213> ORGANISM: Artificial sequence
<220> FEATURE:
<223> OTHER INFORMATION: Beacon, targets: Salmonellae

<400> SEQUENCE: 201
agctctgcgc ttttgtgtac ggggctgagc t                        31

<210> SEQ ID NO 202
<211> LENGTH: 21
<212> TYPE: DNA
<213> ORGANISM: Artificial sequence
<220> FEATURE:
<223> OTHER INFORMATION: Probe, targets: Salmonellae

<400> SEQUENCE: 202
tgcgcttttg tgtacggggc t                                   21

<210> SEQ ID NO 203
<211> LENGTH: 21
<212> TYPE: DNA
<213> ORGANISM: Unknown
<220> FEATURE:
<223> OTHER INFORMATION: Target of SEQ ID NO: 201, 202 and 204,
      organisms: Salmonellae

<400> SEQUENCE: 203
agccccgtac acaaaagcgc a                                   21

<210> SEQ ID NO 204
<211> LENGTH: 19
<212> TYPE: DNA
<213> ORGANISM: Artificial sequence
<220> FEATURE:
```

<223> OTHER INFORMATION: Probe, targets: Salmonellae (331 competitor)

<400> SEQUENCE: 204
gtgcatttgt gtacggggc                                           19

<210> SEQ ID NO 205
<211> LENGTH: 29
<212> TYPE: DNA
<213> ORGANISM: Artificial sequence
<220> FEATURE:
<223> OTHER INFORMATION: Beacon, targets: Salmonellae

<400> SEQUENCE: 205
cgctccttca cctacgtgtc agcggagcg                                29

<210> SEQ ID NO 206
<211> LENGTH: 19
<212> TYPE: DNA
<213> ORGANISM: Artificial sequence
<220> FEATURE:
<223> OTHER INFORMATION: Probe, targets: Salmonellae

<400> SEQUENCE: 206
cttcacctac gtgtcagcg                                           19

<210> SEQ ID NO 207
<211> LENGTH: 19
<212> TYPE: DNA
<213> ORGANISM: Unknown
<220> FEATURE:
<223> OTHER INFORMATION: Target of SEQ ID NO: 205, 206, 210 and 211,
      organisms: Salmonellae

<400> SEQUENCE: 207
cgctgacacg taggtgaag                                           19

<210> SEQ ID NO 208
<211> LENGTH: 20
<212> TYPE: DNA
<213> ORGANISM: Artificial sequence
<220> FEATURE:
<223> OTHER INFORMATION: Probe, targets: Salmonellae

<400> SEQUENCE: 208
tcacctacat atcagcgtgc                                          20

<210> SEQ ID NO 209
<211> LENGTH: 20
<212> TYPE: DNA
<213> ORGANISM: Unknown
<220> FEATURE:
<223> OTHER INFORMATION: Target of SEQ ID NO: 208, organisms:
      Salmonellae

<400> SEQUENCE: 209
cgctgacacg taggtgaaga                                          20

<210> SEQ ID NO 210
<211> LENGTH: 38
<212> TYPE: DNA
<213> ORGANISM: Artificial sequence
<220> FEATURE:
<223> OTHER INFORMATION: Beacon, target: Salmonella

<400> SEQUENCE: 210
tgccggattc ttcacctacg tgtcagcgaa tcccggca                      38

<210> SEQ ID NO 211
<211> LENGTH: 19
<212> TYPE: DNA
<213> ORGANISM: Artificial sequence
<220> FEATURE:
<223> OTHER INFORMATION: Probe, target: Salmonella

<400> SEQUENCE: 211
cttcacctac gtgtcagcg                                                  19

<210> SEQ ID NO 212
<211> LENGTH: 43
<212> TYPE: DNA
<213> ORGANISM: Artificial sequence
<220> FEATURE:
<223> OTHER INFORMATION: Beacon, target: Serratia marcescens

<400> SEQUENCE: 212
gccgccggcg tcgagactct agcttgccag ttcgcccagc ggc                       43

<210> SEQ ID NO 213
<211> LENGTH: 20
<212> TYPE: DNA
<213> ORGANISM: Artificial sequence
<220> FEATURE:
<223> OTHER INFORMATION: Probe, target: Serratia marcescens

<400> SEQUENCE: 213
cgagactcta gcttgccagt                                                 20

<210> SEQ ID NO 214
<211> LENGTH: 20
<212> TYPE: DNA
<213> ORGANISM: Serratia marcescens

<400> SEQUENCE: 214
actggcaagc tagagtctcg                                                 20

<210> SEQ ID NO 215
<211> LENGTH: 43
<212> TYPE: DNA
<213> ORGANISM: Artificial sequence
<220> FEATURE:
<223> OTHER INFORMATION: Beacon, target: Staphylococcus aureus

<400> SEQUENCE: 215
tgccggattt tctcgtccgt tcgctcgact tgcaatcccg gca                       43

<210> SEQ ID NO 216
<211> LENGTH: 24
<212> TYPE: DNA
<213> ORGANISM: Artificial sequence
<220> FEATURE:
<223> OTHER INFORMATION: Probe, target: Staphylococcus aureus

<400> SEQUENCE: 216
ttctcgtccg ttcgctcgac ttgc                                            24

<210> SEQ ID NO 217
<211> LENGTH: 24
<212> TYPE: DNA
<213> ORGANISM: Staphylococcus aureus

<400> SEQUENCE: 217

```
gcaagtcgag cgaacggacg agaa                                          24

<210> SEQ ID NO 218
<211> LENGTH: 28
<212> TYPE: DNA
<213> ORGANISM: Artificial sequence
<220> FEATURE:
<223> OTHER INFORMATION: Beacon, targets: Staphylococci

<400> SEQUENCE: 218
gcaactttcg cacatcagcg tcagttgc                                      28

<210> SEQ ID NO 219
<211> LENGTH: 21
<212> TYPE: DNA
<213> ORGANISM: Artificial sequence
<220> FEATURE:
<223> OTHER INFORMATION: Probe, targets: Staphylococci

<400> SEQUENCE: 219
tttcgcacat cagcgtcagt t                                             21

<210> SEQ ID NO 220
<211> LENGTH: 21
<212> TYPE: DNA
<213> ORGANISM: Unknown
<220> FEATURE:
<223> OTHER INFORMATION: Target of SEQ ID NO: 218 and 219, organisms:
      Staphylococci

<400> SEQUENCE: 220
aactgacgct gatgtgcgaa a                                             21

<210> SEQ ID NO 221
<211> LENGTH: 30
<212> TYPE: DNA
<213> ORGANISM: Artificial sequence
<220> FEATURE:
<223> OTHER INFORMATION: Beacon, target: Stenotrophomonas maltophilia

<400> SEQUENCE: 221
ccctctacca cactctagtc gggtagaggg                                    30

<210> SEQ ID NO 222
<211> LENGTH: 21
<212> TYPE: DNA
<213> ORGANISM: Artificial sequence
<220> FEATURE:
<223> OTHER INFORMATION: Probe, target: Stenotrophomonas maltophilia

<400> SEQUENCE: 222
ccctctacca cactctagtc g                                             21

<210> SEQ ID NO 223
<211> LENGTH: 21
<212> TYPE: DNA
<213> ORGANISM: Stenotrophomonas maltophilia

<400> SEQUENCE: 223
cgactagagt gtggtagagg g                                             21

<210> SEQ ID NO 224
<211> LENGTH: 44
<212> TYPE: DNA
<213> ORGANISM: Artificial sequence
<220> FEATURE:
```

<223> OTHER INFORMATION: Beacon, target: Streptococcus agalactiae

<400> SEQUENCE: 224
gccgccggcg tactcctacc aacgttcttc tctcgcccag cggc    44

<210> SEQ ID NO 225
<211> LENGTH: 21
<212> TYPE: DNA
<213> ORGANISM: Artificial sequence
<220> FEATURE:
<223> OTHER INFORMATION: Probe, target: Streptococcus agalactiae

<400> SEQUENCE: 225
actcctacca acgttcttct c    21

<210> SEQ ID NO 226
<211> LENGTH: 21
<212> TYPE: DNA
<213> ORGANISM: Streptococcus agalactiae

<400> SEQUENCE: 226
gagaagaacg ttggtaggag t    21

<210> SEQ ID NO 227
<211> LENGTH: 35
<212> TYPE: DNA
<213> ORGANISM: Artificial sequence
<220> FEATURE:
<223> OTHER INFORMATION: Beacon, targets: Streptococci

<400> SEQUENCE: 227
ggccttcgcc gtccctttct ggttagttga aggcc    35

<210> SEQ ID NO 228
<211> LENGTH: 21
<212> TYPE: DNA
<213> ORGANISM: Artificial sequence
<220> FEATURE:
<223> OTHER INFORMATION: Probe, targets: Streptococci

<400> SEQUENCE: 228
gccgtccctt tctggttagt t    21

<210> SEQ ID NO 229
<211> LENGTH: 21
<212> TYPE: DNA
<213> ORGANISM: Unknown
<220> FEATURE:
<223> OTHER INFORMATION: Target of SEQ ID NO: 227 and 228, organisms:
      Streptococci

<400> SEQUENCE: 229
aactaaccag aaagggacgg c    21

<210> SEQ ID NO 230
<211> LENGTH: 36
<212> TYPE: DNA
<213> ORGANISM: Artificial sequence
<220> FEATURE:
<223> OTHER INFORMATION: Beacon, target: Streptococcus pneumoniae

<400> SEQUENCE: 230
gcgttaagca aatgtcatgc aacatctact taacgc    36

<210> SEQ ID NO 231

```
<211> LENGTH: 25
<212> TYPE: DNA
<213> ORGANISM: Artificial sequence
<220> FEATURE:
<223> OTHER INFORMATION: Probe, target: Streptococcus pneumoniae

<400> SEQUENCE: 231
ttaagcaaat gtcatgcaac atcta                                         25

<210> SEQ ID NO 232
<211> LENGTH: 25
<212> TYPE: DNA
<213> ORGANISM: Streptococcus pneumoniae

<400> SEQUENCE: 232
tagatgttgc atgacatttg cttaa                                         25

<210> SEQ ID NO 233
<211> LENGTH: 38
<212> TYPE: DNA
<213> ORGANISM: Artificial sequence
<220> FEATURE:
<223> OTHER INFORMATION: Beacon, target: Streptococcus pyogenes

<400> SEQUENCE: 233
tgccttcgag caattgcccc ttttaaatta cgaaggca                            38

<210> SEQ ID NO 234
<211> LENGTH: 24
<212> TYPE: DNA
<213> ORGANISM: Artificial sequence
<220> FEATURE:
<223> OTHER INFORMATION: Probe, target: Streptococcus pyogenes

<400> SEQUENCE: 234
gagcaattgc ccctttaaa ttac                                           24

<210> SEQ ID NO 235
<211> LENGTH: 24
<212> TYPE: DNA
<213> ORGANISM: Streptococcus pyogenes

<400> SEQUENCE: 235
gtaatttaaa aggggcaatt gctc                                          24

<210> SEQ ID NO 236
<211> LENGTH: 30
<212> TYPE: DNA
<213> ORGANISM: Artificial sequence
<220> FEATURE:
<223> OTHER INFORMATION: Beacon, target: Ureaplasma urealyticum

<400> SEQUENCE: 236
acgctcgttc cccaactccc tactgagcgt                                    30

<210> SEQ ID NO 237
<211> LENGTH: 18
<212> TYPE: DNA
<213> ORGANISM: Artificial sequence
<220> FEATURE:
<223> OTHER INFORMATION: Probe, target: Ureaplasma urealyticum

<400> SEQUENCE: 237
gttccccaac tccctact                                                 18
```

```
<210> SEQ ID NO 238
<211> LENGTH: 18
<212> TYPE: DNA
<213> ORGANISM: Ureaplasma urealyticum

<400> SEQUENCE: 238
agtagggagt tggggaac                                            18

<210> SEQ ID NO 239
<211> LENGTH: 26
<212> TYPE: DNA
<213> ORGANISM: Artificial sequence
<220> FEATURE:
<223> OTHER INFORMATION: Beacon, targets: Urogenital-Peptostreptococci

<400> SEQUENCE: 239
actccccctt gtgtaaggca gggagt                                   26

<210> SEQ ID NO 240
<211> LENGTH: 18
<212> TYPE: DNA
<213> ORGANISM: Artificial sequence
<220> FEATURE:
<223> OTHER INFORMATION: Probe, targets: Urogenital-Peptostreptococci

<400> SEQUENCE: 240
ccccttgtgt aaggcagg                                            18

<210> SEQ ID NO 241
<211> LENGTH: 18
<212> TYPE: DNA
<213> ORGANISM: Unknown
<220> FEATURE:
<223> OTHER INFORMATION: Target of SEQ ID NO: 239 and 240, organisms:
      Urogenital-Peptostreptococci

<400> SEQUENCE: 241
cctgccttac acaagggg                                            18

<210> SEQ ID NO 242
<211> LENGTH: 30
<212> TYPE: DNA
<213> ORGANISM: Artificial sequence
<220> FEATURE:
<223> OTHER INFORMATION: Beacon, target: Yersinia enterocolitica

<400> SEQUENCE: 242
acgctcccca ctttggtccg aagagagcgt                               30

<210> SEQ ID NO 243
<211> LENGTH: 18
<212> TYPE: DNA
<213> ORGANISM: Artificial sequence
<220> FEATURE:
<223> OTHER INFORMATION: Probe. target: Yersinia enterocolitica

<400> SEQUENCE: 243
cccactttgg tccgaaga                                            18

<210> SEQ ID NO 244
<211> LENGTH: 18
<212> TYPE: DNA
<213> ORGANISM: Yersinia enterocolitica

<400> SEQUENCE: 244
tcttcggacc aaagtggg                                            18
```

```
<210> SEQ ID NO 245
<211> LENGTH: 36
<212> TYPE: DNA
<213> ORGANISM: Artificial sequence
<220> FEATURE:
<223> OTHER INFORMATION: Beacon, target: Acinetobacter spp.

<400> SEQUENCE: 245
tgccggtttt aggccagatg gctgccaatc ccggca                           36

<210> SEQ ID NO 246
<211> LENGTH: 28
<212> TYPE: DNA
<213> ORGANISM: Artificial sequence
<220> FEATURE:
<223> OTHER INFORMATION: Beacon, target: Aspergillus fumigatus

<400> SEQUENCE: 246 ccggccccg agaggtgata catgccgg                                     28

<210> SEQ ID NO 247
<211> LENGTH: 31
<212> TYPE: DNA
<213> ORGANISM: Artificial sequence
<220> FEATURE:
<223> OTHER INFORMATION: Beacon, target: Aspergillus niger

<400> SEQUENCE: 247
ccggcaatta caatgcggac tccgaagccg g                                31

<210> SEQ ID NO 248
<211> LENGTH: 29
<212> TYPE: DNA
<213> ORGANISM: Artificial sequence
<220> FEATURE:
<223> OTHER INFORMATION: Beacon, target: Mycobacterium avium Complex

<400> SEQUENCE: 248
cccggtgttg atataaggca ggtgccggg                                   29

<210> SEQ ID NO 249
<211> LENGTH: 30
<212> TYPE: DNA
<213> ORGANISM: Artificial sequence
<220> FEATURE:
<223> OTHER INFORMATION: Beacon, target: Mycobacterium chelonae

<400> SEQUENCE: 249
cccggcatga agtgtgtggt cctatccggg                                  30

<210> SEQ ID NO 250
<211> LENGTH: 30
<212> TYPE: DNA
<213> ORGANISM: Artificial sequence
<220> FEATURE:
<223> OTHER INFORMATION: Beacon, target: Mycobacterium fortuitum

<400> SEQUENCE: 250
cccggtgaag cgcgtggtca tattcccggg                                  30

<210> SEQ ID NO 251
<211> LENGTH: 30
<212> TYPE: DNA
<213> ORGANISM: Artificial sequence
<220> FEATURE:
```

<223> OTHER INFORMATION: Beacon, target: Mycobacterium gordonae

<400> SEQUENCE: 251
cccggtgtgt cctgtggtcc tattcccggg                                              30

<210> SEQ ID NO 252
<211> LENGTH: 30
<212> TYPE: DNA
<213> ORGANISM: Artificial sequence
<220> FEATURE:
<223> OTHER INFORMATION: Beacon, target: Mycobacterium intracellulare

<400> SEQUENCE: 252
cccggacatg cgtctaaagg tcctaccggg                                              30

<210> SEQ ID NO 253
<211> LENGTH: 30
<212> TYPE: DNA
<213> ORGANISM: Artificial sequence
<220> FEATURE:
<223> OTHER INFORMATION: Beacon, targets: Mycobacterium kansasii /
      gastri

<400> SEQUENCE: 253
cccggtagag ctgagacgta tcgatccggg                                              30

<210> SEQ ID NO 254
<211> LENGTH: 28
<212> TYPE: DNA
<213> ORGANISM: Artificial sequence
<220> FEATURE:
<223> OTHER INFORMATION: Beacon, target: Mycobacterium malmoense

<400> SEQUENCE: 254
ccgcgccact gaaacgccct attcgcgg                                                28

<210> SEQ ID NO 255
<211> LENGTH: 28
<212> TYPE: DNA
<213> ORGANISM: Artificial sequence
<220> FEATURE:
<223> OTHER INFORMATION: Beacon, target: Mycobacterium smegmatis

<400> SEQUENCE: 255
cccggcacgt cgagggctct gacccggg                                                28

<210> SEQ ID NO 256
<211> LENGTH: 24
<212> TYPE: DNA
<213> ORGANISM: Artificial sequence
<220> FEATURE:
<223> OTHER INFORMATION: Beacon, target: Mycobacterium tuberculosis
      complex

<400> SEQUENCE: 256
ccaccggaga ggaaaaggag gtgg                                                    24

<210> SEQ ID NO 257
<211> LENGTH: 27
<212> TYPE: DNA
<213> ORGANISM: Artificial sequence
<220> FEATURE:
<223> OTHER INFORMATION: Beacon, target: Mycobacterium xenopi

<400> SEQUENCE: 257
ccgcgccgct accaaacgct ttcgcgg                                                 27

```
<210> SEQ ID NO 258
<211> LENGTH: 30
<212> TYPE: DNA
<213> ORGANISM: Artificial sequence
<220> FEATURE:
<223> OTHER INFORMATION: Beacon, target: Shigella

<400> SEQUENCE: 258
ccgggtcacc ctgtatcgca cgcctcccgg                                    30

<210> SEQ ID NO 259
<211> LENGTH: 34
<212> TYPE: DNA
<213> ORGANISM: Artificial sequence
<220> FEATURE:
<223> OTHER INFORMATION: Beacon, target: Citrobacter freundii

<400> SEQUENCE: 259
cccggtcgct tcattacgct atgtatccac cggg                               34

<210> SEQ ID NO 260
<211> LENGTH: 34
<212> TYPE: DNA
<213> ORGANISM: Artificial sequence
<220> FEATURE:
<223> OTHER INFORMATION: Beacon, target: Streptococcus pyogenes

<400> SEQUENCE: 260
cgctcgagca attgcccctt ttaaattacg agcg                               34

<210> SEQ ID NO 261
<211> LENGTH: 36
<212> TYPE: DNA
<213> ORGANISM: Artificial sequence
<220> FEATURE:
<223> OTHER INFORMATION: Beacon, target: Streptococcus pneumoniae

<400> SEQUENCE: 261
ccgttaagca aatgtcatgc aacatctact taacgg                             36

<210> SEQ ID NO 262
<211> LENGTH: 35
<212> TYPE: DNA
<213> ORGANISM: Artificial sequence
<220> FEATURE:
<223> OTHER INFORMATION: Beacon, targets: Streptococci (F111)

<400> SEQUENCE: 262
cgccttcgcc gtccctttct ggttagttga aggcg                              35

<210> SEQ ID NO 263
<211> LENGTH: 31
<212> TYPE: DNA
<213> ORGANISM: Artificial sequence
<220> FEATURE:
<223> OTHER INFORMATION: Beacon, target: Streptococcus agalactiae

<400> SEQUENCE: 263
ccgctactcc taccaacgtt cttctcagcg g                                  31

<210> SEQ ID NO 264
<211> LENGTH: 32
<212> TYPE: DNA
<213> ORGANISM: Artificial sequence
<220> FEATURE:
```

<223> OTHER INFORMATION: Beacon, target: Serratia marcescens

<400> SEQUENCE: 264
ccgctccgag actctagctt gccagtgagc gg                                          32

<210> SEQ ID NO 265
<211> LENGTH: 31
<212> TYPE: DNA
<213> ORGANISM: Artificial sequence
<220> FEATURE:
<223> OTHER INFORMATION: Beacon, targets: Pseudomonas spp.

<400> SEQUENCE: 265
cgctcggcag attcctaggc attactgagc g                                           31

<210> SEQ ID NO 266
<211> LENGTH: 28
<212> TYPE: DNA
<213> ORGANISM: Artificial sequence
<220> FEATURE:
<223> OTHER INFORMATION: Beacon, targets: Staphylococci

<400> SEQUENCE: 266
ccaactttcg cacatcagcg tcagttgg                                               28

<210> SEQ ID NO 267
<211> LENGTH: 30
<212> TYPE: DNA
<213> ORGANISM: Artificial sequence
<220> FEATURE:
<223> OTHER INFORMATION: Beacon, target: Pseudomonas aeruginosa

<400> SEQUENCE: 267
cccggaagac gactcgtcat cagctccggg                                             30

<210> SEQ ID NO 268
<211> LENGTH: 26
<212> TYPE: DNA
<213> ORGANISM: Artificial sequence
<220> FEATURE:
<223> OTHER INFORMATION: Beacon, target: Legionella pneumophila

<400> SEQUENCE: 268
ccggatctga ccgtcccagg ttccgg                                                 26

<210> SEQ ID NO 269
<211> LENGTH: 35
<212> TYPE: DNA
<213> ORGANISM: Artificial sequence
<220> FEATURE:
<223> OTHER INFORMATION: Beacon, target: Klebsiella oxytoca

<400> SEQUENCE: 269
ccgaggtagg ttattaacct cactcccttc ctcgg                                       35

<210> SEQ ID NO 270
<211> LENGTH: 29
<212> TYPE: DNA
<213> ORGANISM: Artificial sequence
<220> FEATURE:
<223> OTHER INFORMATION: Beacon, target: Staphylococcus aureus

<400> SEQUENCE: 270
cccctcaagc ttctcgtccg ttcgagggg                                              29

```
<210> SEQ ID NO 271
<211> LENGTH: 30
<212> TYPE: DNA
<213> ORGANISM: Artificial sequence
<220> FEATURE:
<223> OTHER INFORMATION: Beacon, target: Listeria monocytogenes

<400> SEQUENCE: 271
cctagcatgc gccacatctt atcagctagg                                        30

<210> SEQ ID NO 272
<211> LENGTH: 29
<212> TYPE: DNA
<213> ORGANISM: Artificial sequence
<220> FEATURE:
<223> OTHER INFORMATION: Beacon, target: Klebsiella pneumoniae

<400> SEQUENCE: 272
caggcttagg ttattaacct catcgcctg                                         29

<210> SEQ ID NO 273
<211> LENGTH: 30
<212> TYPE: DNA
<213> ORGANISM: Artificial sequence
<220> FEATURE:
<223> OTHER INFORMATION: Beacon, target: Haemophilus influenzae

<400> SEQUENCE: 273
cccggccgca ctttcatctt ccgatccggg                                        30

<210> SEQ ID NO 274
<211> LENGTH: 30
<212> TYPE: DNA
<213> ORGANISM: Artificial sequence
<220> FEATURE:
<223> OTHER INFORMATION: Beacon, target: Burkholderia spp.

<400> SEQUENCE: 274
cccggccagt caccaatgca gttccccggg                                        30

<210> SEQ ID NO 275
<211> LENGTH: 27
<212> TYPE: DNA
<213> ORGANISM: Artificial sequence
<220> FEATURE:
<223> OTHER INFORMATION: Beacon, targets: Burkholderia cepatia and
      Burkholderia cenocepatia

<400> SEQUENCE: 275
cctgcctatg tattcagcca tggcagg                                           27

<210> SEQ ID NO 276
<211> LENGTH: 29
<212> TYPE: DNA
<213> ORGANISM: Artificial sequence
<220> FEATURE:
<223> OTHER INFORMATION: Beacon, targets: Burkholderia malii and
      Burkholderia pseudomalei

<400> SEQUENCE: 276
gggcctcgcc tcactagacc tatgccggg                                         29

<210> SEQ ID NO 277
<211> LENGTH: 29
<212> TYPE: DNA
<213> ORGANISM: Artificial sequence
<220> FEATURE:
```

<223> OTHER INFORMATION: Beacon, target: Burkholderia vietnamensis

<400> SEQUENCE: 277
cccggtcgct tctctggacc tatgccggg 29

<210> SEQ ID NO 278
<211> LENGTH: 28
<212> TYPE: DNA
<213> ORGANISM: Artificial sequence
<220> FEATURE:
<223> OTHER INFORMATION: Beacon, target: Burkholderia multivorans

<400> SEQUENCE: 278
cccggcttca cccttccagc gcaccggg 28

<210> SEQ ID NO 279
<211> LENGTH: 30
<212> TYPE: DNA
<213> ORGANISM: Artificial sequence
<220> FEATURE:
<223> OTHER INFORMATION: Beacon, target: Burkholderia gladioli

<400> SEQUENCE: 279
ccagcggtac ggtcactgtt aaactgctgg 30

<210> SEQ ID NO 280
<211> LENGTH: 30
<212> TYPE: DNA
<213> ORGANISM: Artificial sequence
<220> FEATURE:
<223> OTHER INFORMATION: Beacon, targets: Acinetobacter spp.

<400> SEQUENCE: 280
ccgtagacca tcctctccca tactctacgg 30

<210> SEQ ID NO 281
<211> LENGTH: 23
<212> TYPE: DNA
<213> ORGANISM: Artificial sequence
<220> FEATURE:
<223> OTHER INFORMATION: Beacon, target: Acinetobacter baumannii

<400> SEQUENCE: 281
ccgctaggtc cggtagcaag cgg 23

<210> SEQ ID NO 282
<211> LENGTH: 28
<212> TYPE: DNA
<213> ORGANISM: Artificial sequence
<220> FEATURE:
<223> OTHER INFORMATION: Beacon, target: Aspergillus flavus

<400> SEQUENCE: 282
cggcctacat tccgggagcc tttggccg 28

<210> SEQ ID NO 283
<211> LENGTH: 29
<212> TYPE: DNA
<213> ORGANISM: Artificial sequence
<220> FEATURE:
<223> OTHER INFORMATION: Beacon, target: Aspergillus terreus

<400> SEQUENCE: 283
ccgatcagac accccgcccc atagatcgg 29

```
<210> SEQ ID NO 284
<211> LENGTH: 31
<212> TYPE: DNA
<213> ORGANISM: Artificial sequence
<220> FEATURE:
<223> OTHER INFORMATION: Beacon, targets: Bacteroides / Prevotella

<400> SEQUENCE: 284
ccgcggtgtc tcagttccaa tgtgggcgcg g                              31

<210> SEQ ID NO 285
<211> LENGTH: 32
<212> TYPE: DNA
<213> ORGANISM: Artificial sequence
<220> FEATURE:
<223> OTHER INFORMATION: Beacon, targets: Borrelia burgdorferi /
      garinii / afzelii / valaisiana

<400> SEQUENCE: 285
cccggggtaa cagataacaa gggttgcccg gg                             32

<210> SEQ ID NO 286
<211> LENGTH: 29
<212> TYPE: DNA
<213> ORGANISM: Artificial sequence
<220> FEATURE:
<223> OTHER INFORMATION: Beacon, target: Bordetella pertussis

<400> SEQUENCE: 286
ccgggctccc cacactttcg tgcacccgg                                 29

<210> SEQ ID NO 287
<211> LENGTH: 28
<212> TYPE: DNA
<213> ORGANISM: Artificial sequence
<220> FEATURE:
<223> OTHER INFORMATION: Beacon, target: Escherichia coli

<400> SEQUENCE: 287
ccggcaaaga agcaagcttc ttccccgg                                  28

<210> SEQ ID NO 288
<211> LENGTH: 30
<212> TYPE: DNA
<213> ORGANISM: Artificial sequence
<220> FEATURE:
<223> OTHER INFORMATION: Beacon, target: Gardnerella vaginalis

<400> SEQUENCE: 288
ccgctccacc atgaagcaac ccgtgagcgg                                30

<210> SEQ ID NO 289
<211> LENGTH: 29
<212> TYPE: DNA
<213> ORGANISM: Artificial sequence
<220> FEATURE:
<223> OTHER INFORMATION: Beacon, targets: Eu-bacteria

<400> SEQUENCE: 289
ccgcgtgctg cctcccgtag gagtcgcgg                                 29

<210> SEQ ID NO 290
<211> LENGTH: 33
<212> TYPE: DNA
<213> ORGANISM: Artificial sequence
<220> FEATURE:
<223> OTHER INFORMATION: Beacons, target: Enterococcus faecium
```

```
<400> SEQUENCE: 290
cttcaaatca aaaccatgcg gtttcatttg aag                                    33

<210> SEQ ID NO 291
<211> LENGTH: 32
<212> TYPE: DNA
<213> ORGANISM: Artificial sequence
<220> FEATURE:
<223> OTHER INFORMATION: Beacon, target: Stenotrophomonas maltophilia

<400> SEQUENCE: 291
cccggaccct ctaccacact ctagtcgccg gg                                     32

<210> SEQ ID NO 292
<211> LENGTH: 25
<212> TYPE: DNA
<213> ORGANISM: Artificial sequence
<220> FEATURE:
<223> OTHER INFORMATION: Beacon, target: Enterococcus faecalis

<400> SEQUENCE: 292
caaccaccct ctgatgggta ggttg                                             25

<210> SEQ ID NO 293
<211> LENGTH: 29
<212> TYPE: DNA
<213> ORGANISM: Artificial sequence
<220> FEATURE:
<223> OTHER INFORMATION: Beacons, targets: Enterococci

<400> SEQUENCE: 293
cccggcatcc atcagcgaca cccgccggg                                         29

<210> SEQ ID NO 294
<211> LENGTH: 28
<212> TYPE: DNA
<213> ORGANISM: Artificial sequence
<220> FEATURE:
<223> OTHER INFORMATION: Beacon, targets: Enterobacteriaceae

<400> SEQUENCE: 294
cccggtctcg cgaggtcgct tctccggg                                          28

<210> SEQ ID NO 295
<211> LENGTH: 31
<212> TYPE: DNA
<213> ORGANISM: Artificial sequence
<220> FEATURE:
<223> OTHER INFORMATION: Beacon, target: Clostridium perfringens

<400> SEQUENCE: 295
gcatcagatt gctcctttgg ttgaatgatg c                                      31

<210> SEQ ID NO 296
<211> LENGTH: 28
<212> TYPE: DNA
<213> ORGANISM: Artificial sequence
<220> FEATURE:
<223> OTHER INFORMATION: Beacon, targets: Clostridium spp.

<400> SEQUENCE: 296
cccggtaccg tcattatcgt cccccggg                                          28

<210> SEQ ID NO 297
```

```
<211> LENGTH: 25
<212> TYPE: DNA
<213> ORGANISM: Artificial sequence
<220> FEATURE:
<223> OTHER INFORMATION: Beacon, target: Chlamydia trachomatis

<400> SEQUENCE: 297
ccgctcggat gcccaaatat cgcgg                                        25

<210> SEQ ID NO 298
<211> LENGTH: 32
<212> TYPE: DNA
<213> ORGANISM: Artificial sequence
<220> FEATURE:
<223> OTHER INFORMATION: Beacon, target: Candida dubliniensis

<400> SEQUENCE: 298
cccggcccga aagagtaact tgcaaaaccg gg                                32

<210> SEQ ID NO 299
<211> LENGTH: 27
<212> TYPE: DNA
<213> ORGANISM: Artificial sequence
<220> FEATURE:
<223> OTHER INFORMATION: Beacon, target: Candida glabrata

<400> SEQUENCE: 299
cccggaggca aggggcgcaa aaccggg                                      27

<210> SEQ ID NO 300
<211> LENGTH: 29
<212> TYPE: DNA
<213> ORGANISM: Artificial sequence
<220> FEATURE:
<223> OTHER INFORMATION: Beacon, target: Candida krusei (Issatchenkia
      orientalis)

<400> SEQUENCE: 300
ccgtgacctg cagcaagaac cgatcacgg                                    29

<210> SEQ ID NO 301
<211> LENGTH: 29
<212> TYPE: DNA
<213> ORGANISM: Artificial sequence
<220> FEATURE:
<223> OTHER INFORMATION: Beacon, target: Candida lusitaniae (Clavispora
      lusitaniae)

<400> SEQUENCE: 301
cactgccgac tcagaccacg aaagcagtg                                    29

<210> SEQ ID NO 302
<211> LENGTH: 30
<212> TYPE: DNA
<213> ORGANISM: Artificial sequence
<220> FEATURE:
<223> OTHER INFORMATION: Beacon, target: Candida albicans

<400> SEQUENCE: 302
ccgcgtttac acagacccgg gtcatcgcgg                                   30

<210> SEQ ID NO 303
<211> LENGTH: 34
<212> TYPE: DNA
<213> ORGANISM: Artificial sequence
<220> FEATURE:
<223> OTHER INFORMATION: Beacon, target: Candida tropicalis
```

```
<400> SEQUENCE: 303
cctcggacat tccaacgcaa ttctcctacc gagg                                34

<210> SEQ ID NO 304
<211> LENGTH: 34
<212> TYPE: DNA
<213> ORGANISM: Artificial sequence
<220> FEATURE:
<223> OTHER INFORMATION: Beacon, target: Candida parapsilosis

<400> SEQUENCE: 304
cccggcacat ttctttgcac ttatcctacc cggg                                34

<210> SEQ ID NO 305
<211> LENGTH: 30
<212> TYPE: DNA
<213> ORGANISM: Artificial sequence
<220> FEATURE:
<223> OTHER INFORMATION: Beacon, target: Chlamydia pneumoniae

<400> SEQUENCE: 305
ccgggctctt cctcaaccga aaggtcccgg                                     30

<210> SEQ ID NO 306
<211> LENGTH: 28
<212> TYPE: DNA
<213> ORGANISM: Artificial sequence
<220> FEATURE:
<223> OTHER INFORMATION: Beacon, targets: Chlamydia psittaci group

<400> SEQUENCE: 306
ccggaaggca aaccaactc ccatccgg                                        28

<210> SEQ ID NO 307
<211> LENGTH: 28
<212> TYPE: DNA
<213> ORGANISM: Artificial sequence
<220> FEATURE:
<223> OTHER INFORMATION: Beacon, targets: Campylobacter (pathogenic
      thermophiles)

<400> SEQUENCE: 307
cccgggccct aagcgtcctt ccaccggg                                       28

<210> SEQ ID NO 308
<211> LENGTH: 28
<212> TYPE: DNA
<213> ORGANISM: Artificial sequence
<220> FEATURE:
<223> OTHER INFORMATION: Beacon, target: Campylobacter coli

<400> SEQUENCE: 308
cgctctcgat ggcatcaggg gttgagcg                                       28

<210> SEQ ID NO 309
<211> LENGTH: 34
<212> TYPE: DNA
<213> ORGANISM: Artificial sequence
<220> FEATURE:
<223> OTHER INFORMATION: Beacon, target: Campylobacter lari

<400> SEQUENCE: 309
cccggcccga agtgttagca actaaatcgc cggg                                34
```

```
<210> SEQ ID NO 310
<211> LENGTH: 33
<212> TYPE: DNA
<213> ORGANISM: Artificial sequence
<220> FEATURE:
<223> OTHER INFORMATION: Beacon, target: Campylobacter jejuni

<400> SEQUENCE: 310
ccgggtaagc taaccacacc ttataccgcc cgg                                33

<210> SEQ ID NO 311
<211> LENGTH: 34
<212> TYPE: DNA
<213> ORGANISM: Artificial sequence
<220> FEATURE:
<223> OTHER INFORMATION: Beacon, target: Campylobacter upsaliensis

<400> SEQUENCE: 311
cccgggccgt gtgtcgccct aggcgtagcc cggg                               34

<210> SEQ ID NO 312
<211> LENGTH: 33
<212> TYPE: DNA
<213> ORGANISM: Artificial sequence
<220> FEATURE:
<223> OTHER INFORMATION: Beacon, target: Pneumocystis carinii

<400> SEQUENCE: 312
ccctgctatc cagtaactga aaccgatgca ggg                                33

<210> SEQ ID NO 313
<211> LENGTH: 32
<212> TYPE: DNA
<213> ORGANISM: Artificial sequence
<220> FEATURE:
<223> OTHER INFORMATION: Beacon, target: Mycoplasma pneumoniae

<400> SEQUENCE: 313
cctccgtgat agctgtttcc aactaccgga gg                                 32

<210> SEQ ID NO 314
<211> LENGTH: 29
<212> TYPE: DNA
<213> ORGANISM: Artificial sequence
<220> FEATURE:
<223> OTHER INFORMATION: Beacon, target: Cryptococcus neoformans

<400> SEQUENCE: 314
cctggtatga ttcaccatag agggccagg                                     29

<210> SEQ ID NO 315
<211> LENGTH: 29
<212> TYPE: DNA
<213> ORGANISM: Artificial sequence
<220> FEATURE:
<223> OTHER INFORMATION: Beacon, target: EHEC

<400> SEQUENCE: 315
cccggtcacc ccataaaaga ggctccggg                                     29

<210> SEQ ID NO 316
<211> LENGTH: 25
<212> TYPE: DNA
<213> ORGANISM: Artificial sequence
<220> FEATURE:
<223> OTHER INFORMATION: Beacon, target: Neisseria meningitidis
```

```
<400> SEQUENCE: 316
caccgttatc ccccactact cggtg                                          25

<210> SEQ ID NO 317
<211> LENGTH: 28
<212> TYPE: DNA
<213> ORGANISM: Artificial sequence
<220> FEATURE:
<223> OTHER INFORMATION: Beacon, target: Neisseria gonorrhoeae

<400> SEQUENCE: 317
cccggacccc gccaaccagc taaccggg                                       28

<210> SEQ ID NO 318
<211> LENGTH: 32
<212> TYPE: DNA
<213> ORGANISM: Artificial sequence
<220> FEATURE:
<223> OTHER INFORMATION: Beacon, target: Clostridium difficile

<400> SEQUENCE: 318
cgggtcgaag taaatcgctc aacttgcacc cg                                  32

<210> SEQ ID NO 319
<211> LENGTH: 28
<212> TYPE: DNA
<213> ORGANISM: Artificial sequence
<220> FEATURE:
<223> OTHER INFORMATION: Beacon, target: Clostridium botulinum

<400> SEQUENCE: 319
cgttgccgtt tcatgcgaaa ctacaacg                                       28

<210> SEQ ID NO 320
<211> LENGTH: 27
<212> TYPE: DNA
<213> ORGANISM: Artificial sequence
<220> FEATURE:
<223> OTHER INFORMATION: Beacon, target: Clostridium tetani

<400> SEQUENCE: 320
ccggaactgt gttactcacc cgtccgg                                        27

<210> SEQ ID NO 321
<211> LENGTH: 28
<212> TYPE: DNA
<213> ORGANISM: Artificial sequence
<220> FEATURE:
<223> OTHER INFORMATION: Beacon, target: Peptostreptococcus anaerobius

<400> SEQUENCE: 321
ccggcctttg atatatctac gatgccgg                                       28

<210> SEQ ID NO 322
<211> LENGTH: 28
<212> TYPE: DNA
<213> ORGANISM: Artificial sequence
<220> FEATURE:
<223> OTHER INFORMATION: Beacon, target: Peptostreptococcus magnus

<400> SEQUENCE: 322
ccgcctaatc cgaaatgaat tctggcgg                                       28

<210> SEQ ID NO 323
<211> LENGTH: 32
```

-continued

<210> SEQ ID NO 323
<211> LENGTH: 32
<212> TYPE: DNA
<213> ORGANISM: Artificial sequence
<220> FEATURE:
<223> OTHER INFORMATION: Beacon, target: Peptostreptococcus magnus

<400> SEQUENCE: 323
ccgccatgtg tttctacgat tttatgcggc gg                          32

<210> SEQ ID NO 324
<211> LENGTH: 31
<212> TYPE: DNA
<213> ORGANISM: Artificial sequence
<220> FEATURE:
<223> OTHER INFORMATION: Beacon, target: Peptostreptococcus micros

<400> SEQUENCE: 324
cccggacttt catttcattt ccattcccgg g                           31

<210> SEQ ID NO 325
<211> LENGTH: 31
<212> TYPE: DNA
<213> ORGANISM: Artificial sequence
<220> FEATURE:
<223> OTHER INFORMATION: Beacon, target: Enterococcus faecalis

<400> SEQUENCE: 325
ccatcggcac tcgggaggaa agaagcgatg g                           31

<210> SEQ ID NO 326
<211> LENGTH: 31
<212> TYPE: DNA
<213> ORGANISM: Artificial sequence
<220> FEATURE:
<223> OTHER INFORMATION: Beacon, target: Enterococcus faecium

<400> SEQUENCE: 326
cgcccatgcg gttttgattg ttatacgggc g                           31

<210> SEQ ID NO 327
<211> LENGTH: 32
<212> TYPE: DNA
<213> ORGANISM: Artificial sequence
<220> FEATURE:
<223> OTHER INFORMATION: Beacon, target: Enterococcus casseliflavus

<400> SEQUENCE: 327
ccgcgcaagg gacgaacatt ttactctcgc gg                          32

<210> SEQ ID NO 328
<211> LENGTH: 30
<212> TYPE: DNA
<213> ORGANISM: Artificial sequence
<220> FEATURE:
<223> OTHER INFORMATION: Beacon, target: Enterococcus gallinarum

<400> SEQUENCE: 328
ccgcgcaagg gatgaacgtt ctactcgcgg                             30

<210> SEQ ID NO 329
<211> LENGTH: 30
<212> TYPE: DNA
<213> ORGANISM: Artificial sequence
<220> FEATURE:
<223> OTHER INFORMATION: Beacon, target: Candida albicans

<400> SEQUENCE: 329

-continued cccggtttcc ttctgggtag ccattccggg          30

<210> SEQ ID NO 330
<211> LENGTH: 32
<212> TYPE: DNA
<213> ORGANISM: Artificial sequence
<220> FEATURE:
<223> OTHER INFORMATION: Beacon, target: Morganella morganii (Proteus morganii)

<400> SEQUENCE: 330
ccggcaagac tctagctgac cagtatcgcc gg       32

<210> SEQ ID NO 331
<211> LENGTH: 28
<212> TYPE: DNA
<213> ORGANISM: Artificial sequence
<220> FEATURE:
<223> OTHER INFORMATION: Beacon, target: Proteus mirabilis

<400> SEQUENCE: 331
cgccgatagt gcaaggtccg aagcggcg            28

<210> SEQ ID NO 332
<211> LENGTH: 27
<212> TYPE: DNA
<213> ORGANISM: Artificial sequence
<220> FEATURE:
<223> OTHER INFORMATION: Beacon, target: Proteus vulgaris

<400> SEQUENCE: 332
ccgccgtaga cgtcatgcgg taggcgg             27

<210> SEQ ID NO 333
<211> LENGTH: 30
<212> TYPE: DNA
<213> ORGANISM: Artificial sequence
<220> FEATURE:
<223> OTHER INFORMATION: Beacon, target: Treponema pallidum

<400> SEQUENCE: 333
cccggtccgc cactctagag aaacgccggg          30

<210> SEQ ID NO 334
<211> LENGTH: 30
<212> TYPE: DNA
<213> ORGANISM: Artificial sequence
<220> FEATURE:
<223> OTHER INFORMATION: Beacons, target: Trichonomas vaginalis

<400> SEQUENCE: 334
cccgggaatg gcgtgcctct gatgaccggg          30

<210> SEQ ID NO 335
<211> LENGTH: 27
<212> TYPE: DNA
<213> ORGANISM: Artificial sequence
<220> FEATURE:
<223> OTHER INFORMATION: Beacon, targets: Micrococci

<400> SEQUENCE: 335
cccggacctc acagtatcgc aaccggg             27

<210> SEQ ID NO 336
<211> LENGTH: 26
<212> TYPE: DNA

```
<213> ORGANISM: Artificial sequence
<220> FEATURE:
<223> OTHER INFORMATION: Beacon, target: Lactobacillus brevis

<400> SEQUENCE: 336
cggccgcggg atcatccaga aggccg                                          26

<210> SEQ ID NO 337
<211> LENGTH: 33
<212> TYPE: DNA
<213> ORGANISM: Artificial sequence
<220> FEATURE:
<223> OTHER INFORMATION: Beacon, target: Yersinia enterocolitica

<400> SEQUENCE: 337
cccggatctc tgctaaattc cgtggatgcc ggg                                  33

<210> SEQ ID NO 338
<211> LENGTH: 28
<212> TYPE: DNA
<213> ORGANISM: Artificial sequence
<220> FEATURE:
<223> OTHER INFORMATION: Beacon, target: Bacillus cereus

<400> SEQUENCE: 338
ccataccact ctgctcccga aggtatgg                                        28

<210> SEQ ID NO 339
<211> LENGTH: 30
<212> TYPE: DNA
<213> ORGANISM: Artificial sequence
<220> FEATURE:
<223> OTHER INFORMATION: Beacon, target: Vibrio cholerae

<400> SEQUENCE: 339
ctgatgcata tccggtagcg caagcatcag                                      30

<210> SEQ ID NO 340
<211> LENGTH: 32
<212> TYPE: DNA
<213> ORGANISM: Artificial sequence
<220> FEATURE:
<223> OTHER INFORMATION: Beacon, target: Vibrio parahaemolyticus

<400> SEQUENCE: 340
cccggtgcag ctattaacta cactaccccg gg                                   32

<210> SEQ ID NO 341
<211> LENGTH: 32
<212> TYPE: DNA
<213> ORGANISM: Artificial sequence
<220> FEATURE:
<223> OTHER INFORMATION: beacon, targets: Cryptosporidium spp.

<400> SEQUENCE: 341
ccgtacataa ggtgctgaag gagtaagtac gg                                   32

<210> SEQ ID NO 342
<211> LENGTH: 28
<212> TYPE: DNA
<213> ORGANISM: Artificial sequence
<220> FEATURE:
<223> OTHER INFORMATION: Beacon, target: Coxiella burnetii

<400> SEQUENCE: 342
ccgggaccct tgagaatttc ttccccgg                                        28
```

<210> SEQ ID NO 343
<211> LENGTH: 32
<212> TYPE: DNA
<213> ORGANISM: Artificial sequence
<220> FEATURE:
<223> OTHER INFORMATION: Beacon, targets: Bartonella spp.

<400> SEQUENCE: 343
ccggcacaaa tttctctgtg ttattccgcc gg                                        32

<210> SEQ ID NO 344
<211> LENGTH: 32
<212> TYPE: DNA
<213> ORGANISM: Artificial sequence
<220> FEATURE:
<223> OTHER INFORMATION: Beacon, target: Enterobacter sakazakii

<400> SEQUENCE: 344
cccggtctct gcaggattct ctggatgccg gg                                        32

<210> SEQ ID NO 345
<211> LENGTH: 30
<212> TYPE: DNA
<213> ORGANISM: Artificial sequence
<220> FEATURE:
<223> OTHER INFORMATION: Beacon, targets: Ehrlichia spp.

<400> SEQUENCE: 345
ccgcgctaat ctaacgtagg ctcatcgcgg                                           30

<210> SEQ ID NO 346
<211> LENGTH: 32
<212> TYPE: DNA
<213> ORGANISM: Artificial sequence
<220> FEATURE:
<223> OTHER INFORMATION: Beacon, targets: Rickettsia spp.

<400> SEQUENCE: 346
ccgcgcactc actcggtatt gctggatcgc gg                                        32

<210> SEQ ID NO 347
<211> LENGTH: 27
<212> TYPE: DNA
<213> ORGANISM: Artificial sequence
<220> FEATURE:
<223> OTHER INFORMATION: Beacon, target: Rickettsia spotted fever
      complex

<400> SEQUENCE: 347
ctagccccaa ttagtccgtt cggctag                                              27

<210> SEQ ID NO 348
<211> LENGTH: 29
<212> TYPE: DNA
<213> ORGANISM: Artificial sequence
<220> FEATURE:
<223> OTHER INFORMATION: Beacon, targets: Rickettsia typhi complex

<400> SEQUENCE: 348
cgcccgtctg ccactaatta actagggcg                                            29

<210> SEQ ID NO 349
<211> LENGTH: 24
<212> TYPE: DNA
<213> ORGANISM: Artificial sequence

```
<220> FEATURE:
<223> OTHER INFORMATION: Beacon, targets: Leishmania spp.

<400> SEQUENCE: 349
cccggaaaag gcgttacggc cggg                                          24

<210> SEQ ID NO 350
<211> LENGTH: 27
<212> TYPE: DNA
<213> ORGANISM: Artificial sequence
<220> FEATURE:
<223> OTHER INFORMATION: Beacon, target: Toxoplasma gondii

<400> SEQUENCE: 350
ccggctccag gggaagaggc atgccgg                                       27

<210> SEQ ID NO 351
<211> LENGTH: 34
<212> TYPE: DNA
<213> ORGANISM: Artificial sequence
<220> FEATURE:
<223> OTHER INFORMATION: Beacon, targets: Yeast spp.

<400> SEQUENCE: 351
cccgggtatt tacattgtac tcattccaac cggg                               34

<210> SEQ ID NO 352
<211> LENGTH: 28
<212> TYPE: DNA
<213> ORGANISM: Artificial sequence
<220> FEATURE:
<223> OTHER INFORMATION: Beacon, target: Francisella tularensis

<400> SEQUENCE: 352
ccatgcgaca gcccgaaagc cagcatgg                                      28

<210> SEQ ID NO 353
<211> LENGTH: 28
<212> TYPE: DNA
<213> ORGANISM: Artificial sequence
<220> FEATURE:
<223> OTHER INFORMATION: Beacon, targets: Lactobacillus spp. A

<400> SEQUENCE: 353
cccggagttc cactgtcctc ttcccggg                                      28

<210> SEQ ID NO 354
<211> LENGTH: 28
<212> TYPE: DNA
<213> ORGANISM: Artificial sequence
<220> FEATURE:
<223> OTHER INFORMATION: Beacon, targets: Lactobacillus spp. B

<400> SEQUENCE: 354
cccggatcag tctctcaact cggccggg                                      28

<210> SEQ ID NO 355
<211> LENGTH: 28
<212> TYPE: DNA
<213> ORGANISM: Artificial sequence
<220> FEATURE:
<223> OTHER INFORMATION: Beacon, target: Burkholderia cepacia complex

<400> SEQUENCE: 355
cccggttggc aaccctctgt tccccggg                                      28
```

```
<210> SEQ ID NO 356
<211> LENGTH: 27
<212> TYPE: DNA
<213> ORGANISM: Artificial sequence
<220> FEATURE:
<223> OTHER INFORMATION: Beacon, target: Staphylococcus aureus

<400> SEQUENCE: 356
cctgcaagct tctcgtccgt tcgcagg                                          27

<210> SEQ ID NO 357
<211> LENGTH: 29
<212> TYPE: DNA
<213> ORGANISM: Artificial sequence
<220> FEATURE:
<223> OTHER INFORMATION: Beacon, target: Staphylococcus aureus

<400> SEQUENCE: 357
cccctcaagc ttctcgtccg ttcgagggg                                        29

<210> SEQ ID NO 358
<211> LENGTH: 29
<212> TYPE: DNA
<213> ORGANISM: Artificial sequence
<220> FEATURE:
<223> OTHER INFORMATION: Beacon, targets: Eu-bacteria

<400> SEQUENCE: 358
ccgcgtgctg cctcccgtag gagtcgcgg                                        29
```

NUCLEIC ACID BEACONS FOR FLUORESCENT IN-SITU HYBRIDIZATION AND CHIP TECHNOLOGY

The present invention relates to beacons for fluorescent in-situ hybridisation and chip technology.

BACKGROUND/PRIOR ART

Since the wide-spread success of the polymerase chain reaction (PCR) technology, microbiology laboratories are waiting for the application of molecular biology to routine microbiology. This has been held back by an inherent and fundamental problem of molecular biology. Because of its precision, you need to know which tools (probes) to choose. The prerequisite is, that a request has to be specified with respect to organisms to be detected. In clinical samples, however, you do not know which of the over 2000 clinically relevant pathogens is the causative agent of an infection. A rational approach solves the problem Focus must be made on 95% of problem causing organisms If it is known where the sample was taken, and clinical data is present, the number of organisms can be reduced to between 2 and 16.

The number of organisms to cover the 95-percentile in most clinical samples is in the order of 100

This rationale makes it economically feasible to run a DNA-probe based assay on a routine basis.

Grouping of micro-organisms and the very rapid testing for presence/absence of specific or a range of micro-organisms is also of relevance in other fields of microbiological testing: Blood banks, Pharmaceutical industry, Cosmetic industry and the Food industry. Frequently the same organisms are of relevance throughout the disciplines and reaction conditions therefor need to be standardised for all probes.

The detection of ribosomal RNA via Fluorescent in-situ Hybridisation (FISH) or utilising chip technology represents an efficient way of utilising sensitivity and specificity of DNA-probes without having to use an enzymatic amplification step. FISH relies on two approaches to the in-situ detection of targets generating a signal strong enough to be detected with standard measuring devices such as an epifluorescence microscope:

1. Identical molecules are present within a cell in sufficient numbers to bind one specific oligonucletide or nucleotide analogue probe with one fluorophor each.
2. Large probes carrying a plurality of fluorophores e.g. labelled cosmids.

FISH technology for the identification of micro-organisms in their respective environments is well known in the art. Application of FISH for the detection of pathogens is of especial interest to the clinical microbiology and infectiology, where FISH excels in speed and cost efficiency.

Detecting rRNA with chip technology also relieves from the necessity to amplify the target. Total rRNA is extracted from a sample and placed on a chip. Specific probes are concentrated on a small surface area and attract respective rRNA-molecules to give specific presence/absence signals. In order to make such chips economically viable they need to be used repeatedly with as little manipulations as possible. Furthermore the standardisation of probe characteristics is paramount for the generation of reproducible results.

In order to gain acceptance in a routine environment probes must be designed in such a way that all probes for one disease state can be run simultaneously under identical conditions in or on one vessel (chips, micro-fluidic devices or micro titre plates). In the design of the probes and to make the probes economically viable, it must be taken into account that one probe may be of relevance to different disease states. Therefor, not only one set of probes but all probes must work under identical hybridisation conditions. Sequence and length of the working probes must be tested accordingly.

The selection and definition of a working probe cannot be performed by simple sequence comparison and determination of a theoretical $T_m$-value. Depending on the algorithm applied a wide set of values are obtained giving no guidance to the choice of probe sequence suitable for standardised hybridisation conditions.

The choice of algorithm and factors influencing the quality of a probe is discussed widely in the art (1-7). Further guidance may be sought comparing sequences and actual position in the three dimensional structure of the ribosome. In an attempt to rationalise the design of probes Behrens et al (8) investigated the correlation between hybridisation sites and actual accessibility with the help of the 3 Å three dimensional model of the ribosome. Their findings demonstrated that the SDS used in in-situ procedures has a predominant denaturing effect, not captured by algorithms predicting secondary structures.

A further problem in both FISH and chip technology is that the procedure calls for a stringent wash step to remove unbound probes, requiring additional handling steps, reagents and time. The success of a hybridisation may depend largely on the skill and precision applied to the washing step. However, routine applications call for minimal steps and hands-on time, most importantly they must be independent from individual skills.

One solution to the reduction of steps would be the application of fluorescence resonance energy transfer ("FRET") in an oligo-nucleotide or nucleotide analogue hairpin formation (molecular beacon). Several approaches to the development of beacons are known in the art and generalised descriptions to their construction are freely available (13). Beacons are widely used in real time PCR, where they anneal in solution to an increasing number of templates generated by amplifying enzymes (15). Only few attempts have been made to generate beacons for the detection/identification of bacteria on membranes (14). One successful beacon was constructed to detect *E. coli* in whole cells with a peptide nucleic acid (PNA) probe. The corresponding DNA-probe failed to give adequate performance (16). The production of further PNA-beacons is limited due to the poor solubility of PNA based oligonucleotides as laid down in design recommendations (17).

Patent CA 2176266/EP 0745690 gives guidance to the construction of universal stems for real time PCR (9). Surprisingly, these recommendations do not render working beacons when combined with probes designed to identify micro-organisms in-situ. Real time PCR is performed in solution while both ISH (in-situ hybridisation) and chips require fixed targets. Their thermodynamic details were not compatible with in-situ hybridisation and FRET requirements. Thus, universally working stems could not be predicted for applications with fixed targets. It was therefore necessary to empirically search for specific beacons fitting individual oligo-nucleotide or nucleotide analogues in order to accomplish a plurality of beacons working under identical ISH specifications.

In the selection of ISH-beacons care has to be taken that the stem does not hinder the delicate balance of hybridising towards RNA entwined in large protein/RNA complexes such as ribosomes. The accessibility of binding sites is widely discussed in the art and is summarised in (1).

Further limitations in the design of a beacon probe are given by the size of pores generated in the cell wall during the ISH procedure. Adding the same stem to different probes results in distinctly individual beacons. A plurality of probes already form hairpin loops and the addition of a stem does not result in a "beacon" formation. In addition, simply adding bases to form complementary pairs may increase the $T_m$ to such an extent that the hairpin is thermodynamically preferred rather than the hybrid formation. Special stems have to be devised that pull the sequence into beacon formation while maintaining the $T_m$ at or below that of the hybrid. The teachings with respect to the design of beacons (13) show that the increase of the stem length by one base pair increases the $T_m$ by 5° C. and that the $T_m$ of the stem should be 10° C. higher than the $T_m$ of the hybridising sequence.

FISH with single microorganisms, such as bacteria, based upon specific rRNA sequences, may be difficult due to sterical hindrance of the rRNA in the ribosome. In other words, a beacon forming a hairpin may poorly anneal to the embedded rRNA target sequence.

It is therefore the subject of the present invention to provide molecular beacons which overcome the above described disadvantages at least partially. The solution provided in the present invention and preferred embodiments thereof are described in the claims.

Subject of the present invention is a nucleic acid capable of forming a hybrid with a target nucleic acid sequence and capable of forming a stem-loop structure if no hybrid is formed with the target sequence, said nucleic acid comprising
(a) a nucleic acid portion comprising
  (a1) a sequence complementary to the target nucleic acid sequence,
  (a2) a pair of two complementary sequences capable of forming a stem,
(b) an effector and an inhibitor, wherein the inhibitor inhibits the effector when the nucleic acid forms a stem-loop structure, and wherein the effector is active when the nucleic acid is not forming a stem-loop structure.

The nucleic acid of the present invention capable of forming a hybrid with a target nucleic acid sequence and capable of forming a stem-loop structure if no hybrid is formed with the target sequence is also referred herein as "beacon", "molecular beacon", "hairpin", or "hairpin loop", wherein the "open" form (no stem is formed) as well as the "closed" form (the beacon forms a stem) is included. The open form includes a beacon not forming a hybrid with a target sequence and a beacon forming a hybrid with the target sequence.

In particular, the two complementary sequences (a2) are flanking the sequence (a1), i.e. the first sequence (a2) is attached at the 3' end of the sequence (a1) and the second sequence (a2) is attached at the 5' end of the sequence (a1).

The hybrid of the sequence (a1)) with the target sequence is also referred herein as "hybrid with the cognate sequence" or as "cognate hybrid".

In the present invention, the effector may be attached at one of the two complementary sequences capable of forming a stem, whereas the inhibitor may be attached at the other of the two complementary sequences, so that the inhibitor essentially inhibits the effector activity when a stem is formed, and that the effector is active when the hairpin is open. Preferably, the effector is attached at the 5' end or the 3' end of the beacon, respectively, or at a position which is 1, 2, 3, 4, or 5 nucleotides distant to the 5' end or the 3' end, respectively. The inhibitor is preferably attached at the other end not covered by the effector, i.e. at the 3' end or the 5' end, respectively, or at a position which is 1, 2, 3, 4, or 5 nucleotides distant to the 3' end or the 5' end, respectively.

The design of the hairpin loops disclosed herein therefore differs fundamentally from beacons well known in the art.

Hybridisation of the beacon of the present invention with target sequence may take place under conditions where the loop is open. A beacon which is not forming a stem when hybridizing is capable of annealing to a target rRNA sequence, for instance, and can therefor achieve successful hybridisation.

This goal is for instance achieved by a $T_m$ of the beacon (i.e. the $T_m$ of the stem) which is essentially equal to or lower than the $T_m$ of the cognate hybrid (i.e. the hybrid of the beacon with the target sequence). Thus, hybridisation with the target sequence takes place when the stem is open, for instance if hybridisation takes place under essentially $Mg^{2+}$ free conditions.

"Essentially equal $T_m$" of the cognate hybrid and the stem of the beacon refers to melting temperatures differing in less than 5° C., preferably less than 3° C., more preferably less than 2° C., more preferably less than 1° C., more preferably less than 0.5° C., even more preferably less than 0.2° C., most preferably less than 0.1° C.

In order to achieve an inhibition of the effector by the inhibitor, both of which form part of the beacon, in those beacon molecules not hybridising with the target sequence, stem formation must be induced after the hybridisation reaction. This may for instance be achieved by a beacon having a $\Delta G<0$, so the hairpin will form spontaneously. Further, stem formation may be introduced by washing with a $Mg^{2+}$ containing buffer as described herein.

In particular, the hairpin loops are constructed in such a way that under standardised hybridisation conditions (e.g. under essentially $Mg^{2+}$ free conditions) the beacon stem is open so that possible sterical limitations do not hinder the hybridisation process. For instance, sterical limitations may be present when the target sequence is a rRNA sequence. If the effector is a fluorophor, the fluorophor will not be quenched by the close proximity of ribosomal proteins.

Suitable conditions for induction of stem formation after hybridisation include an $Mg^{2+}$ containing buffer, for instance containing about 1 to about 20 mM $Mg^{2+}$, more particular about 5 to about 15 mM $Mg^{2+}$, even more particular about 8 to about 12 mM $Mg^{2+}$, most particular about 10 mM $Mg^{2+}$. The buffer may have a pH>8.

Furthermore, the beacons function in their entirety and cannot be dissected into stem and loop as nearest neighbour and stacking effect have a profound influence in their thermodynamic properties. Preferred beacons of the present invention are summarised in Table 1. They clearly show that the preferred stem sequence is independent from the $\Delta G$, $T_m$, GC content or length of the sequence chosen to identify a species.

In the present invention, the thermodynamic specifications for the individual construction of beacons suitable for standardised conditions are set: The Gibbs energy ($\Delta G$) for the formation of the beacon has to be designed in such a way that
  The beacon will form spontaneously ($\Delta G<0$) in the absence of a cognate target sequence under hybridisation conditions.
  The $\Delta G$ of the cognate hybrid is significantly lower (i.e. is more negative) than the $\Delta G$ of the beacon.
  The respective $\Delta G$ of the beacon is lower than a mismatch or non-cognate sequence.
  The $T_m$ for the formation of the beacon has to be designed in such a way that the $T_m$ of the beacon is lower than or essentially at the $T_m$ of the hybrid.

It is preferred that the $\Delta G$ of the cognate hybrid is in the range of about −17 to about −25 kcal/mol, preferably about −18 to about −24 kcal/mol, more preferably about −19 to about −23 kcal/mol, most preferably about −20 to about −22 kcal/mol under hybridisation conditions.

It is also preferred that the ΔG of the cognate hybrids under hybridisation conditions do not vary more than 5 kcal/mol, preferably no more than 3 kcal/mol, more preferably 2 kcal/mol and most preferably 1 kcal/mol.

Occasionally cognate sequences may form spontaneous hairpin loops, where one arm only needs to be supplemented to achieve the beacon formation. If the target sequence is a rRNA sequence, this, however renders the effector, e.g. the fluorophor, in very close proximity to potentially quenching proteins of the ribosome. In a preferred configuration the stem is extended. In order to conform with said thermodynamic specifications as described herein even with an extended stem a method was devised to keep both the $T_m$ and ΔG within the specifications. According to the present invention, this can be achieved by the introduction of at least one non-matched nucleotide or nucleotide analogue. In the present invention, introduction of at least one non-matched nucleotide may be enhanced by the introduction of an additional nucleotide or nucleotide analogue, so that the two complementary sequences have a different length, and the stem becomes "bended" (see for example position 36 in SEQ ID NO:1), or/and may be achieved by a replacement of a matching nucleotide or nucleotide analogue by a non-matching nucleotide or nucleotide analogue (see for example position 5 in SEQ ID NO: 7). Thus, in the present invention, the "complementary sequences capable of forming a stem" may also include at least one non-matched nucleotide, preferably 1, 2, 3, 4 or 5 non-matched nucleotides.

As can be seen from Table 2 none of the sequences disclosed here could be devised as PNA-beacons due to the said limitations in the construction of PNA-oligonucleotides. The major limitation being in the oligonucleotide length required to have both sufficient specificity and a stem length sufficient to ensure the re-folding of the loop when not hybridised. It is therefore necessary to devise DNA-beacons that are able to hybridise with sufficient affinity and speed to enable the in-situ identification of micro-organisms.

The beacon of the present invention is not a PNA beacon. The backbone of the beacon is preferably a nucleic acid backbone. The beacon may comprise a nucleic acid analogue such as a deoxyribonucleotide analogue or a ribonucleotide analogue in the nucleic acid portion or/and in the linker if a linker is present. This analogue is preferably a nucleotide analogue modified at the sugar moiety, the base or/and the phosphate groups. The nucleotide analogue is preferably not a PNA building block.

Following the said 95-percentile in clinical samples, pathogens can be grouped into disease related groups. Probes towards these organisms must work simultaneously under the said conditions, especially if all probes are to be utilised on one chip. The chip application calls for a stringent standardisation of both the cognate and stem characteristics. If a combination of more than one probe is employed, i.e. at least two probes, all probes have to be designed to work on the same slide/chip simultaneously.

Another subject of the present invention is a combination comprising at least 2, preferably at least 10, at least 20, at least 30, at least 40, or at least 50 beacons. The combination may comprise but is not limited to all of the beacons of Table 1, preferably at the maximum 100, at the maximum 80, at the maximum 70, at the maximum 60, at the maximum 50, at the maximum 40, at the maximum 30 or at the maximum 20 beacons.

In a combination of the present invention, the beacons may have the same or different target sequences. It is preferred that the target sequences of individual beacons are different.

In a combination of beacons of the present invention, the ΔG difference of the individual beacons of the hybrid of the sequences of (a2) or/and the hybrid of the sequence of (a1) with a target sequence may be at the maximum about 4 kcal/mol, preferably at the maximum about 3 kcal/mol, more preferably at the maximum about 2 kcal/mol, and most preferably at the maximum about 1 kcal/mol with respect to the cognate sequence.

In a combination, the $T_m$ values of individual beacons with respect to its respective cognate sequence may differ at the maximum by about 3° C., preferably at the maximum about 2° C., more preferably at the maximum about 1° C.

It is preferred that in the combination of the present invention the individual nucleic acids function uniformly. "Functioning uniformly" means that successful hybridisation can be achieved with different nucleic acids probes of the present invention under the same hybridisation conditions, for instance under standardised hybridisation conditions. In other words, uniformly functioning nucleic acids of the present invention do not require individual optimisation of the hybridisation conditions.

Depending on the disease state certain pathogens most frequently are the causative agents and can thus be compiled into diagnostic groups. Addition or omission of certain pathogens may be required depending on regional epidemiology in order to reach the 95-percentile. The preferred listing of Table 1 covers the requirements of Europe and most of North America.

Yet another aspect of the present invention is a kit or chip which may contain at least two beacons of Table 1 required to detect the listed organisms optionally together with the required hybridisation reagents, Preferably, the chip or kit contains at least 10, at least 20, at least 30, at least 40, or at least 50 beacons. The kit or chip may contain at the maximum all of the beacons of Table 1, preferably at the maximum 100, at the maximum 80, at the maximum 70, at the maximum 60, at the maximum 50, at the maximum 40, at the maximum 30 or at the maximum 20 beacons.

List of groupings and resulting kits for the detection, enumeration and identification of the listed organisms is compiled in Table 1.

The beacons can be applied to assays designed to be performed in tubes, microtitre plates, filtered microtitre wells, slides and chips. The detection can be made with fluorescence, time resolved fluorescence, with a plurality of fluorophores and utilising electrochemical enzymes.

In the preferred embodiment for FISH the assay is performed on glass slides designed to hold and separate several samples.

Another subject of the present invention is a hybridisation method comprising (a) contacting at least one nucleic acid of any of the present invention or a combination of nucleic acids of the present invention with a biological sample, (b) hybridising the nucleic acid or the combination of nucleic acid of (a) with the sample under conditions where the stem of the nucleic is open, e.g. hybridising with a buffer which is essentially free of $Mg^{2+}$, and (c) inducing conditions which allow for stem formation in those nucleic acid molecules of (a) not forming a hybrid with the sample, e.g. washing with a Magnesium containing buffer, for instance at pH>8 or/and at room temperature.

The sample may be any sample of biological origin, such as a clinical or food sample, suspected of comprising a nucleic acid to be detected by the beacon. The sample may be a sample comprising microorganisms, such as bacteria, yeasts and molds, in particular Gram positive or/and Gram negative bacteria.

Also employed in the hybridisation method of the present invention can be a kit or chip as described herein.

"Essentially free of $Mg^{2+}$" refers to a $Mg^{2+}$ concentration of less than 1 mM, preferably less than 0.1 mM, more preferably less than 0.05 mM, most preferably less than 0.01 mM.

The buffer in step (c) may contain about 1 to about 20 mM $Mg^{2+}$, more particular about 5 to about 15 mM $Mg^{2+}$, even more particular about 8 to about 12 mM $Mg^{2+}$, most particular about 10 mM $Mg^{2+}$.

Any suitable hybridisation protocol comprising application of an essentially $Mg^{2+}$ free solution and a $Mg^{2+}$ containing solution as indicated above may be applied. For instance, the following protocol may be used: Aliquots of clinical samples are applied to defined fields on the slides. Preferably a defined quantity of 10 µl is applied and dried.

1. The samples are the heat fixed to the slides.
2. Gram positive organisms are subjected to a Lysozyme/Lysostaphin digestion following well published specifications. In a preferred embodiment the digestion is run for 7 minutes at 46° C. in a humidified chamber.
3. Pores are then formed for instance by immersing the slide 100% methanol or ethanol for several minutes. In a preferred embodiment the methanol or ethanol is ice cold and the immersion time is 7 minutes for Gram negative organisms and 3 minutes for Gram positive organisms.
4. The slide is then dried on a slide warmer, for instance at 55° C.
5. The beacons are dissolved in a hybridisation buffer (which may be essentially free of $Mg^{2+}$) and then applied to each field of the slide while on the slide warmer.
6. The slide is placed in a hybridisation chamber, humidified with hybridisation buffer. In a preferred embodiment the slide is covered with a hydrophobic cover slip and placed on a covered slide warmer at 46° C. for 12 minutes.
7. The slide is then washed with a Magnesium containing buffer, for instance at pH>8 or/and at room temperature. The buffer main contain about 1 to about 20 mM $Mg^{2+}$, more particular about 5 to about 15 mM $Mg^{2+}$, even more particular about 8 to about 12 mM $Mg^{2+}$, most particular 10 mM $Mg^{2+}$
8. The slide is then dried and may be mounted with mounting fluid and can be read under an epifluorescence microscope at a total magnification of for instance 400×, 600×, or 1000×.

Should other vessels be used for the hybridisation, the detection may be via flow-cytometry or automated fluorescence reader well known in the art.

Yet another embodiment of the present invention relates to Chip applications of the beacons of the present invention. For Chip applications the beacons need to be covalently attached to a carrier surface. To facilitate this, the 3'-terminal base of the designed beacons may be either biotinylated or linked via a hetero-bifunctional reagent to an enzyme using methods well known in the art of protein and nucleic acid chemistry. Biotinylated beacons may then be added to Streptavidin coated chips as can be obtained freely from commercial sources (19). In this application the respective biotinylated hairpin loops can be attached to plurality of distinct fields of one chip, for instance at least 10, at least 50, at least 100, at least 200, or at least 500 fields, or at the maximum 500, at the maximum 400 or at the maximum 300 fields. Total RNA can be extracted from samples using commercially available kits (20) and can be applied to the chip under hybridising conditions. After hybridisation the chip can be briefly washed with a magnesium containing buffer, for instance at pH>8. Fluorescence on a field marks the presence of specific target sequence, for instance a specific RNA indicating the presence of a respective organism in the sample.

In order to open hybridisation assays to large scale routine applications it is necessary to analyse a plurality of samples sequentially on one reusable chip. The design of the chip must allow large scale production, efficient quality control and long shelf live.

In order to meet these specifications, in another embodiment of the present invention, a beacon of the present invention is covalently attached to an enzyme exerting a signal by catalysing a specific reaction. In particular, the enzyme may exert an electrochemical signal. Suitable enzymes comprise, but are not limited to tyrosinase, peroxidase, sulfite oxidase, alkaline phosphatase, glucose oxydase, guanine oxidase. In a preferred embodiment the enzyme is recombinantly derived from a genomic sequence of a thermo- or hyperthermophylic organism to render it stable under hybridisation conditions and elevated temperatures (21). The enzyme may be attached to the beacon at one end of the beacon molecule. At the other end of the molecule, an inhibitor may be attached which is capable of inhibiting the enzyme activity. When no cognate sequence to said hairpin loops is present the inhibitor inhibits the enzyme and no signal is generated. In the presence of a cognate sequence the loop will remain unfolded with the inhibitor well removed from the enzyme and the enzyme will produce an electrochemical signal which can be detected by devices well described in the art. A linker may be employed for the attachment of the enzyme or/and the inhibitor, in particular for the attachment of the inhibitor.

In a further preferred embodiment glucose oxidase is attached to one end of the said hairpin loops and a glucose oxidase inhibitor, such as an adenine nucleotide or adenine nucleotide analogue is attached to the other end of the hairpin loop. Adenine nucleotides are known inhibitors of glucose oxidase (22, 23). A linker may be employed for the attachment of the glucose oxidase or/and the glucose oxidase inhibitor, in particular for the attachment of the glucose oxidase inhibitor. When no cognate sequence to said hairpin loops is present the inhibitor, in particular the adenine nucleotide inhibits the enzyme and no signal is generated. In the presence of a cognate sequence the loop will remain unfolded with the inhibitor well removed from the enzyme and the enzyme will produce an electrochemical signal which can be detected by devices well described in the art.

To perform such an assay a large plurality of sequences with identical characteristics (Table I) have been developed, which may be applied to defined positions on the detecting device (chip) respectively. Total RNA is extracted from a sample utilising extraction procedure and kits readily available on the market (20) and placed on the chip under hybridisation conditions. After the hybridisation the chip is washed with substrate buffer at 46° C. and the signal is read. At the end of the cycle all hybridised RNA is washed off with hybridisation buffer at elevated temperature. Preferably the wash temperature is chosen 10° C. above the respective $T_m$. In a preferred embodiment the chip is washed at 60° C. with hybridisation buffer. The temperature may then dropped to 46° C. to equilibrate for the next analytical cycle.

LEGENDS

Table 1 describes beacon sequences of the present invention. Abbreviations: R&G: a red or/and a green fluorescent dye may be attached to the beacon, such as Cy3 or FITC or a derivative thereof.

Table 2 describes that PNA beacons are not suitable in the present invention. Calculations were performed with the sequences of Table 1 assuming the beacon to be a PNA beacon. In contrast to DNA beacons, all of the following five criteria have to be fulfilled: GC content<60%, <3 bases self-complementary, 4 purines in a row, length of maximal 18, inverse sequence palindromes or repeats or hairpins. "Yes" ("No") in Table 2 indicates that the criterion is fulfilled (not fulfilled). The column "Final" indicates if a PNA beacon is suitable in the present invention ("Yes") or not ("No"). "No" in final indicates that one of the five criteria is not met. "Yes" would indicate that all criteria are met. All sequences of Table 2 are judged to be "No". Thus, no one of the sequences of Table 1 would be suitable in a PNA beacon.

REFERENCES

1. Sebastian Behrens, Caroline Ruhland, João Inácio, Harald Huber, A. Fonseca, I. Spencer-Martins, Bernhard M. Fuchs, and Rudolf Amann, In Situ Accessibility of Small-Subunit rRNA of Members of the Domains Bacteria, Archaea, and Eucarya to Cy3-Labeled Oligonucleotide or nucleotide analogue Probes, Applied and Environmental Microbiology, March 2003, p. 1748-1758, Vol. 69, No. 3
2. Wallace, R. B.; Shaffer, J.; Murphy, R. F.; Bonner, J.; Hirose, T.; Itakura, K. Nucleic Acids Res. 6, 3543 (1979).
3. Howley, P. M; Israel, M. F.; Iaw, M-F.; Martin, M. A. J. Biol. Chem. 254, 4876.

The equations for RNA are:

$$Tm=79.8+18.5 \log M+58.4(XG+XC)+11.8(XG+XC)2-820/L-0.35F$$

And for DNA-RNA hybrids:

$$Tm=79.8+18.5 \log M+58.4(XG+XC)+11.8(XG+XC)2-820/L-0.50F$$

4. Breslauer, K. J.; Frank, R.; Blšker, H.; Marky, L. A. Proc. Natl. Acad. Sci. USA 83, 3746-3750 (1986). For RNA see: Freier, S. M.; Kierzek, R.; Jaeger, J. A.; Sugimoto, N.; Caruthers, M. H.; Neilson, T.; Turner, D. H. Proc. Natl. Acad. Sci. 83, 9373-9377 (1986).
5. Rychlik, W.; Spencer, W. J.; Rhoads, R. E. (1990) Nucl. Acids Res. 18 (21), 6409-6412.
6. Owczarzy R., You Y., Moreira B. G., Manthey J. A., Huang L., Behlke M. A., Walder J. A. (2004) Effects of Sodium Ions on DNA Duplex Oligomers: Improved Predictions of Melting Temperatures, Biochemistry, 43:3537-3554.
7. Sebastian Behrens,[1] Bernhard M. Fuchs,[1] Florian Mueller,[2] and Rudolf Amann[1] Appl Environ Microbiol. 2003 August; 69(8): 4935-4941.
8. HYBRIDIZATION PROBES FOR NUCLEIC ACID DETECTION—UNIVERSAL STEMS document view Patent number: CA2176266 Publication date: 1996 Nov. 13,/EP0745690 (A2)
9. Tyagi, S., D. P. Bratu, and F. R. Kramer. 1998. Multicolor molecular beacons for allele discrimination. Nat. Biotechnol. 16:49-53.
10. Tyagi, S., and F. R. Kramer. 1996. Molecular beacons: probes that fluoresce upon hybridization. Nat. Biotechnol. 14:303-308.
11. Schofield, P., A. N. Pell, and D. O. Krause. 1997. Molecular beacons: trial of a fluorescence-based solution hybridization technique for ecological studies with ruminal bacteria. Appl. Environ. Microbiol. 63:1143-1147.
12. www.molecular-beacons.org
13. Molecular Beacons: Trial of a Fluorescence-Based Solution by Hybridization Technique for Ecological Studies with Ruminal Bacteria PETER SCHOFIELD, ALICE N. PELL, *AND DENIS O. KRAUSE† APPLIED AND ENVIRONMENTAL MICROBIOLOGY, March 1997, p. 1143-1147
14. Steven Park, May Wong, Salvatore A. E. Marras, Emily W. Cross, Timothy E. Kiehn, Vishnu Chaturvedi, Sanjay Tyagi, and David S. Perlin Journal of Clinical Microbiology, August 2000, p. 2829-2836, Vol. 38, No. 8; Rapid Identification of *Candida dubliniensis* Using a Species-Specific Molecular Beacon
15. Chuanwu Xi, Michal Balberg, Stephen A. Boppart, and Lutgarde Raskin APPLIED AND ENVIRONMENTAL MICROBIOLOGY, September 2003, p. 5673-5678 Vol. 69, No. 9 Use of DNA and Peptide Nucleic Acid Molecular Beacons for Detection and Quantification of rRNA in Solution and in Whole Cells
16. Guidelines for Sequence Design of PNA Oligomers wvvw.appliedbiosystems.com/support/seqguide.cfm
17. Tijssen, P. Hybridization with nucleic acid probes. part I. Theory and nucleic acid preparation, p. 268. Elsevier Science Publishers B.V., Amsterdam.
18. Nanogen, www.nanogen.com
19. Qiagene, www.Qiagene.com
20. Microbiology and Molecular Biology Reviews, March 2001, p. 1-43, Vol. 65, No. 1 Hyperthermophilic Enzymes: Sources, Uses, and Molecular Mechanisms for Thermostability, Claire Vieille and Gregory J. Zeikus
21. ELECTROCHEMICAL SENSORS FOR ENVIRONMENTAL MONITORING: A REVIEW OF RECENT TECHNOLOGY by JOSEPH WANG Department of Chemistry and Biochemistry, New Mexico State University Las Cruces, N. Mex. 88003
22. Brenda, www.brenda.uni-koeln.de

TABLE I

| Loop Diagostics Code number | Target organism | Beacon name | RNA | Position on rRNA (Ecoli) | Fuchs score 1 = high; VI = no/low signal |
|---|---|---|---|---|---|
| L-01-1 -10 -50 -100 | R&G Acinetobacter | B-Acibact-1 | 16S rRNA | 652-669 | 650-667 V |
| L-01-2 -10 -50 -100 | R&G Acinatobacter baumanii | B-Acinbaum-2 | 16S rRNA | 67-86 | 66-83 = II |
| L-01-3 -10 -50 -100 | R&G Actinomyces spp. | | | | |
| L-01-4 -10 -50 -100 | R&G Aspergillus spp | | | | |
| L-01-5 -10 -50 -100 | Aspergillus flavus | Aspfla | 18s | NA | NA |
| L-01-6 -10 -50 -100 | Aspergillus fumigatus | Aspfum | 18s | NA | NA |
| L-01-7 -10 -50 -100 | Aspergillus niger | Aspnig | 18s | NA | NA |
| L-01-8 -10 -50 -100 | Aspergillus terreus | Aspter | 18s | NA | NA |
| L-01-9 -10 -50 -100 | R&G Bacteroides/Prevotella | B-BacPrev | 16S rRNA | | |
| L-01-10 -10 -50 -100 | R&G Borrelia burgdorferi | B-Borrburg | 16S rRNA | 39-58 | 38-54 = II; 48-65 = II |
| L-01-11 -10 -50 -100 | R&G Bordetella pertussis | B-Borper | 23S rRNA | 1768-1785 | 1768-1786 = IV |
| L-01-12 -10 -50 -100 | R&G Burkholderia cepacia complex = Option I | B-Burcep-complex-1 | 16S | 425-449 | 431-448 = III |

TABLE I-continued

| | | | | | | |
|---|---|---|---|---|---|---|
| L-01-13 | -10<br>-50<br>-100 | R&G *Burkholderia cepacia* complex, two beacons = Option II | B-Burcep-complex-2a | 16S | 404-383 | 387-403 = IV |
| L- | | | B-Burcep-compl-2b | 16S | 446-433 | 431-448 = III |
| L-01-14 | -10<br>-50<br>-100 | R&G *Burkholderia cepacia* | B-Burcep-pure | 16S | 441-460 | 440-456 = I |
| L-01-15 | -10<br>-50<br>-100 | R&G *Burkholderia pyrrocinia/stabilis/ambifaria* | B-Burstabpyramb | 16S | 407-424 | 413-429 = II |
| L-01-16 | -10<br>-50<br>-100 | R&G *Burkholderia dolosa/anthina* | B-Burdolant | 16S | 474-458 | 443-460 = II |
| L-01-17 | -10<br>-50<br>-100 | R&G *Burkholderia multivorans* | B-Burmult | 16S | 475-463 | 455-473 = VI |
| L-01-18 | -10 | R&G *Burkholderia cenocepacia/vietnamiensis* | B-Bur-vietceno | 16S | 475-458 | 455-473 = VI |
| L-01-19 | -10<br>-50<br>-100 | R&G *Campylobacter* (pathogenic *thermophiles* | Ctherm | 23S | 1419 | |
| L-01-20 | -10<br>-50<br>-100 | R&G *Campylobacter lari* | Clari | 16S rRNA | | |
| L-01-21 | -10<br>-50<br>-100 | R&G *Campylobacter jejuni* | Cpjej | | | |
| L-01-22 | -10<br>-50<br>-100 | R&G Cp. *upsaliensis* | Cpups | | | |
| L-01-23 | -10<br>-50<br>-100 | R&G Cp *coli* | Cpcoli | | | |
| L-01-24 | -10<br>-50<br>-100 | R&G Cp *coli*-comp | Cpcolicomp | | | |
| L-01-25 | -10<br>-50<br>-100 | R&G *Chlamydia* | S-G-Chla-0232-A-18 | | | |

TABLE I-continued

| | | | | | | |
|---|---|---|---|---|---|---|
| L-01-26 | -10<br>-50<br>-100 | R&G Chlamydiaceae | S-F-Chlae-0574-a-A-18 | | | |
| L-01-27 | -10<br>-50<br>-100 | R&G Chlamydiales | S-O-Chls-0523-a-A-18b | | | |
| L-01-28 | -10<br>-50<br>-100 | R&G *Chlamydophila* | S-G-Chlph-0583-a-A-18 | | | |
| L-01-29 | -10<br>-50<br>-100 | R&G *Chlamydia pneumoniae* | B-Chlapneu | 16S rRNA | | |
| L-01-36 | -10<br>-50<br>-100 | R&G "*Chlamydia psittaci*" group | S-S-Cps-1414-a-A-18 | | | |
| L-01-31 | -10<br>-50<br>-100 | R&G Subgroup of the Parachlamydiaceae | Bn9658 | | | |
| L-01-32 | -10<br>-50<br>-100 | R&G *Chlamydia* ssp. | ChlamyA | | | |
| L-01-33 | -10<br>-50<br>-100 | R&G *Chlamydia trachomatis* | ChltraA | | | |
| L-01-34 | -10<br>-50<br>-100 | R&G *Canda albicans* | Can-alb-2 | 18S | 314-295 | NA |
| L-01-35 | -10<br>-50<br>-100 | R&G *Canda krusei* | Cankru-2 | 18S | 146-169 | NA |
| L-01-36 | -10<br>-50<br>-100 | R&G *Candida dubliniensis* | Can-dub-2 | 18S | 187-206 | NA |
| L-01-37 | -10<br>-50<br>-100 | R&G *Candida glabrata* | Can-gla-2 | 18S | 379-363 | NA |
| L-01-38 | -10<br>-50<br>-100 | R&G *Candida parapsilosis* | Can-para-2 | 18S | 310-291 | NA |

TABLE I-continued

| | | | | | | |
|---|---|---|---|---|---|---|
| L-01-39 | -10<br>-50<br>-100 | R&G *Candida* spp | Can-spp-2 | 18S | 366-347 | NA |
| L-01-40 | -10<br>-50<br>-100 | R&G *Candida tropicales* | Can-trop-3 | 18S | 64-84 | NA |
| L-01-41 | -10<br>-50<br>-100 | *Candida lusitaniae* | | | | |
| L-01-42 | -10<br>-50<br>-100 | R&G *Citrobacter freundii* | B-cifreu | 23S rRNA | 542-559 | 547-564 = III |
| L-01-43 | -10<br>-50<br>-100 | R&G *Clostridium botulinum* | B-Clobot | 16S rRNA | 173-194 | 173-190IV, 181-198 = II |
| L-01-44 | -10<br>-50<br>-100 | *Clostridium difficile* | B-Clodiff | 16S rRNA | 73-51 | 38-54 = II; 55-72 = III |
| L-01-45 | -10<br>-50<br>-100 | R&G *Clostridium* spp | B-Clospp | 16S rRNA | 52-35 | 48-65 = II; 38-54 = II |
| L-01-46 | -10<br>-50<br>-100 | R&G *Clostridium perfringens* | B-Cloper-Cp2-10 | 16S rRNA | 212-189 | 199-215 = II |
| L-01-47 | -10<br>-50<br>-100 | R&G *Clostridium perfringens* | B-Cloper-Cp2-18 | 16S rRNA | | |
| L-01-48 | -10<br>-50<br>-100 | *Clostridium tetani* | B-Clotet | 16S rRNA | 114-95 | 91-108 = II; 102-118 = III |
| L-01-49 | -10<br>-50<br>-100 | *Cryptococcus neoformans* | | | | |
| L-01-50 | -10<br>-50<br>-100 | R&G Enterobacteriaceae | B-EBAC-1791 | 23S rRNA | 1811-1791 | 1787-1804 = III |
| L-01-51 | -10<br>-50<br>-100 | R&G Enterobacteriaceae | B-Entero-1247 | 16S rRNA | 1264-1247 | 1248-1265 = III |

TABLE I-continued

| | | | | | Sbjct: 201-182 | 199-215 = II |
|---|---|---|---|---|---|---|
| L-01-52 | -10<br>-50<br>-100 | R&G Enterobacteriaceae | B-Entero + 182 | 16S rRNA | | |
| L-01-53 | -10<br>-50<br>-100 | R&G Enterococci | B-Entcoc | 16S rRNA | 242-225 | 218-235 = I; 236-252 = II |
| L-01-54 | -10<br>-50<br>-100 | R&G Enterococcus faecalis | B-Ent-alis | 16S rRNA | 129-146 | 127-144 = III |
| L-01-55 | -10<br>-50<br>-100 | R&G Enterococcus faecium | B-Ent-ium | 16S rRNA | 192-212 | 191-209 = II |
| L-01-56 | -10<br>-50<br>-100 | R&G Escherichia coli | B-Ecol-On 1 | 16S rRNA | 75-95 | 66-83 = II;<br>73-90 = IV |
| L-01-57 | -10<br>-50<br>-100 | R&G Eu-bacteria | Eub | | | |
| L-01-58 | -10<br>-50<br>-100 | R&G Fusarium spp | | | | |
| L-01-59 | -10<br>-50<br>-100 | R&G Gardnerella vaginalis | Garvag | | | |
| L-01-60 | -10<br>-50<br>-100 | R&G Haemophilus influenzae | B-Haeinf-2 | 16S rRNA | 189-167 | 173-190 = IV;<br>181-198 = II |
| L-01-61 | -10<br>-50<br>-100 | R&G Haemophilus influenzae | B-Haeinf-3 | 16S rRNA | 183-162 | 163-180 = IV |
| L-01-62 | -10<br>-50<br>-100 | R&G Klebsiella pneumoniae | b-Klepne-2 | 16S rRNA | 445-465 | 443*460 = II |
| L-01-63 | -10<br>-50<br>-100 | R&G Klebsiella oxytoca | B-Kleboxy | 16S rRNA | 467-444 | 446-463 = II |
| L-01-64 | -10<br>-50<br>-100 | R&G Lactobacillus brevis | B-Lacbrev | 16S rRNA | 84-63 | 63-80 = II |

TABLE I-continued

| | | | | | | |
|---|---|---|---|---|---|---|
| L-01-65 | -10 | R&G *Mycobacterium avium* | | | | |
| | -50 | | | | | |
| | -100 | | | | | |
| L-01-66 | -10 | R&G *Mycobacterium bovis* | | | | |
| | -50 | | | | | |
| | -100 | | | | | |
| L-01-67 | -10 | R&G *Mycobacterium chelonae* | | | | |
| | -50 | | | | | |
| | -100 | | | | | |
| L-01-68 | -10 | R&G *Mycobacterium fortuitum* | | | | |
| | -50 | | | | | |
| | -100 | | | | | |
| L-01-69 | -10 | R&G *Mycobacterium gordonae* | | | | |
| | -50 | | | | | |
| | -100 | | | | | |
| L-01-70 | -10 | R&G *Mycobacterium intracellulare* | | | | |
| | -50 | | | | | |
| | -100 | | | | | |
| L-01-71 | -10 | R&G *Mycobacterium kansasii* | | | | |
| | -50 | | | | | |
| | -100 | | | | | |
| L-01-72 | -10 | R&G *Mycobacterium malmoense* | | | | |
| | -50 | | | | | |
| | -100 | | | | | |
| L-01-73 | -10 | R&G *Mycobacterium smegmatis* | | | | |
| | -50 | | | | | |
| | -100 | | | | | |
| L-01-74 | -10 | R&G *Mycobacterium tuberculosis* | | | | |
| | -50 | | | | | |
| | -100 | | | | | |
| L-01-75 | -10 | R&G *Mycobacterium xenopi* | | | | |
| | -50 | | | | | |
| | -100 | | | | | |
| L-01-76 | -10 | R&G *Legionella pneumophila* | B-Legpne | 16S rRNA | 633-616 | 614-631 = IV |
| | -50 | | | | | |
| | -100 | | | | | |
| L-01-77 | -10 | R&G *Listeria monocytogenes* | Lismon | | | |
| | -50 | | | | | |
| | -100 | | | | | |

TABLE I-continued

| | | | | | | |
|---|---|---|---|---|---|---|
| L-01-78 | -10<br>-50<br>-100 | R&G Mycoplasma hominis | Mychom | | | |
| L-01-79 | | R&G Nocardia spp. | | | | |
| L-01-80 | -10<br>-50<br>-100 | R&G Proteus mirabili/vulgaris | B-Protmivi | 23S rRNA | 1835-1818 | 1823-1839 = III |
| L-01-81 | -10<br>-50<br>-100 | R&G Pneumocystis-1 | Pcp-1 | 18S | 1155 | |
| L-01-82 | -10<br>-50<br>-100 | R&G Pneumocystis-2 | Pcp-2 | 18S | 845 | |
| L-01-83 | | R&G Propionibacterium acnes | | | | |
| L-01-84 | | R&G Propionibacterium spp (other than Psaer) | | | | |
| L-01-85 | -10<br>-50<br>-100 | R&G Pseudomonas aeruginosa | B-Psaer C | 23S rRNA | 1526-1508 | 1509-1526 = III |
| L-01-86 | -10<br>-50<br>-100 | R&G Pseudomonas spp | Psspp | 16S rRNA | 79-59 | 60-077 = II |
| L-01-87 | -10<br>-50<br>-100 | R&G Salmonellen | Sal 23S 331 | 23S rRNA | | |
| L-01-88 | -10<br>-50<br>-100 | R&G Salmonellen 331 Komp | Komp Sal 23S 331 | 23S rRNA | | |
| L-01-89 | -10<br>-50<br>-100 | R&G Salmonellen | Sal 23S 1705 | 23S rRNA | | |
| L-01-90 | -10<br>-50<br>-100 | R&G Salmonellen | Sal 23S 1705 Komp | 23S rRNA | | |
| L-01-91 | -10<br>-50<br>-100 | R&G Salmonellen | Sal 23S 544 | 23S rRNA | | |

TABLE I-continued

| | | | | | |
|---|---|---|---|---|---|
| L-01-92 | -10<br>-50<br>-100 | R&G Salmonella | B-Sal 1686 | 23S rRNA | 1705-1686 | 1696-1713 = I;<br>1678-1695 = III |
| L-01-93 | -10<br>-50<br>-100 | R&G Serratia spp | | | | |
| L-01-94 | -10<br>-50<br>-100 | R&G Serratia marcescens | B-Sermarc | 16S rRNA | 637-656 | 639-656 = VI |
| L-01-95 | -10<br>-50<br>-100 | R&G Staphylococcus aureus | B-Staphau | 16S rRNA | 75-52; | 55-72 = III |
| L-01-96 | -10<br>-50<br>-100 | R&G Staphylococci | B-Staphspp-2 | 16S rRNA | 769-751 | 756-773 = IV |
| L-01-97 | -10<br>-50<br>-100 | R&G Stenotrophomonas maltofilia | Stemal-2 | 16S rRNA | 592-612 | 614-631 = IV |
| L-01-98 | -10<br>-50<br>-100 | R&G Streptococcus agalactiae | B-Straga-2 | 16S rRNA | 416-396 | 396-412 = IV |
| L-01-99 | -10<br>-50<br>-100 | R&G Streptococci | B-Strept-2 | 16S rRNA | 459-439 | 440-456 = I |
| L-01-100 | -10<br>-50<br>-100 | R&G Streptococcus pneumoniae | B-Strepne-2 | 16S rRNA | 202-178 | 181-198 = II |
| L-01-101 | -10<br>-50<br>-100 | R&G Streptococcus pyogenes | B-Strpyo-C | 16S rRNA | 196-217 | 199-215 = II |
| L-01-102 | -10<br>-50<br>-100 | R&G Ureaplasma urealyticum | Ureure | | | |
| L-01-103 | -10<br>-50<br>-100 | R&G Urogenital-Peptostreptococci | Pepure | | | |
| L-01-104 | -10<br>-50<br>-100 | R&G Yersinia enterocolitica | Yerent | | | |

TABLE I-continued

| Loop Diagnostics Code number | | SEQ. ID. NO: | Sequence 5'-3' | | Length | AT Content | GC content | delta Gs target: -21 +/- 2 kcal/mol |
|---|---|---|---|---|---|---|---|---|
| L-01-1 | -10 Beacon | 1 | TGCCGGATT ACC ATC CTC TCC CAT ACT CTA AATCCGGCA | Probe/target | 21 | 11 | 10 | 48% | ΔG = -21.9 |
| | -50 Probe | 2 | ACC ATC CTC TCC CAT ACT CTA | Hybrid | 39 | | | 54% | ΔG = -0.48 |
| | -100 Target | 3 | TAG AGT ATG GGA GAG GAT GGT | Beacon | | | | | |
| L-01-2 | -10 Beacon | 4 | GCGCG TC CGG TAG CAA GCT ACC TTC CGCGC | Probe/target | 20 | 9 | 11 | 55% | ΔG = -22.1 |
| | -50 Probe | 5 | TC CGG TAG CAA GCT ACC TTC | Hybrid | 30 | 9 | 21 | 70% | ΔG = -0.94 |
| | -100 Target | 6 | GAA GGT AGC TTG CTA CCG GA | Beacon | | | | | |
| L-01-3 | -10 | | | | | | | | |
| | -50 | | | | | | | | |
| | -100 | | | | | | | | |
| L-01-4 | -10 | | | | | | | | |
| | -50 | | | | | | | | |
| | -100 | | | | | | | | |
| L-01-5 | -10 Beacon | 7 | CCCCCGGCGT AC AGA GTT CGT GGT GTC TCC TCGCCCAGCGG | Probe/target | 20 | 9 | 11 | 55% | ΔG = -21.5 |
| | -50 Probe | 8 | AC AGA GTT CGT GGT GTC TCC | Hybrid | 41 | 12 | 29 | 71% | ΔG = -0.19 |
| | -100 Target | 9 | GGA GAC ACC ACG AAC TCT GT | Beacon | | | | | |
| L-01-6 | -10 Beacon | 10 | cgtc gcc tac aga gca ggt gac g | Probe/target | 18 | 7 | 11 | 61% | ΔG = -20.6 |
| | -50 Probe | 11 | gcc tac aga gca ggt gac | Hybrid | 23 | 8 | 15 | 65% | ΔG = -0.86 |
| | -100 Target | 12 | gtc acc tgc tct gta ggc | Beacon | | | | | |
| L-01-7 | -10 Beacon | 13 | ctctga a ctg att gca ttc aat caa ctc agag | Probe/target | 25 | 16 | 9 | 36% | ΔG = -21.4 |
| | -50 Probe | 14 | a ctg att gca ttc aat caa ctc aga | Hybrid | 32 | 19 | 13 | 41% | ΔG = -0.18 |
| | -100 Target | 15 | tct gag ttg att gaa tgc aat cag t | Beacon | | | | | |
| L-01-8 | -10 Beacon | 16 | TCCGTC tga ttg caa aga atc aca ctc aga GACGGA | Probe/target | 24 | 15 | 9 | 38% | ΔG = -20.9 |
| | -50 Probe | 17 | tga ttg caa aga atc aca ctc aga | Hybrid | 36 | 19 | 17 | 47% | ΔG = -0.63 |
| | -100 Target | 18 | tct gag tgt gat tct ttg caa tca | Beacon | | | | | |
| L-01-9 | -10 Beacon | 19 | GCCCCGGCAT CCA ATG TGG GGG ACC TTC TAGCCCAGCGGC | Probe/target | 17 | 6 | 11 | 59% | ΔG = -20.1 |
| | -50 Probe | 20 | CCA ATG TGG GGG ACC TTC | Hybrid | 39 | | | 74% | ΔG = -0.70 |
| | -100 Target | 21 | GAA GGT CCC CCA CAT TGG | Beacon | | | | | |
| L-01-10 | -10 Beacon | 22 | TGCCGGATT CA TGC TTA AGA CGC ACT GCC AATCCGGCA | Probe/target | 20 | 9 | 11 | 50% | ΔG = -20.9 |
| | -50 Probe | 23 | CA TGC TTA AGA CGC ACT GCC | Hybrid | 39 | | | 56% | ΔG = -0.59 |
| | -100 Target | 24 | GGC AGT GCG TCT TAA GCA TG | Beacon | | | | | |

TABLE I-continued

| | | | | | | | | |
|---|---|---|---|---|---|---|---|---|
| L-01-11 | -10 | Beacon | TGCCGGATT CAG CAC TCT GCA AAG ACG AAA AATCCGGCA | 25 | 21 | 11 | 10 | 48% | ΔG = -20.5 |
| | -50 | Probe | CAG CAC TCT GCA AAG ACG AAA | 26 | 40 | | | 53% | ΔG = -0.48 |
| | -100 | Target | TTT CGT CTT TGC AGA GTG CTG | 27 | | | | | |
| L-01-12 | -10 | Beacon | ACCGCTC TTT CTT TCC GGA CAA AAG TGC TTT GAGCGGCT | 28 | 24 | 15 | 9 | 38% | ΔG = -20.9 |
| | -50 | probe sequence | TTT CTT TCC GGA CAA AAG TTT | 29 | 39 | | | 51% | ΔG = -0.92 |
| | -100 | Target | AAA GCA CTT TTG TCC GGA AAG AAA | 30 | | | | | |
| L-01-13 | -10 | Beacon | CGCCTTC AGA ACC AAG GAT TTC TTT CCG G GAAGGCG | 31 | 22 | 12 | 10 | 45% | ΔG = -20.5 |
| | -50 | probe sequence | AGA ACC AAG GAT TTC TTT CCG G | 32 | | | | 56% | ΔG = -1.07 |
| | -100 | Target | CCG GAA AGA AAT CCT TGG TTC T | 33 | 36 | | | | |
| L- | -10 | Beacon | ACGCA AGAGCCAAGGTTTCTTCCG CTTGCGT | 34 | 21 | 11 | 10 | 48% | ΔG = -20.2 |
| | -50 | probe sequence | AGA GCC AAG GTT TTC TTT CCG | 35 | 34 | | | 50% | ΔG = -1.05 |
| | -100 | Target | CGG AAA GAA AAC CTT GGC TCT | 36 | | | | | |
| L-01-14 | -10 | Beacon | ACGCTC G TCA TCC CCC GGC CAT GAGCGT | 37 | 16 | 5 | 11 | 69% | ΔG = -20.1 |
| | -50 | probe sequence | G TCA TCC CCC GGC CAT | 38 | 28 | | | 68% | ΔG = -1.00 |
| | -100 | Target | ATG GCC GGG GGA TGA C | 39 | | | | | |
| L-01-15 | -10 | Beacon | CGCTC CGT CAT CCC CCG GCT ATA GGAGCG | 40 | 18 | 7 | 11 | 61% | ΔG = -20.6 |
| | -50 | probe sequence | CGT CAT CCC CCG GCT ATA | 41 | 29 | | | 69% | ΔG = -0.43 |
| | -100 | Target | TAT AGC CGG GGA TGA CG | 42 | | | | | |
| L-01-16 | -10 | Beacon | CCGCTC GT CAT CCC CCG GCT GTA GAGCGG | 43 | 17 | 6 | 11 | 65% | ΔG = -20.6 |
| | -50 | probe sequence | GT CAT CCC CCG GCT GTA | 44 | 29 | | | 72% | ΔG = -0.43 |
| | -100 | Target | TAC AGC CGG GGA ATG AC | 45 | | | | | |
| L-01-17 | -10 | Beacon | GCCCCGGCGT CGT CAT CCC CCG ATC GTA TCGCCCAGCGGC | 46 | 18 | 7 | 11 | 61% | ΔG = -20.0 |
| | -50 | probe sequence | CGT CAT CCC CCG ATC GTA | 47 | 41 | | | 73% | ΔG = -1.11 |
| | -100 | Target | TAC GAT CGG GGG ATG ACG | 48 | | | | | |
| L-01-18 | -10 | Beacon | GCCGCCGGCGT CGT CAT CCC CCG ACT GTA TCGCCCAGCGGC | 49 | 18 | 7 | 11 | 61% | ΔG = -20.3 |
| | -50 | probe sequence | CGT CAT CCC CCG ACT GTA | 50 | 41 | | | 76% | ΔG = -1.11 |
| | -100 | Target | TAC AGT CGG GGG ATG ACG | 51 | | | | | |

TABLE I-continued

| | | | | | | | |
|---|---|---|---|---|---|---|---|
| L-01-19 | -10<br>-50<br>-100 | Beacon<br>Probe<br>Target | | GCC CTA AGC GTC CTT CCA | 52 | | |
| L-01-20 | -10<br>-50<br>-100 | Beacon<br>Probe<br>Target | ACGCTC GAA GTG TAA GCA ACT AAA T<br>GAGCGT<br>GAA GTG TAA GCA ACT AAA T<br>A TTT AGT TGC TTA CAC TTC | | 53<br>54<br>55 | 19<br>31 | 13 | 6 | 32%<br>45% | -14<br>-0.78 |
| L-01-21 | -10<br>-50<br>-100 | Beacon<br>Probe<br>Target | ACGCTC AGC TAA CCA CTT ATA CCG<br>GAGCGT<br>AGC TAA CCA CTT ATA CCG<br>CGG TAT AAG TGG TTA GCT | | 56<br>57<br>58 | 18<br>30 | 10 | 8 | 44%<br>53% | -17.3<br>-0.67 |
| L-01-22 | -10<br>-50<br>-100 | Beacon<br>Probe<br>Target | CCCGCTC CGT GTG TCG CCC TAG GCG<br>TA GAGCGG<br>CGT GTG TCG CCC TAG GCG TA<br>TA CGC CTA GGG CGA CAC ACG | | 59<br>60<br>61 | 20<br>32 | 7 | 13 | 65%<br>72% | -25.4<br>-0.84 |
| L-01-23 | -10<br>-50<br>-100 | Beacon<br>Probe<br>Target | CCCGCTC TCG ATG GCA TCA GGG GTT<br>GAGCGG<br>TCG ATG GCA TCA GGG GTT<br>AAC CCC TGA TGC CAT CGA | | 62<br>63<br>64 | 18<br>30 | 8 | 10 | 56%<br>67% | -20.7<br>-0.82 |
| L-01-24 | -10<br>-50<br>-100 | Beacon<br>Probe<br>Target | not required, competitor is not labelled<br>TCG ACG GCA TCA GGG GTT<br>AAC CCC TGA TGC CGT CGA | | 65<br>66<br>67 | 18 | 7 | 11 | 61% | -22.0 |
| L-01-25 | -10<br>-50<br>-100 | Beacon<br>Probe<br>Target | ACGCCGGCGT TAG CTG ATA TCA CAT<br>AGA TCGCCCAGCGT<br>TAG CTG ATA TCA CAT AGA<br>TCT ATG TGA TAT CAG CTA | | 68<br>69<br>70 | 18<br>39 | 12 | 6 | 33%<br>59% | -14.4<br>-0.06 |
| L-01-26 | -10<br>-50<br>-100 | Beacon<br>Probe<br>Target | TCCGCCGGCGT CTT TCC GCC TAC ACG<br>CCC TCGCCCAGCGGA<br>CTT TCC GCC TAC ACG CCC<br>GGG CGT GTA GGC AAG | | 71<br>72<br>73 | 18<br>41 | 6 | 12 | 67%<br>73% | -22.0<br>-1.22 |
| L-01-27 | -10<br>-50<br>-100 | Beacon<br>Probe<br>Target | TCCCCCGGCGT CCT CCG TAT TAC CGC<br>AGC TCGCCCAGCGGA<br>CCT CCG TAT TAC CGC AGC<br>GCT GCG GTA ATA CGG AGG | | 74<br>75<br>76 | 18<br>41 | 7 | 11 | 61%<br>71% | -20.5<br>-1.22 |
| L-01-28 | -10<br>-50<br>-100 | Beacon<br>Probe<br>Target | ACGCCGGCGT CTA ACT TTC CTT TCC<br>GCC TCGCCCAGCGT<br>CTA ACT TTC CTT TCC GCC<br>GGC GGA AAG GAA AGT TAG | | 77<br>78<br>79 | 18<br>39 | 9 | 9 | 50%<br>64% | -17.3<br>-0.06 |

TABLE I-continued

| | | | | | | | |
|---|---|---|---|---|---|---|---|
| L-01-29 | -10 | Beacon | TCCACCGGCGT CTC TTC CTC AAC CGA AAG TCGCCCAGTGGA | 80 | | | |
| | -50 | Probe | CTC TTC CTC AAC CGA AAG | 81 | 18 | 9 | 50% -16.4 |
| | -100 | Target | CTT TCG GTT GAG GAA GAG | 82 | 41 | | 61% |
| L-01-30 | -10 | Beacon | TCAGCCGGCGT AAG GCA AAA CCA ACT CCC TCGCCCAGCTGA | 83 | | | |
| | -50 | Probe | AAG GCA AAA CCA ACT CCC | 84 | 18 | 9 | 50% -18.8 |
| | -100 | Target | GGG AGT TGG TTT TGC CTT | 85 | 41 | | 61% -0.02 |
| L-01-31 | -10 | Beacon | CCGCCGGCGT TCC GTT TTC TCC GCC TAC TCGCCCAGCGG | 86 | | | |
| | -50 | Probe | TCC GTT TTC TCC GCC TAC | 87 | 18 | 8 | 50% -19.7 |
| | -100 | Target | GTA GGC GGA GAA AAC GGA | 88 | 39 | | 69% -0.40 |
| L-01-32 | -10 | Beacon | TCCGCCGGCGT GCT CCC CTT GCT TTC GCG TCGCCCAGCGGA | 89 | | | |
| | -50 | Probe | GCT CCC CTT GCT TTC GCG | 90 | 18 | 6 | 61% -21.7 |
| | -100 | Target | CGC GAA AGC AAG GGG AGC | 91 | 42 | | 69% -1.22 |
| L-01-33 | -10 | Beacon | ACGCTC TCG GAT GCC CAA ATA TCG GAGCGT | 92 | | | |
| | -50 | Probe | TCG GAT GCC CAA ATA TCG | 93 | 18 | 9 | 50% -18.4 |
| | -100 | Target | CGA TAT TTG GGC ATC CGA | 94 | 30 | | 57% -0.44 |
| L-01-34 | -10 | Beacon | GG aa tgg cta ccc aga ggg aaa CCATTCC | 95 | 20 | 11 | 45% ΔG = -19.7 |
| | -50 | probe sequence | aa tgg cta ccc aga agg aaa | 96 | 29 | 15 | 52% ΔG = -0.57 |
| | -100 | Target | ttt cct tct ggg tag cca tt | 97 | | | |
| L-01-35 | -10 | Beacon | CCGCTC tgt att agc tct aga ttt cca cgg GAGCGG | 98 | 24 | 15 | 38% ΔG = -21.9 |
| | -50 | probe sequence | tgt att agc tct aga ttt cca cgg | 99 | 36 | 19 | 53% ΔG = -0.56 |
| | -100 | Target | ccg tgg aaa tct aga gct aat aca | 100 | | | |
| L-01-36 | -10 | Beacon | GTTTGcc ccg aaa gag taa ctt gca GGCAAAC | 101 | 20 | 10 | 50% ΔG = -19.8 |
| | -50 | probe sequence | cc ccg aaa gag taa ctt gca | 102 | 32 | 16 | 50% ΔG = -0.55 |
| | -100 | Target | tgc aag tta ctc ttt cgg gg | 103 | | | |
| L-01-37 | -10 | Beacon | GCCCCGGCGT gg cca ccc agg ccc aaa TCGCCCAGCGGC | 104 | 17 | 5 | 71% ΔG = -22.5 |
| | -50 | probe sequence | gg cca ccc agg ccc aaa | 105 | 40 | 32 | 80% ΔG = -2.30 |
| | -100 | Target | ttt ggg cct ggg tgg cc | 106 | | | |

TABLE I-continued

| ID | | | Type | Sequence | | | | |
|---|---|---|---|---|---|---|---|---|
| L-01-38 | -10 | Beacon | | GCCGCCGGCGT gc caa aaa ggc tag cca gaa TCGCCCAGCGGC | 107 | | | |
| | -50 | probe sequence | Beacon | gc caa aaa ggc tag cca gaa | 108 | 20 | 10 | 10 | 50% | ΔG = -20.9 |
| | -100 | Target | | ttc tgg cta gcc ttt ttg gc | 109 | 43 | | 30 | 70% | ΔG = -1.76 |
| L-01-39 | -10 | Beacon | | ACGC gct tgg ctg gcc ggt c GCGT | 110 | 16 | 4 | 12 | 75% | ΔG = -21.1 |
| | -50 | probe sequence | | g acc ggc cag agc | 111 | | | | | |
| | -100 | Target | | gct tgg ctg gcc ggt c | 112 | 24 | | 18 | 75% | ΔG = -0.90 |
| L-01-40 | -10 | Beacon | | ACCGCCGGCGT tac gca tca gaa aga tgg acc TCGCCCAGCGGT | 113 | 21 | 11 | 10 | 48% | ΔG = -20.7 |
| | -50 | probe sequence | | tac gca tca gaa aga tgg acc | 114 | 44 | | 28 | 64% | ΔG = -1.03 |
| | -100 | Target | | GGT CCA TCT TTC TGA TGC GTA | 115 | | | | | |
| L-01-41 | -10 -50 -100 | | | | | | | | |
| L-01-42 | -10 | Beacon | | TGCCGGATT CTAC TTG TTA GGT GAC TGC GT AATCCCGGCA | 116 | 21 | 10 | 11 | 48% | ΔG = -20.4 |
| | -50 | Probe | | C TAC TTG TTA GGT GAC TGC GT | 117 | 40 | | | 53% | ΔG = -0.48 |
| | -100 | Target | | AC GCA GTC ACC TAA CAA GTA G | 118 | | | | | |
| L-01-43 | -10 | Beacon | | TCTTG TAG T GC CGT TTC ATG CGA AAC TAC AA GA | 119 | 22 | 12 | 10 | 45% | ΔG = -20.7 |
| | -50 | Probe | | GC CGT TTC ATG CGA AAC TAC AA | 120 | 33 | | | 42% | ΔG = -0.79 |
| | -100 | Target | | TT GTA GTT TCG CAT GAA ACG GC | 121 | | | | | |
| L-01-44 | -10 | Beacon | | CGCTCA CAC CCG TCC GCC GCT AAT GAGCG | 122 | 23 | 13 | 10 | 43% | ΔG = -20.8 |
| | -50 | Probe | | CAA CTT GCA TCGCCCAGCGGC CGA AGT AAA TCG CTC AAC TTG CA | 123 | 46 | | 30 | 65% | ΔG = -1.33 |
| | -100 | Target | | TGC AAG TTG AGC GAT TTA CTT CG | 124 | | | | | |
| L-01-45 | -10 | Beacon | | CGCTCA CAC CCG TCC GCC GCT AAT GAGCG | 125 | 18 | 6 | 12 | 67% | ΔG = -22.0 |
| | -50 | Probe | | CAC CCG TCC GCC GCT AAT | 126 | 29 | | | 69% | ΔG = -0.39 |
| | -100 | Target | | ATT AGC GGC GGA CGG GTG | 127 | | | | | |
| L-01-46 | -10 | Beacon | | GCCGCCGGCGT G ATT GCT CCT TTG GTT GAA TGA TG TCGCCCAGCGGC | 128 | 21 | 11 | 10 | 48% | ΔG = -20.9 |
| | -50 | probe | | G ATT GCT CCT TTG GTT GAA TGA TG | 129 | 44 | | | 68% | ΔG = -1.22 |
| | -100 | Target | | CA TCA TTC AAC CAA AGG AGC AAT C | 130 | | | | | |
| L-01-47 | -10 | Beacon | | ACGCTC GGT TGA ATG ATG ATG CCA T GAGCGT | 131 | 19 | 10 | 9 | 42% | ΔG = -21.2 |
| | -50 | probe | | GGT TGA ATG ATG ATG CCA TCT TT | 132 | 31 | | | 52% | ΔG = -0.16 |
| | -100 | Target | | AA AGA TGG CAT CAT CAT TCA ACC | 133 | | | | | |

TABLE I-continued

| | | | | | | | |
|---|---|---|---|---|---|---|---|
| L-01-48 | -10 | Beacon | GCGGAC CT GTG TTA CTC ACC CGT CCG C | 134 | | | |
| | -50 | probe | CT GTG TTA CTC ACC CGT CCG | 135 | | | |
| | -100 | Target | CGG ACG GGT GAG TAA CAC AG | 136 | | | |
| | | Probe/target Hybrid | | | 20 | 8 | 42% | ΔG = -21.6 |
| | | Beacon | | | 27 | 18 | 52% | ΔG = -1.15 |
| L-01-49 | -10 | | | | | | |
| | -50 | | | | | | |
| | -100 | | | | | | |
| L-01-50 | -10 | Beacon | TGCCGGATT TT CGT GTT TGC ACA GTG CTG T AATCCCGGCA | 137 | | | |
| | -50 | Probe | TT CGT GTT TGC ACA GTG CTG T | 138 | | | |
| | -100 | Target | A CAG CAC TGT GCA AAC ACG AA | 139 | | | |
| | | Probe/target Hybrid | | | 21 | 11 | 48% | ΔG = -21.1 |
| | | Beacon | | | 40 | | 53% | ΔG = -0.48 |
| L-01-51 | -10 | Beacon | TGCCGGATT TCT CGC GAG GTC GCT TCT AATCCCGGCA | 140 | | | |
| | -50 | Probe | TCT CGC GAG GTC GCT TCT | 141 | | | |
| | -100 | Target | AGA AGC GAC CTC GCG AGA | 142 | | | |
| | | Probe/target Hybrid | | | 18 | 7 | 61% | ΔG = -21.0 |
| | | Beacon | | | | | | ΔG = -0.80 |
| L-01-52 | -10 | Beacon | TGCCGGATT CCC CCW CTT TGG TCT TGC GA AATCCCGGCA | 143 | | | |
| | -50 | Probe | CCC CCW CTT TGG TCT TGC GA | 144 | | | |
| | -100 | Target | TC GCA AGA CCA AAG WGG GGG | 145 | | | |
| | | Probe/target Hybrid | | | 20 | 8 | 60% | ΔG = -20.4 |
| | | Beacon | | | 39 | | 59% | ΔG = -0.59 |
| L-01-53 | -10 | Beacon | TGCCGGATT ATC CAT CAG CAC CCG AATCCCGGCA | 146 | | | |
| | -50 | Probe | ATC CAT CAG CGA CAC CCG | 147 | | | |
| | -100 | Target | CGG GTG TCG CTG ATG GAT | 148 | | | |
| | | Probe/target Hybrid | | | 18 | 7 | 61% | ΔG = -20.5 |
| | | Beacon | | | 38 | | 58% | ΔG = -0.80 |
| L-01-54 | -10 | Beacon | TGCCGGATT CCC TCT GAT GGG TAG GTT AATCCCGGCA | 149 | | | |
| | -50 | Probe | CCC TCT GAT GGG TAG GTT | 150 | | | |
| | -100 | Target | AAC CTA CCC ATC AGA GGG | 151 | | | |
| | | Probe/target Hybrid | | | 18 | 8 | 56% | ΔG = -19.2 |
| | | Beacon | | | 37 | | 57% | ΔG = -0.80 |
| L-01-55 | -10 | Beacon | GCCGCCGGCGT TTC AAA TCA AAA CCA TGC GGT TTC TCGCCCAGCGGC | 152 | | | |
| | -50 | Probe | TTC AAA TCA AAA CCA TGC GGT TTC | 153 | | | |
| | -100 | Target | GAA ACC GCA TGG TTT TGA TTT GAA | 154 | | | |
| | | Probe/target Hybrid | | | 24 | 15 | 38% | ΔG = -20.0 |
| | | Beacon | | | 47 | | 62% | ΔG = -9.42 |
| L-01-56 | -10 | Beacon | TGCCGGATT GGA AGA AGC TTG CTT CTT TGC AATCCCGGCA | 155 | | | |
| | -50 | Probe | GGA AGA AGC TTG CTT CTT TGC | 156 | | | |
| | -100 | Target | GCA AAG CAA GCT TCT TCC | 157 | | | |
| | | Probe/target Hybrid | | | 21 | 11 | 48% | ΔG = -20.3 |
| | | Beacon | | | 40 | | 53% | ΔG = -1.80 |
| L-01-57 | -10 | Beacon | CGCTC GCT GCC TCC CGT AGG AGT GAGCG | 158 | | | |
| | -50 | Probe | GCT GCC TCC CGT AGG AGT | 159 | | | |
| | -100 | Target | ACT CCT ACG GGA GGC AGC | 160 | | | |
| | | Probe/target Hybrid | | | 18 | 6 | 67% | -23.5 |
| | | Beacon | | | 28 | 12 | 71% | -0.94 |
| L-01-58 | -10 | | | | | | | |
| | -50 | | | | | | | |
| | -100 | | | | | | | |

TABLE I-continued

| | | | Sequence | SEQ ID NO | | | | |
|---|---|---|---|---|---|---|---|---|
| L-01-59- | 10 | Beacon | ACGCTC CAC CAT GAA GCA ACC CGT GAGCGT | 161 | | | | -19.5 |
| | -50 | Probe | CAC CAT GAA GCA ACC CGT | 162 | Probe/target Hybrid | 18 | 8 | 56% |
| | -100 | Target | ACG GGT TGC TTC ATG GTG | 163 | Beacon | 30 | | 60% | -0.50 |
| L-01-60 | -10 | Beacon | ACCCGCTA TT CCG ATA ATA CGC GGT ATT AGC GGGT | 164 | | | | ΔG = -21.4 |
| | -50 | Probe | TT CCG ATA ATA CGC GGT ATT AGC | 165 | Probe/target Hybrid | 23 | 13 | 43% |
| | -100 | Target | GCT AAT ACC GCG TAT TAT CGG AA | 166 | Beacon | 35 | | 51% | ΔG = -1.18 |
| L-01-61 | -10 | Beacon | CGGTGCTC TA ATA CGC GGT ATT AGC GAC AG AGAGCACCG | 167 | Probe/target Hybrid | 22 | 12 | 45% | ΔG = -20.3 |
| | -50 | Probe | TA ATA CGC GGT ATT AGC GAC AG | 168 | | | | |
| | -100 | Target | CT GTC GCT AAT ACC GCG TAT AT | 169 | Beacon | 39 | | 56% | ΔG = -1.76 |
| L-01-62 | -10 | Beacon | ACGCCGGCGT AGG TTA TTA ACC TCA TCG CCT TCGCCCAGCGT | 170 | Probe/target Hybrid | 21 | 12 | 43% | ΔG = -19.8 |
| | -50 | Probe | AGG TTA TTA ACC TCA TCG CCT | 171 | | | | |
| | -100 | Target | AGG CGA TGA GGT TAA TAA CCT | 172 | Beacon | 40 | | 63% | ΔG = -0.92 |
| L-01-63 | -10 | Beacon | GGAAGGATAT AGG TTA TTA ACC TCA CTC CCT TCC | 173 | Probe/target Hybrid | 24 | 13 | 46% | ΔG = -20.7 |
| | -50 | Probe | AGG TTA TTA ACC TCA CTC CCT TCC | 174 | | | | |
| | -100 | Target | GGA AGG GAG TGA GGT TAA TAA CCT | 175 | Beacon | 35 | | 46% | ΔG = -1.02 |
| L-01-64 | -10 | Beacon | CGC TCAT TCA ACG GAA GCT CGT TCG ATGAGCG | 176 | Probe/target Hybrid | 22 | 11 | 50% | ΔG = -21.5 |
| | -50 | Probe | TCAT TCA ACG GAA GCT CGT TCG | 177 | | | | |
| | -100 | Target | CGAAC GAGCTTCCGT TGAATGA | 178 | Beacon | 31 | | 48% | ΔG = -0.95 |
| L-01-65 | -10 | | | | | | 0 | |
| | -50 | | | | | | | |
| | -100 | | | | | | | |
| L-01-66 | -10 | | | | | | 0 | |
| | -50 | | | | | | | |
| | -100 | | | | | | | |
| L-01-67 | -10 | | | | | | 0 | |
| | -50 | | | | | | | |
| | -100 | | | | | | | |
| L-01-68 | -10 | | | | | | 0 | |
| | -50 | | | | | | | |
| | -100 | | | | | | | |
| L-01-69 | -10 | | | | | | 0 | |
| | -50 | | | | | | | |
| | -100 | | | | | | | |
| L-01-70 | -10 | | | | | | 0 | |
| | -50 | | | | | | | |
| | -100 | | | | | | | |

TABLE I-continued

| | | | | | | | | |
|---|---|---|---|---|---|---|---|---|
| L-01-71 | -10 | | | | | 0 | | |
| | -50 | | | | | | | |
| | -100 | | | | | | | |
| L-01-72 | -10 | | | | | 0 | | |
| | -50 | | | | | | | |
| | -100 | | | | | | | |
| L-01-73 | -10 | | | | | 0 | | |
| | -50 | | | | | | | |
| | -100 | | | | | | | |
| L-01-74 | -10 | | | | | 0 | | |
| | -50 | | | | | | | |
| | -100 | | | | | | | |
| L-01-75 | -10 | | | | | 0 | | |
| | -50 | | | | | | | |
| | -100 | | | | | | | |
| L-01-76 | -10 | Beacon | 179 | TGCCGGATT ATC TGA CCG TCC CAG GTT AATCCCGGCA | 18 | 8 | 56% | Probe/target Hybrid ΔG = -19.9 |
| | -50 | Probe | 180 | ATC TGA CCG TCC CAG GTT | | | | Beacon ΔG = -0.80 |
| | -100 | Target | 181 | AAC CTG GGA CGG TCA GAT | 37 | 9 | 57% | |
| L-01-77 | -10 | Beacon | 182 | ACGCTC ATA AGA TGT GGC GCA TGC GAGCT | 18 | 9 | 50% | Probe/target Hybrid -19.3 |
| | -50 | Probe | 183 | ATA AGA TGT GGC GCA TGC | | | | Beacon -0.64 |
| | -100 | Target | 184 | GCA TGC GCC ACA TCT TAT | 30 | | 57% | |
| L-01-78 | -10 | Beacon | 185 | to be determined | | 0 | | -19.0 |
| | -50 | Probe | 186 | ATT GCT AAC CTC GCT CGA | | | | -0.40 |
| | -100 | Target | | TCG AGC GAG GTT AGC AAT | | | | |
| L-01-79 | -10 | | | | | 0 | | |
| | -50 | | | | | | | |
| | -100 | | | | | | | |
| L-01-80 | -10 | Beacon | 187 | GGC GTC ACA CCG G AT ACG TAGTGCTACGCC | 18 | 6 | 67% | Probe/target Hybrid ΔG = -20.8 |
| | -50 | Probe | 188 | GGC GTC ACA CCG G AT ACG | | | | Beacon ΔG = -0.84 |
| | -100 | Target | 189 | CCGT ATC CGG TGT GAC GCC | 30 | | 63% | |
| L-01-81 | -10 | Beacon | 190 | ACTC GGC TTC ATG CCA ACA GTC GAGT | 21 | 11 | 57% | Probe/target Hybrid -20.2 |
| | -50 | Probe | 191 | GGC TTC ATG CCA ACA GTC | | | | Beacon -0.45 |
| | -100 | Target | 192 | GAC TGT TGG CAT GAA GCC | 25 | | 56% | |
| L-01-82 | -10 | Beacon | 193 | GACAC CAT AAG ATG CCG AGC GAG GTGTC | 18 | 8 | 56% | Probe/target Hybrid -19.2 |
| | -50 | Probe | 194 | CAT AAG ATG CCG AGC GAG | | | | Beacon -0.11 |
| | -100 | Target | 195 | CTC GCT CGG CAT CTT ATG | 28 | | 57% | |

TABLE I-continued

| | | | | | | | | | |
|---|---|---|---|---|---|---|---|---|---|
| L-01-83 | -10 | Beacon | | | | | | 0 | |
| L-01-84 | | | | | | | | 0 | |
| L-01-85 | -10 | Beacon | 196 | ACCGCCGGCGT A AGA CGA CTC GTC ATC ACC T TCGCCCAGCGGT | Probe/target Hybrid | 20 | 10 | 50% | ΔG = -20.3 |
| | -50 | Probe seq | 197 | A AGA CGA CTC GTC ATC ACC T | Beacon | 42 | | 67% | ΔG = -1.13 |
| | -100 | Target | 198 | A GGT GAT GAC GAGTCG TCT T | | | | | |
| L-01-86 | -10 | Beacon | 199 | GCCGCCGGCGT GGC AGA TTC CTA GGC ATT ACT TCGCCCAGCGGC | Probe/target Hybrid | 21 | 11 | 48% | ΔG = -21.2 |
| | -50 | Probe seq | 200 | GGC AGA TTC CTA GGC ATT ACT | Beacon | 44 | | 68% | ΔG = -1.65 |
| | -100 | Target | 201 | AGT AAT GCC TAG GAA TCT GCC | | | | | |
| L-01-87 | -10 | Beacon | 202 | AGCTC TGC GCT TTT GTG TAC GGG GCT GAGCT | Probe/target Hybrid | 21 | 10 | 57% | -25.3 |
| | -50 | Probe | 203 | TGC GCT TTT GTG TAC GGG GCT | Beacon | 31 | | 58% | -0.34 |
| | -100 | Target | 204 | AGC CCC GTA CAC AAA AGC GCA | | | | | |
| L-01-88 | -10 | Beacon | | not required, competitor is not labelled | Probe/target Hybrid Beacon | 18 | 7 | 61% | -18.8 |
| | -50 | Probe | 205 | G TGCA TTT GTG TAC GGG GC | | | | | |
| | -100 | Target | 206 | AGC CCC GTA CAC AAA AGC GCA | | | | | |
| L-01-89 | -10 | Beacon | 207 | CGCTC CTT CAC CTA CGT GTC AGC G GAGCG | Probe/target Hybrid | 19 | 8 | 58% | -21.1 |
| | -50 | Probe | 208 | CTT CAC CTA CGT GTC AGC G | Beacon | 29 | | 66% | -0.78 |
| | -100 | Target | 209 | C GCT GAC ACG TAG GTG AAG | | | | | |
| L-01-90 | -10 | Beacon | | not required, competitor is not labelled | Probe/target Hybrid | 20 | 10 | 50% | -9.6 |
| | -50 | Probe | 210 | T CAC CTA CAT ATC AGC GTG C | Beacon | | | | -0.26 |
| | -100 | Target | 211 | C GCT GAC ACG TAG GTG AAG A | | | | | |
| L-01-91 | -10 | Beacon | 212 | ? | Probe/target Hybrid Beacon | 18 | 9 | 50% | |
| | -50 | Probe | | GTT TAC CTG TGT GAC TGC | | | | | |
| | -100 | Target | | 0 | | | | | |
| L-01-92 | -10 | Beacon | 213 | TGCCGGATT CTT CAC CTA CGT GTC AGC G AATCCCGGCA | Probe/target Hybrid | 19 | 8 | 58% | ΔG = -21.1 |
| | -50 | Probe seq | 214 | CTT CAC CTA CGT GTC AGC G | Beacon | 38 | | 58% | ΔG = -0.69 |
| | -100 | Target | 215 | C GCT GAC ACG TAG GTG AAG | | | | | |
| L-01-93 | -10 | | | | | | 0 | | |
| | -50 | | | | | | | | |
| | -100 | | | | | | | | |
| L-01-94 | -10 | Beacon | 216 | GCCGCCGGCGT CG AGA CTC TAG CTT GCC AGT TCGCCCAGCGGC | Probe/target Hybrid | 20 | 9 | 55% | ΔG = -21.8 |
| | -50 | Probe seq | 217 | CG AGA CTC TAG CTT GCC AGT | Beacon | 43 | | 72% | ΔG = -1.76 |
| | -100 | Target | 218 | ACT GGC AAG CTA GAG TCT CG | | | | | |

TABLE I-continued

| | | | | | | | | |
|---|---|---|---|---|---|---|---|---|
| L-01-95 | -10 | Beacon | | TGCCGGATT TTC TCG TCC GTT CGC TCG ACT TGC AATCCCGGCA | 219 | 24 | 10 | 14 | 58% | ΔG = -20.7 |
| | -50 | Probe seq | TTC TCG TCC GTT CGC TCG ACT TGC | 220 | 43 | | 58% | ΔG = -0.22 |
| | -100 | Target | GCA AGT CGA GCG AAC GGA CGA GAA | 221 | | | | |
| L-01-96 | -10 | Beacon | GCAAC TT TCG CAC ATC AGC GTC AGT T GC | 222 | 21 | 11 | 10 | 48% | ΔG = -20.9 |
| | -50 | Probe seq | TT TCG CAC ATC AGC GTC AGT T | 223 | 28 | | 54% | ΔG = -0.84 |
| | -100 | Target | A ACT GAC GCT GAT GTG CGA AA | 224 | | | | |
| L-01-97 | -10 | Beacon | CCC TCT ACC ACA CTC TAG TCG GGT AGA GGG | 225 | 21 | 9 | 12 | 52% | ΔG = -21.2 |
| | -50 | Probe seq | CCC TCT ACC ACA CTC TAG TCG | 226 | 30 | | 57% | ΔG = -1.63 |
| | -100 | Target | CGA CTA GAG TGT GGT AGA GGG | 227 | | | | |
| L-01-98 | -10 | Beacon | GCCGCCGGCGT ACT CCT ACC AAC GTT CTT CTC TCGCCCAGCGGC | 228 | 21 | 10 | 11 | 48% | ΔG = -20.5 |
| | -50 | Probe seq | ACT CCT ACC AAC GTT CTT CTC | 229 | 45 | | 67% | ΔG = -0.79 |
| | -100 | Target | GAG AAG AAC GTT GGT AGG AGT | 230 | | | | |
| L-01-99 | -10 | Beacon | GGGCTTC GCC CTC CCT TTC TGG TTA GTT GAAGGCC | 231 | 21 | 10 | 11 | 52% | ΔG = -22.3 |
| | -50 | Probe seq | GCC GTC CCT TTC TGG TTA GTT | 232 | 35 | | 60% | ΔG = -1.15 |
| | -100 | Target | AAC TAA CCA GAA AGG GAC GGC | 233 | | | | |
| L-01-100 | -10 | Beacon | GCGT TAA GCA AAT GTC ATG CAA CAT CTA CTTAACGC | 234 | 25 | 17 | 8 | 32% | ΔG = -20.4 |
| | -50 | Probe seq | T TAA GCA AAT GTC ATG CAA CAT CTA | 235 | 38 | | 39% | ΔG = -0.64 |
| | -100 | Target | TAG ATG TTG CAT GAC ATT TGC TTA A | 236 | | | | |
| L-01-101 | -10 | Beacon | TGCCTTC GAG CAA TTG CCC CTT TTA AAT TAC GAAGGCA | 237 | 24 | 15 | 9 | 38% | ΔG = -20.0 |
| | -50 | Probe seq | GAG CAA TTG CCC CTT TTA AAT TAC | 238 | 38 | | 45% | ΔG = -1.01 |
| | -100 | Target | GTA ATT TAA AAG GGG CAA TTG CTC | 239 | | | | |
| L-01-102 | -10 | Beacon | ACGCTC GTT CCC CAA CTC CCT ACT GAGCGT | 240 | 18 | 8 | 10 | 56% | -20.2 |
| | -50 | Probe | GTT CCC CAA CTC CCT ACT | 241 | 30 | | 60% | -0.78 |
| | -100 | Target | AGT AGG GAG TTG GGG AAC | 242 | | | | |
| L-01-103 | -10 | Beacon | ACTC CCC CTT GTG TAA GGC AGG GAGT | 243 | 24 | 13 | 11 | 54% | -21.4 |
| | -50 | Probe | CCC CTT GTG TAA GGC AGG | 244 | 28 | | 54% | -0.61 |
| | -100 | Target | CCT GCC TTA CAC AAG GGG | 245 | | | | |
| L-01-104 | -10 | Beacon | ACGCTC CCC ACT TTG GTC CGA AGA GAGCGT | 246 | 18 | 8 | 10 | 56% | -19.6 |
| | -50 | Probe | CCC ACT TTG GTC CGA AGA | 247 | 30 | | 60% | -0.66 |
| | -100 | Target | TCT TCG GAC CAA AGT GGG | 248 | | | | |

TABLE I-continued

| Loop Diagostics Code number | Tm target: 71 +/- 3° C. | Td (Suggs et al) 48-60 | RNA Blast hits | Probe match direct hits I (16S only) | Probe match direct hits II (16S only) | Probe match direct hits III (16S only) |
|---|---|---|---|---|---|---|
| L-01-1 | 71.6 / 65.9 | -10 / -50 / -100 | 62 | 41 | Acinetobacter (651/1392) | Moraxellaceae (665/2068) | unclassified_Moraxellaceae (6/31) |
| L-01-2 | 72.2 / 69.8 | -10 / -50 / -100 | 62 | Acinetobacter_baumannii_X81667 | Moraxellaceae (23/2142) | | |
| L-01-3 | | -10 / -50 / -100 | | | | | |
| L-01-4 | | -10 / -50 / -100 | | | | | |
| L-01-5 | 70.8 / 63.3 | -10 / -50 / -100 | 62 | | | | |
| L-01-6 | 70.0 / 67.8 | -10 / -50 / -100 | 58 | | | | |
| L-01-7 | 69.4 / 63.1 | -10 / -50 / -100 | 68 | | | | |
| L-01-8 | 68.9 / 66.6 | -10 / -50 / -100 | 66 | | | | |
| L-01-9 | 68.6 / 66.0 | -10 / -50 / -100 | 56 | | | | |
| L-01-10 | 70.2 / 66.7 | -10 / -50 / -100 | 62 | 34 B_burgdorferi/100 Borrelia | 89 B_burgdorferi/245 Borrelia | | |
| L-01-11 | 68.8 / 65.9 | -10 / -50 / -100 | 62 | B. pertussis. Parapertussis, B.bronchiseptica, Bordetella_avium | 0 | 0 | 0 |
| L-01-12 | 69.6 / 68.0 | -10 / -50 / -100 | 66 | | Burkholderiaceae (1867/2900) | | |

TABLE I-continued

| ID | | | | |
|---|---|---|---|---|
| L-01-13 | -10 | 69.0 | 64 | Burkholderiaceae (78/2900) |
| | -50 | 69.0 | | |
| | -100 | | | |
| L- | -10 | 68.8 | 62 | Burkholderiaceae (3/2900) |
| | -50 | 69.0 | | |
| | -100 | | | |
| L-01-14 | -10 | 69.6 | 54 | Burkholderiaceae (23/2900) |
| | -50 | 69.9 | | |
| | -100 | | | |
| L-01-15 | -10 | 70.5 | 58 | Burkholderiaceae (67/2900). B pyrrocinea |
| | -50 | 65.3 | | |
| | -100 | | | |
| L-01-16 | -10 | 70.5 | 56 | Burkholderiaceae (23/2900) |
| | -50 | 65.3 | | |
| | -100 | | | |
| L-01-17 | -10 | 69.0 | 58 | Burkholderiaceae (1/2900) |
| | -50 | 67.1 | | |
| | -100 | | | |
| L-01-18 | -10 | 69.6 | 58 | Burkholderiaceaei (143/2900) |
| | -50 | 67.1 | | |
| L-01-19 | -10 | | 0 | |
| | -50 | | | |
| | -100 | | | |
| L-01-20 | -10 | 57 | 50 | |
| | -50 | 68.3 | | |
| | -100 | | | |
| L-01-21 | -10 | 63.6 | 52 | |
| | -50 | 67.4 | | |
| | -100 | | | |
| L-01-22 | -10 | 77.8 | 66 | |
| | -50 | 68.5 | | |
| | -100 | | | |
| L-01-23 | -10 | 70.1 | 56 | |
| | -50 | 68.0 | | |
| | -100 | | | |
| L-01-24 | -10 | 72.7 | 58 | |
| | -50 | | | |
| | -100 | | | |
| L-01-25 | -10 | 57.7 | 48 | |
| | -50 | 62.7 | | |
| | -100 | | | |

TABLE I-continued

| | | | | |
|---|---|---|---|---|
| L-01-26 | -10<br>-50<br>-100 | 72.6<br>67.8 | 60 | |
| L-01-27 | -10<br>-50<br>-100 | 69.8<br>67.8 | 58 | |
| L-01-28 | -10<br>-50<br>-100 | 63.6<br>62.7 | 54 | |
| L-01-29 | -10<br>-50<br>-100 | 61.9 | 54 | |
| L-01-30 | -10<br>-50<br>-100 | 67.3<br>62.5 | 54 | |
| L-01-31 | -10<br>-50<br>-100 | 68.2<br>64.3 | 56 | |
| L-01-32 | -10<br>-50<br>-100 | 72.2<br>67.8 | 60 | |
| L-01-33 | -10<br>-50<br>-100 | 65.8<br>65.7 | 54 | |
| L-01-34 | -10<br>-50<br>-100 | 68.3<br>66.2 | 58 | 26/26 @ 40 |
| L-01-35 | -10<br>-50<br>-100 | 70.8<br>66.4 | 66 | 1/3 @48 others non clinical speces |
| L-01-36 | -10<br>-50<br>-100 | 68.2° C<br>65.9 C | 60 | 7/7 @ 40 |
| L-01-37 | -10<br>-50<br>-100 | 74.0 C<br>69.5 C | 58 | 8/11 @34; 3 non-clinical |
| L-01-38 | -10<br>-50<br>-100 | 70.2 C<br>69.9 C | 60 | 17/24 @ 40; 3 C fennica;<br>1 C solomi; 1 C spp; 2 uncultured eukaryotic genes |

TABLE I-continued

| ID | | Temp | | Notes | | |
|---|---|---|---|---|---|---|
| L-01-39 | -10<br>-50<br>-100 | 71.5 C.<br>70.0 C. | 56 | 51/55 @40 | | |
| L-01-40 | -10<br>-50<br>-100 | 69.5° C.<br>66.9° C. | 62 | 4/11@42 | | |
| L-01-41 | -10<br>-50<br>-100 | | | | | |
| L-01-42 | -10<br>-50<br>-100 | 69.0<br>65.9 | 64 | only Citrobacter freundii and Pseudomonas aeruginosa @full score | 0 | 0 |
| L-01-43 | -10<br>-50<br>-100 | 69.4<br>65.6 | 64 | | | |
| L-01-44 | -10<br>-50<br>-100 | 69.4<br>68.0 | 66 | Only C-diff @ full score | Clostridium_difficile_X73450 | Clostridiaceae (18/8924) |
| L-01-45 | -10<br>-50<br>-100 | 73.1<br>65.2 | 60 | | | |
| L-01-46 | -10<br>-50<br>-100 | 69.1<br>67.6 | 62 | Only Clostridium perfringens with full score | Clostridiaceae (49/7851) | |
| L-01-47 | -10<br>-50<br>-100 | 69.3<br>63.6 | 56 | Only Clostridium perfringens with full score | Clostridiaceae (49/7851) | |
| L-01-48 | -10<br>-50<br>-100 | 71.3<br>70.9 | 64 | Only Clostridium tetani with full score | Clostridiaceae (1/8924) | |
| L-01-49 | -10<br>-50<br>-100 | | | | | |
| L-01-50 | -10<br>-50<br>-100 | 70.2<br>65.9 | 62 | 92 Enterobacteriaceae | 0 | 0 |
| L-01-51 | -10<br>-50<br>-100 | 70.7<br>68.2 | 58 | 101 Enterobacteriaceae | Enterobacteriaceae (1857/5527) including; Proteus (24/90); Providencia (17/35) | |

TABLE I-continued

| ID | Level | Value | # | Description | Organism | Extra |
|---|---|---|---|---|---|---|
| L-01-52 | -10 | 69.7 | 64 | 101 Enterobacteriaceae | Enterobacteriaceae (2663/5527) without Proteus&Providencia | |
| | -50 | 66.7 | | | | |
| | -100 | | | | | |
| L-01-53 | -10 | 69.5 | 58 | 18 Enterococci | genus Enterococcus (425/847) | |
| | -50 | 68.2 | | | | |
| | -100 | | | | | |
| L-01-54 | -10 | 67.7 | 56 | only E. faecalis with full sore | Enterococcus (193/803) the other 600 are mostly unclassified E, no faecalis | |
| | -50 | 68.2 | | | | |
| | -100 | | | | | |
| L-01-55 | -10 | 67.7 | 66 | 5 faecium and 1 faecalis at full score | 64/157 are faecium only 1 faecalis | 0 |
| | -50 | 64.0 | | | | |
| | -100 | | | | | |
| L-01-56 | -10 | 68.8 | 62 | 18 E. coli & EHEC/39 total rest is only Haemophilus_parasuis, Mannheimia alucosida. | 0 | 0 |
| | -50 | 67.2 | | | | |
| | -100 | | | | | |
| L-01-57 | -10 | 75.1 | 60 | | | |
| | -50 | 67.7 | | | | |
| | -100 | | | | | |
| L-01-58 | -10 | | | | | |
| | -50 | | | | | |
| | -100 | T 70.9 | | | | |
| L-01-59 | -10 | 68 | 56 | | | |
| | -50 | 66.2 | | | | |
| | -100 | | | | | |
| L-01-60 | -10 | 70.6 | 66 | Haemophilus_influenzae_F_U32708 | Pasteurellaceae (283/2293) | |
| | -50 | 69.1 | | | | |
| | -100 | | | | | |
| L-01-61 | -10 | 69.2 | 64 | Haemophilus_influenzae_F_U32708 | Pasteurellaceae (278/2293) | |
| | -50 | | | | | |
| | -100 | | | | | |
| L-01-62 | -10 | 68.1 | 60 | Klebsiella_pneumoniae_Y17656 | Enterobacteriaceae (32/5830) | |
| | -50 | 66.1 | | | | |
| | -100 | | | | | |
| L-01-63 | -10 | 69.3 | 70 | Klebsiella_oxytoca_Y17655 | Enterobacteriaceae (20/6874) | |
| | -50 | 68.3 | | | | |
| | -100 | | | | | |
| L-01-64 | -10 | 70.4 | 66 | Lactobacillus_brevis_X61134 | Lactobacillaceae (38/2674) | |
| | -50 | 66.6 | | | | |
| | -100 | | | | | |

TABLE I-continued

| | | | | |
|---|---|---|---|---|
| L-01-65 | -10 | | | |
| | -50 | | | |
| | -100 | 0 | | |
| L-01-66 | -10 | | | |
| | -50 | | | |
| | -100 | 0 | | |
| L-01-67 | -10 | | | |
| | -50 | | | |
| | -100 | 0 | | |
| L-01-68 | -10 | | | |
| | -50 | | | |
| | -100 | 0 | | |
| L-01-69 | -10 | | | |
| | -50 | | | |
| | -100 | 0 | | |
| L-01-70 | -10 | | | |
| | -50 | | | |
| | -100 | 0 | | |
| L-01-71 | -10 | | | |
| | -50 | | | |
| | -100 | 0 | | |
| L-01-72 | -10 | | | |
| | -50 | | | |
| | -100 | 0 | | |
| L-01-73 | -10 | | | |
| | -50 | | | |
| | -100 | 0 | | |
| L-01-74 | -10 | | | |
| | -50 | | | |
| | -100 | 0 | | |
| L-01-75 | -10 | | | |
| | -50 | | | |
| | -100 | 0 | | |
| L-01-76 | -10 | 69.2 | 56 | Only *Legionella* with full score |
| | -50 | 68.2 | | |
| | -100 | | | |
| L-01-77 | -10 | 67.5 | 54 | 78

TABLE I-continued

| | | | |
|---|---|---|---|
| L-01-78 | -10 | 67.1 | 0 |
| | -50 | 64.3 | |
| | -100 | | |
| L-01-79 | -10 | 0 | Proteus 23s sequence not found in data base; nearest hit is *E. coli* with a score of 28 (out of 36) |
| | -50 | | |
| | -100 | | |
| L-01-80 | -10 | 70.4 | 60 | 0 |
| | -50 | 66.2 | | |
| | -100 | | | |
| L-01-81 | -10 | 69 | 62 |
| | -50 | 65.5 | |
| | -100 | | |
| L-01-82 | -10 | 67.5 | |
| | -50 | 63.2 | |
| | -100 | | |
| L-01-83 | -10 | 0 | |
| | -50 | | |
| | -100 | | |
| L-01-84 | -10 | 0 | | 0 |
| | -50 | | | |
| | -100 | | | |
| L-01-85 | -10 | 69.1 | 60 |
| | -50 | 67.4 | |
| | -100 | | |
| L-01-86 | -10 | 70.5 | 62 |
| | -50 | 69.4 | |
| | -100 | | |
| L-01-87 | -10 | 77.6 | 64 |
| | -50 | 64.1 | |
| | -100 | | |
| L-01-88 | -10 | 66.4 | 58 |
| | -50 | | |
| | -100 | | |
| L-01-89 | -10 | 70.8 | 60 |
| | -50 | 68.0 | |
| | -100 | | |
| L-01-90 | -10 | 46 | 60 | 0 |
| | -50 | 64.0 | | |
| | -100 | | | |
| L-01-91 | -10 | | 54 |
| | -50 | | |
| | -100 | | |

TABLE I-continued

| | | | | | |
|---|---|---|---|---|---|
| L-01-92 | -10<br>-50<br>-100 | 70.4<br>67.4 | 60 | 9 Salmonella, 1 Y enterolytica, no other hit | 0 |
| L-01-93 | -10<br>-50<br>-100 | | 0 | | 0 |
| L-01-94 | -10<br>-50<br>-100 | 71.6<br>69.9 | 62 | Serratia_marcescens_AF124042 | opened, click to collapse genus Serratia (249/544) (hits/total searched) |
| L-01-95 | -10<br>-50<br>-100 | 69.9<br>64.0 | 76 | 12 Stapg aureus w full score, no others | 77 out of 171 (Staur catches 78/269 and is therefore less specific |
| L-01-96 | -10<br>-50<br>-100 | 70.2<br>Tm =<br>66.4 Å° C. | 62 | | Staphylococcaceae (1230/2473) |
| L-01-97 | -10<br>-50<br>-100 | 70.5<br>70.8 | 66 | | |
| L-01-98 | -10<br>-50<br>-100 | 69.1<br>65.7 | 64 | Streptococcus agalactiae,<br>Streptococcus difficile @ full score | Streptococcaceae (96/7045) |
| L-01-99 | -10<br>-50<br>-100 | 72.7<br>69.9 | 64 | Streptococcus_criae_X58316 | Lactobacillales (337/12134) |
| L-01-100 | -10<br>-50<br>-100 | 68.4<br>65.9 | 66 | Streptococcus_mitis_D38482 | |
| L-01-101 | -10<br>-50<br>-100 | 67.9<br>67.7 | 66 | Streptococcus_pyogenes_AF076028 | Streptococcaceae (95/7045) |
| L-01-102 | -10<br>-50<br>-100 | 69.1<br>68.3 | 56 | | |
| L-01-103 | -10<br>-50<br>-100 | 71.8<br>67.5 | 70 | | |

TABLE I-continued

| Loop Diagnostics Code number | | Reference for cognate sequence |
|---|---|---|
| L-01-104 | -10<br>-50<br>-100 | 68.1    56<br>67.0 |
| L-01-1 | -10<br>-50<br>-100 | Wagner M., Erhart R., Manz W., Amann R., Lemmer H., Wedi D. and Schleifer K.-H. (1994). Appl. Environ. Microbiol. 60: 792-800. |
| L-01-2 | -10<br>-50<br>-100 | New |
| L-01-3 | -10<br>-50<br>-100 | New |
| L-01-4 | -10<br>-50<br>-100 | New |
| L-01-5 | -10<br>-50<br>-100 | New |
| L-01-6 | -10<br>-50<br>-100 | New |
| L-01-7 | -10<br>-50<br>-100 | New |
| L-01-8 | -10<br>-50<br>-100 | New |
| L-01-9 | -10<br>-50<br>-100 | See also Pat. 4,977,251 11.12.1990: DNA Sonden für die Detektion von Bacteroides Spezies (expired) Manz W., et al.. (1996). Application of a suite of 16S rRNA-specific oligonucleotide probes designed to investigate bacteria of the phylum cytophaga-flavobacter-bacteroides in the natural environment. Microbiol. 142: 1097-1106. |
| L-01-10 | -10<br>-50<br>-100 | Hammer et al, Microbiology (2001), 147, 1425-1436. |
| L-01-11 | -10<br>-50<br>-100 | Jürgen Bohnert, Barbara Hübner, Konrad Botzenhart, Int. J. Hyg. Environ. Health 203, 77-82 (2000) |

TABLE I-continued

| | | |
|---|---|---|
| L-01-12 | -10<br>-50<br>-100 | New |
| L-01-13 | -10<br>-50<br>-100 | New: according to Govan this should cover, *B. pyrocina*, *stabilis*, *multivorans*, *cepacia*, *ambiforia* |
| L- | | New: according to Govan this should cover, *B. dolosa*, *cenocepacia*, *vietnamensis*, *anthina* |
| L-01-14 | -10<br>-50<br>-100 | New: only *B. cepacia* and *tropicalis* |
| L-01-15 | -10<br>-50<br>-100 | New, catches *B pyrocina*, *stabilis* and *ambifaria* |
| L-01-16 | -10<br>-50<br>-100 | New: according to Govan this should cover, *B. doloda anthinia* |
| L-01-17 | -10<br>-50<br>-100 | New: according to Govan this should cover, *B. multivorans* |
| L-01-18 | -10 | New: according to Govan this should cover, *B. cenocepacia* and *vietnamiensis* |
| L-01-19 | -10<br>-50<br>-100 | Popped presentation in Jena, slides available, and Sven Poppert, Andreas Essig, Reinhard Marre, Michael Wagner, and Matthias Horn. 2002. Detection and differentiation of chlamydiae by fluorescence in situ hybridization (FISH). Appl. Environ. Microbial: 68; 4081-4089 |
| L-01-20 | -10<br>-50<br>-100 | Poppert presentation in Jena, slides available, and Sven Poppert, Andreas Essig, Reinhard Marre, Michael Wagner, and Mathias Horn. 2002. Detection and differentiation of chlamydiae by fluorescence in situ hybridization (FISH). Appl. Environ. Microbial: 68; 4081-4089 |
| L-01-21 | -10<br>-50<br>-100 | Poppert presentation in Jena, slides available, and Sven Poppert, Andreas Essig, Reinhard Marre, Michael Wagner, and Matthias Horn. 2002. Detection and differentiation of chlamydiae by fluorescence in situ hybridization (FISH). Appl. Environ. Microbial: 68; 4081-4089 |
| L-01-22 | -10<br>-50<br>-100 | Poppert presentation in Jena, slides available, and Sven Poppert, Andreas Essig, Reinhard Marre, Michael Wagner, and Mdtthias Horn. 2002. Detection and differentiation of chlamydiae by fluorescence in situ hybridization (FISH). Appl. Environ. Microbial: 68; 4081-4089 |
| L-01-23 | -10<br>-50<br>-100 | Poppert presentation in Jena, slides available, and Sven Poppert, Andreas Essig, Reinhard Marre, Michael Wagner, and Matthias Horn. 2002. Detection and differentiation of chlamydiae by fluorescence in situ hybridization (FISH). Appl. Environ. Microbial: 68; 4081-4089 |
| L-01-24 | -10<br>-50<br>-100 | Poppert presentation in Jena, slides available, and Sven Popped, Andreas Essig, Reinhard Marre, Michael Wagner, and Matthias Horn. 2002. Detection and differentiation of chlamydiae by fluorescence in situ hybridization (FISH). Appl. Environ. Microbial: 68; 4081-4089 |

TABLE I-continued

| | | |
|---|---|---|
| L-01-25 | -10<br>-50<br>-100 | Applied and Environmental Microbiology, August 2002, p. 4081-4089, Vol. 68, No. 8 |
| L-01-26 | -10<br>-50<br>-100 | Applied and Environmental Microbiology, August 2002, p. 4081-4089, Vol. 68, No. 8 |
| L-01-27 | -10<br>-50<br>-100 | Applied and Environmental Microbiology, August 2002, p. 4081-4089, Vol. 68, No. 8 |
| L-01-28 | -10<br>-50<br>-100 | Applied and Environmental Microbiology, August 2002, p. 4081-4089, Vol. 68, No. 8 |
| L-01-29 | -10<br>-50<br>-100 | Applied and Environmental Microbiology, August 2002, p. 4081-4089, Vol. 68, No. 8 |
| L-01-30 | -10<br>-50<br>-100 | Applied and Environmental Microbiology, August 2002, p. 4081-4089, Vol. 68, No. 8 |
| L-01-31 | -10<br>-50<br>-100 | Applied and Environmental Microbiology, August 2002, p. 4081-4089, Vol. 68, No. 8 |
| L-01-32 | -10<br>-50<br>-100 | Applied and Environmental Microbiology, August 2002, p. 4081-4089, Vol. 68, No. 8 |
| L-01-33 | -10<br>-50<br>-100 | Applied and Environmental Microbiology, August 2002, p. 4081-4089, Vol. 68, No. 8 |
| L-01-34 | -10<br>-50<br>-100 | New |
| L-01-35 | -10<br>-50<br>-100 | New |
| L-01-36 | -10<br>-50<br>-100 | New |
| L-01-37 | -10<br>-50<br>-100 | New |

TABLE I-continued

| ID | | Description |
|---|---|---|
| L-01-38 | -10<br>-50<br>-100 | New |
| L-01-39 | -10<br>-50<br>-100 | New |
| L-01-40 | -10<br>-50<br>-100 | New |
| L-01-41 | -10<br>-50<br>-100 | New |
| L-01-42 | -10<br>-50<br>-100 | INAUGURAL-DISSERTATION, Qiang Fang, zu Tübingen, C:\Aktenkoffer\paper\FISH\23s-probe for *Salmonella*.pdf |
| L-01-43 | -10<br>-50<br>-100 | derived from Meier H., Amann R., Ludwig W. and Schleifer K.-H. (1999). Specific oligonucleotide probes for in situ detection . . . Syst. Appl. Microbiol. 22: 186-196. This detects Firmicutes. TGG AAG ATT CCC TAC TGC crap. Clavel T., Borrmann D., Braune A., Doré J. and Blaut M. (2006). Occurrence and activity of human intestinal bacteria that activate dietary lignans. Anaerobe: In press, 5'-CTC GGA CAT TAC TGC CCG CG-3' |
| L-01-44 | -10<br>-50<br>-100 | New |
| L-01-45 | -10<br>-50<br>-100 | derived from Meier H., Amann R., Ludwig W. and Schleifer K.-H. (1999). Specific oligonucleotide probes for in situ detection . . . Syst. Appl. Microbiol. 22: 186-196. This detects Firmicutes. TGG AAG ATT CCC TAC TGC crap. Clavel T., Borrmann D., Braune A., Doré J. and Blaut M. (2006). Occurrence and activity of human intestinal bacteria that activate dietary lignans. Anaerobe: In press, 5'-CTC GGA CAT TAC TGC CCG CG-3' |
| L-01-46 | -10<br>-50<br>-100 | Rönner S. G. E. and Stackebrandt E. (1994). Identification of *Clostridium perfringens* by 16S and 23S rRNA oligonucleotide probes. Syst. Appl. Microbial. 17: 425-432. |
| L-01-47 | -10<br>-50<br>-100 | Rönner S. G. E. and Stackebrandt E. (1994). Identification of *Clostridium perfringens* by 16S and 23S rRNA oligonucleotide probes. Syst. Appl. Microbial. 17: 425-432. |
| L-01-48 | -10<br>-50<br>-100 | New |
| L-01-49 | -10<br>-50<br>-100 | New |

TABLE I-continued

| | | |
|---|---|---|
| L-01-50 | -10<br>-50<br>-100 | derived from Jürgen Bohnert, Barbara Hübner, Konrad Botzenhart Int. J. Hyg. Environ. Health 203, 77-82 (2000) |
| L-01-51 | -10<br>-50<br>-100 | derived from Ootsubo M., Shimizu T., Tanaka R., Sawabe T., Tajima K., Yoshimizu M., Ezura Y., Ezaki T. and Oyaizu H. (2002). Oligonucleotide probe for detecting Enterobacteriaceae by in situ hybridization. J. Appl. Microbiol. 93: 60-68. |
| L-01-52 | -10<br>-50<br>-100 | derived from Kempf V. A., Trebesius K. and Autenrieth I. B. (2000). Fluorescent in situ hybridization allows rapid identification of microorganisms in blood cultures. J. Clin. Microbiol. 38: 830-838. |
| L-01-53 | -10<br>-50<br>-100 | derived from: Wang R., Beggs M., Robertson L. and Cerniglia C. (2002). Design and evaluation of oligonucleotide-microarray method for the detection of human intestinal bacteria in fecal samples. FEMS Microbiol. Lett. 213: 175-182. |
| L-01-54 | -10<br>-50<br>-100 | derived from Behr T., Koob C., Schedl M., Mehlen A., Meier H., Knopp D., Frahm E., Obst U., Schleifer K., Niessner R. and Ludwig W. (2000). A nested array of rRNA targeted probes for the detection and identification of enterococci by reverse hybridization. Syst. Appl. Microbiol. 23: 563-572. |
| L-01-55 | -10<br>-50<br>-100 | NEW, started from the Wang sequence and moved towards 5' step by step and ran BLASTs |
| L-01-56 | -10<br>-50<br>-100 | derived from: Wang R., Beggs M., Robertson L. and Cerniglia C. (2002). Design and evaluation of oligonucleotide-microarray method for the detection of human intestinal bacteria in fecal samples. FEMS Microbiol. Lett. 213: 175-182. |
| L-01-57 | -10<br>-50<br>-100 | Amman review 1995 |
| L-01-58 | -10<br>-50<br>-100 | New |
| L-01-59 | -10<br>-50<br>-100 | Compare sequence: Patent 5654418 05.08.1997 von Sheiness (Becton Dickinson and Company): Nucleic acid probes useful for detecting microorganisms associated with vaginal infections. Verfahren zur Detektion von Mikroorganismen diemit vaginalen Krankheiten assoziiert sind, z. B. Gardnerella vaginalis, Trichomonas vaginalis und Candida albicans. Beispiel für ein Krankheitsbild und den entsprechenden Sondensatz. |
| L-01-60 | -10<br>-50<br>-100 | New 6 base over-lap w Haeinf-1 |
| L-01-61 | -10<br>-50<br>-100 | New, no over-lap |
| L-01-62 | -10<br>-50<br>-100 | New |

TABLE I-continued

| | | |
|---|---|---|
| L-01-63 | -10<br>-50<br>-100 | NEW |
| L-01-64 | -10<br>-50<br>-100 | derived from Blasco L., Ferrer S. and Pardo I. (2003). Development of specific fluorescent oligonucleotide probes for in situ identification of wine lactic acid bacteria. FEMS Microbiol. Lett. 225: 115-123. |
| L-01-65 | -10<br>-50<br>-100 | |
| L-01-66 | -10<br>-50<br>-100 | |
| L-01-67 | -10<br>-50<br>-100 | |
| L-01-68 | -10<br>-50<br>-100 | |
| L-01-69 | -10<br>-50<br>-100 | |
| L-01-70 | -10<br>-50<br>-100 | |
| L-01-71 | -10<br>-50<br>-100 | |
| L-01-72 | -10<br>-50<br>-100 | |
| L-01-73 | -10<br>-50<br>-100 | |
| L-01-74 | -10<br>-50<br>-100 | |
| L-01-75 | -10<br>-50<br>-100 | |

TABLE I-continued

| | | |
|---|---|---|
| L-01-76 | -10<br>-50<br>-100 | Dorothee Grimm, 1 Hilde Merkert, 1 Wolfgang Ludwig, 2 Karl-Heinz Schleifer, 2 Jörg Hacker, 1 and Bettina C. Brandl* Appl Environ Microbiol. 1998 July; 64(7): 2686-2690. |
| L-01-77 | -10<br>-50<br>-100 | Wang, R. -F., Cao, W. -W. and Johnson, M. G. (1991). Development of a 16S rRNA-based oligomer probe specific for Listeria monocytogenes. Appl. Environ. Microbiol. 57, 3666-3670. |
| L-01-78 | -10<br>-50<br>-100 | |
| L-01-79 | | |
| L-01-80 | -10<br>-50<br>-100 | derived from INAUGURAL-DISSERTATION, Qiang Fang, zu Tübingen, C:\Aktenkoffer\paper\FISH\23s-probe for Salmonella.pdf |
| L-01-81 | -10<br>-50<br>-100 | New |
| L-01-82 | -10<br>-50<br>-100 | New |
| L-01-83 | | |
| L-01-84 | | |
| L-01-85 | -10<br>-50<br>-100 | New |
| L-01-86 | -10<br>-50<br>-100 | New |
| L-01-87 | -10<br>-50<br>-100 | Salmonella spp. in foods by fluorescent in situ hybridization with 23S rRNA probes: a comparison with conventional culture methods. J Food Prot. 2003 May; 66(5)723-31 *Fang Q, Brockmann |
| L-01-88 | -10<br>-50<br>-100 | Salmonella spp. in foods by fluorescent in situ hybridization with 23S rRNA probes: a comparison with conventional culture methods. J Food Prot. 2003 May; 66(5)723-31 *Fang Q, Brockmann |
| L-01-89 | -10<br>-50<br>-100 | Salmonella spp. in foods by fluorescent in situ hybridization with 23S rRNA probes: a comparison with conventional culture methods. J Food Prot. 2003 May; 66(5)723-31 *Fang Q, Brockmann |
| L-01-90 | -10<br>-50<br>-100 | Salmonella spp. in foods by fluorescent in situ hybridization with 23S rRNA probes: a comparison with conventional culture methods. J Food Prot. 2003 May; 66(5)723-31 *Fang Q, Brockmann |

TABLE I-continued

| ID | Value | Reference |
|---|---|---|
| L-01-91 | -10<br>-50<br>-100 | *Salmonella* spp. in foods by fluorescent in situ hybridization with 23S rRNA probes: a comparison with conventional culture methods. J Food Prot. 2003 May; 66(5)723-31 *Fang Q, Brockmann |
| L-01-92 | -10<br>-50<br>-100 | *Salmonella* spp. in foods by fluorescent in situ hybridization with 23S rRNA probes: a comparison with conventional culture methods. J Food Prot. 2003 May; 66(5)723-31 *Fang Q, Brockmann |
| L-01-93 | -10<br>-50<br>-100 | New |
| L-01-94 | -10<br>-50<br>-100 | new |
| L-01-95 | -10<br>-50<br>-100 | derived from Urakawa H., Fantroussi, S. E., Smidt, H., Smoot, J. C., Tribou, E. H., Kelly, J. J., Noble, P. A., Stahl, D. A. (2003). Optimization of single-base-pair mismatch discrimination in oligonucleotide microarrays. Appl. Envir. Microbiol. 69: 2848-2856. |
| L-01-96 | -10<br>-50<br>-100 | derived from Urakawa H., Fantroussi, S. E., Smidt, H., Smoot, J. C., Tribou, E. H., Kelly, J. J., Noble, P. A., Stahl, D. A. (2003). Optimization of single-base-pair mismatch discrimination in oligonucleotide microarrays. Appl. Envir. Microbiol. 69: 2848-2856. |
| L-01-97 | -10<br>-50<br>-100 | New |
| L-01-98 | -10<br>-50<br>-100 | New |
| L-01-99 | -10<br>-50<br>-100 | New |
| L-01-100 | -10<br>-50<br>-100 | New |
| L-01-101 | -10<br>-50<br>-100 | New |

TABLE I-continued

| | | |
|---|---|---|
| L-01-102 | -10<br>-50<br>-100 | Compare sequence: Pat. 5,728,522 17.03.1998 von Del Vecchio (Research Corporation Technologies): Oligonucleotides and nucleic acids for the detection of Ureaplasma urealyticum. Test für die PCR-Detektion von Ureaplasma urealyticum |
| L-01-103 | -10<br>-50<br>-100 | |
| L-01-104 | -10<br>-50<br>-100 | Compare for sequences: Pat. 5,593,831 14.01.1997 von Shah (Amoco Corporation): Nucleic acid probes for the detection of Yersinia enterocolitica: Nukleinsäure Sonden, die an die rRNA von Y. enterocolitica binden nicht aber an die rRNA von non-Yersinia enterocolitica für die Detektion von Yersinia enterocolitica in Nahrungsmitteln und anderen Proben. Karlheinz Trebesius et al., Journal of Clinical Microbiology, September 1998, p. 2557-2564, Vol. 36, No. 9 |

TABLE 2

| Loop Diagnostics Code number | Target organism | Sequence 5'-3' | | Length | GC content | PNA-suitable? on GC content | on <3-base self complem. | on 4 purins in a row | length inverse seq., (max palindromes/ 18) repeats/ hairpin | Final |
|---|---|---|---|---|---|---|---|---|---|---|
| L-01-1 | -10 Acinetobacter -50 -100 | TGCCGGATT ACC ATC CTC TCC CAT ACT CTA AATCCGGCA | Beacon | 39 | 54% | yes | no | no | no | no |
| L-01-2 | -10 Acinatobacter baumanii -50 -100 | ACC ATC CTC TCC CAT ACT CTA TAG AGT ATG GGA GAG GAT GGT | Probe/target Hybrid | 21 | 10 48% | yes | yes | yes | no | no |
| | | GCGCG TC CGG TAG CAA GCT ACC TTC CGCGC | Beacon | 30 | 21 70% | no | no | no | no | no |
| | | TC CGG TAG CAA GCT ACC TTC GAA GGT AGC TTG CTA CCG GA | Probe/target Hybrid | 20 | 11 55% | yes | | no | no | no |
| L-01-3 | -10 Actinomyces -50 -100 | | | | | | | | | |
| L-01-4 | -10 Aspergillus spp -50 -100 | | | | | | | | | |
| L-01-5 | -10 Aspergillus flavus -50 -100 | CCGCCGGCGT AC AGA GTT CGT GGT GTC TCC TCGCCCAGCGG | Beacon | 41 | 29 71% | no | no | yes | no | no |
| | | AC AGA GTT CGT GGT GTC TCC GGA GAC ACC ACG AAC TCT GT | Probe/target Hybrid | 20 | 11 55% | yes | yes | no | no | no |
| L-01-6 | -10 Aspergillus fumigatus -50 -100 | cgtc gcc tac aga gca ggt gac g gcc tac aga gca ggt gac gtc acc tgc tct gta ggc | Beacon | 23 | 15 65% | no | no | yes | no | no |
| | | | Probe/target Hybrid | 18 | 11 61% | no | no | no | yes | no |
| L-01-7 | -10 Aspergillus niger -50 -100 | ctctga a ctg att gca ttc aat caa ctc agag | Beacon | 32 | 13 41% | yes | no | yes | no | no |
| | | a ctg att gca ttc aat caa ctc aga tct gag ttg att gaa tgc aat cag t | Probe/target Hybrid | 25 | 9 36% | yes | no | yes | no | no |
| L-01-8 | -10 Aspergillus terreus -50 -100 | TCCGTC tga ttg caa aga atc aca ctc aga GACGGA | Beacon | 36 | 17 47% | yes | no | yes | no | no |
| | | tga ttg caa aga atc aca ctc aga tct gag tgt tct ttg caa tca | Probe/target Hybrid | 24 | 9 38% | yes | no | yes | no | no |
| L-01-9 | -10 Bacteroides/ Prevotella -50 -100 | GCCGCCGGCAT CCA ATG TGG GGG ACC TTC TAGCCCAGCGGC | Beacon | 39 | 29 74% | no | no | no | no | no |
| | | CCA ATG TGG GGG ACC TTC GAA GGT CCC CCA CAT TGG | Probe/target Hybrid | 17 | 11 59% | yes | no | no | yes | no |

TABLE 2-continued

| Loop Diagnostics Code number | Target organism | Sequence 5'-3' | | Length | GC content | PNA-suitable? | | | | Final |
|---|---|---|---|---|---|---|---|---|---|---|
| | | | | | | on GC content | on <3-base self complem. | on 4 purins in a row | length inverse seq., (max palindromes/18) repeats/hairpin | |
| L-01-10 | Borrelia burgdorferi -50 -100 | TGCCGGATT CA TGC TTA AGA CGC ACT GCC AATCCGGCA | Beacon | 39 | 56% | yes | | yes | no | no |
| | | CA TGC TTA AGA CGC ACT GCC GGC AGT GCG TCT TAA GCA TG | Probe/target Hybrid | 20 | 50% | yes | no | no | no | no |
| L-01-11 | Bordetella pertussis -50 -100 | TGCCGGATT CAG CAC TCT GCA AAG ACG AAA AATCCCGGCA | Beacon | 40 | 53% | yes | | yes | no | no |
| | | CAG CAC TCT GCA AAG ACG AAA TTT CGT CTT TGC AGA GTG CTG | Probe/target Hybrid | 21 | 48% | yes | no | no | no | no |
| L-01-12 | Burkholderia cepacia complex = Option I -50 -100 | ACCGCTC TTT CTT TCC GGA CAA AAG TGC TTT GAGCGGCT | Beacon | 39 | 51% | yes | | no | no | no |
| | | TTT CTT TCC GGA CAA AAG TGC TTT AAA GCA CTT TTG TCC GGA AAG AAA | Probe/target Hybrid | 24 | 38% | yes | no | no | no | no |
| L-01-13 | Burkholderia cepacia complex, two beacons, Option II -50 -100 | CGCCTTC AGA ACC AAG GAT TTC TTT CCG G GAAGGCG | Beacon | 36 | 56% | yes | | no | no | no |
| | | AGA ACC AAG GAT TTC TTT CCG G CCG GAA AGA AAT CCT TGG TTC T | Probe/target Hybrid | 22 | 45% | yes | no | no | no | no |
| L- | | ACGCA AGAGCCAAGGTTTCTTTCCG CTTGCGT | Beacon | 34 | 50% | yes | | yes | no | no |
| | | AGA GCC AAG GTT TTC TTT CCG CGG AAA GAA AAC CTT GGC TCT | Probe/target Hybrid | 21 | 48% | yes | no | yes | no | no |
| L-01-14 | Burkholderia cepacia | ACGCTC G TCA TCC CCC GGC CAT GAGCGT | Beacon | 28 | 68% | no | | no | no | no |
| | | G TCA TCC CCC GGC CAT ATG GCC GGG GGA TGA C | Probe/target Hybrid | 16 | 69% | no | no | no | yes | no |
| L-01-15 | Burkholderia pyrrocinia/stabilis/ambifaria -50 -100 | CGCTC CGT CAT CCC CCG GCT ATA GGAGCG | Beacon | 29 | 69% | no | | no | no | no |
| | | CGT CAT CCC CCG GCT ATA TAT AGC CGG GGG ATG ACG | Probe/target Hybrid | 18 | 61% | no | no | no | yes | no TABLE 2-continued

| Code | Loop Diagostics number | Target organism | Sequence 5'-3' | | Length | | GC content | PNA-suitable? on GC content | on <3-base self complem. | on 4 purins in a row | length inverse seq., (max palindromes/ 18) repeats/ hairpin | Final |
|---|---|---|---|---|---|---|---|---|---|---|---|---|
| L-01-17 | -10 | *Burkholderia multivorans* | GCCGCCGGCGT CGT CAT CCC CCG ATC GTA TCGCCCAGCGGC | Beacon | 41 | | 73% | no | | no | no | no |
| | -50<br>-100 | | CGT CAT CCC CCG ATC GTA<br>TAC GAT CGG GGG ATG ACG | Probe/target Hybrid | 18 | 11 | 61% | no | no | no | yes | no |
| L-01-18 | -10 | *Burkholderia cenocepacia/ vietnamiensis* | GCCGCCGGCGT CGT CAT CCC CCG ACT GTA TCGCCCAGCGGC | Beacon | 41 | | 76% | no | | no | no | no |
| | | | CGT CAT CCC CCG ACT GTA<br>TAC AGT CGG GGG ATG ACG | Probe/target Hybrid | 18 | 11 | 61% | no | no | no | yes | no |
| L-01-19 | -10<br>-50<br>-100 | *Campylobacter* (pathogenic thermophiles | GCC CTA AGC GTC CTT CCA | | 18 | 11 | 61% | no | | no | yes | no |
| L-01-20 | -10 | *Campylobacterlari* | ACGCTC GAA GTG TAA GCA ACT AAA T GAGCGT | Beacon | 31 | | 45% | yes | | yes | no | no |
| | -50<br>-100 | | GAA GTG TAA GCA ACT AAA T<br>A TTT AGT TGC TTA CAC TTC | Probe/target Hybrid | 19 | 6 | 32% | yes | no | yes | no | no |
| L-01-21 | -10 | *Campylobacter jejuni* | ACGCTC AGC TAA CCA CTT ATA CCG GAGCGT | Beacon | 30 | | 53% | yes | | yes | no | no |
| | -50<br>-100 | | AGC TAA CCA CTT ATA CCG<br>CGG TAT AAG TGG TTA GCT | Probe/target Hybrid | 18 | 8 | 44% | yes | no | no | yes | no |
| L-01-22 | -10 | *Cp. upsaliensis* | CCGCTC CGT GTG TCG CCC TAG GCG TA GAGCGG | Beacon | 32 | | 72% | no | no | no | no | no |
| | -50<br>-100 | | CGT GTG TCG CCC TAG GCG TA<br>TA CGC CTA GGG CGA CAC ACG | Probe/target Hybrid | 20 | 13 | 65% | no | | no | no | no |
| L-01-23 | -10 | *Cp coli* | CCGCTC TCG ATG GCA TCA GGG GTT GAGCGG | Beacon | 30 | | 67% | no | no | no | no | no |
| | -50<br>-100 | | TCG ATG GCA TCA GGG GTT<br>AAC CCC TGA TGC CAT CGA | Probe/target Hybrid | 18 | 10 | 56% | yes | | no | yes | no |
| L-01-24 | -10 | *Cp coli*-comp | not required, competitor is not labelled | Beacon | | | | | | | | |
| | -50<br>-100 | | TCG ACG GCA TCA GGG GTT<br>AAC CCC TGA TGC CGT CGA | Probe/target Hybrid | 18 | 11 | 61% | no | | no | yes | no |
| L-01-25 | -10 | *Chlamydia* | ACGCCGGCGT TAG CTG ATA TCA CAT AGA TCGCCCAGCGT | Beacon | 39 | | 59% | yes | no | yes | no | no |
| | -50<br>-100 | | TAG CTG ATA TCA CAT AGA<br>TCT ATG TGA TAT CAG CTA | Probe/target Hybrid | 18 | 6 | 33% | yes | | no | yes | no |

TABLE 2-continued

| Loop Diagnostics Code number | Target organism | Sequence 5'-3' | | Length | GC content | PNA-suitable? | | | | Final |
|---|---|---|---|---|---|---|---|---|---|---|
| | | | | | | on GC content | on <3-base self complem. | on 4 purins in a row | length inverse seq., (max palindromes/ 18) repeats/ hairpin | |
| L-01-26 | -10 Chlamydiaceae -50 -100 | TCCAGCCGGCGT CTT TCC GCC TAC ACG CCC TCGCCCAGCGGA CTT TCC GCC TAC ACG CCC GGG CGT GTA GGC GGA AAG | Beacon Probe/target Hybrid | 41 18 | 73% 67% | no no | no | no no | no yes | no no |
| L-01-27 | -10 Chlamydiales -50 -100 | TCCGCCGGCGT CCT CCG TAT TAC CGC AGC TCGCCCAGCGGA CCT CCG TAT TAC CGC AGC GCT GCG GTA ATA CGG AGG | Beacon Probe/target Hybrid | 41 18 | 71% 61% | no no | no | no no | no yes | no no |
| L-01-28 | -10 Chlamydophila -50 -100 | ACGCCCGGCGT CTA ACT TTC CTT TCC GCC TCCCCAGCGT CTA ACT TTC CTT TCC GCC GGC GGA AAG GAA AGT TAG | Beacon Probe/target Hybrid | 39 18 | 64% 50% | no yes | no | no no | no yes | no no |
| L-01-29 | -10 Chlamydia pneumoniae -50 -100 | TCCACCCGGCGT CTC TTC CTC AAC CGA AAG TCGCCCAGTGAA CTC TTC CTC AAC CGA AAG CTT TCG GTT GAG GAA GAG | Beacon Probe/target Hybrid | 41 18 | 61% 50% | no yes | no | yes no | no yes | no no |
| L-01-30 | -10 "Chlamydia psittaci" group -50 -100 | TCAGCCCGGCGT AAG GCA AAA CCA ACT CCC TCGCCCAGCTGA AAG GCA AAA CCA ACT CCC GGG AGT TGG TTT TGC CTT | Beacon Probe/target Hybrid | 41 18 | 61% 50% | no yes | no | yes no | no yes | no no |
| L-01-31 | -10 Subgroup of the Parachlamydiaceae -50 -100 | CCGCCCGGCGT TCC GTT TTC TCC GCC TAC TCGCCCAGCGG TCC GTT TTC TCC GCC TAC GTA GGC GGA GAA AAC GGA | Beacon Probe/target Hybrid | 39 18 | 69% 50% | no yes | no | no no | no yes | no no |
| L-01-32 | -10 Chlamydia ssp. -50 -100 | TCCGCCCGGCGT GCT CCC CTT GCT TTC GCG TCGCCCAGCGGA GCT CCC CTT GCT TTC GCG CGC GAA AGC AAG GGG AGC | Beacon Probe/target Hybrid | 42 18 | 69% 61% | no no | no | no no | no yes | no no |
| L-01-33 | -10 Chlamydia trachomatis -50 -100 | ACGCTC TCG GAT GCC CAA ATA TCG GAGCGT TCG GAT GCC CAA ATA TCG CGA TAT TTG GGC ATC CGA | Beacon Probe/target Hybrid | 30 18 | 57% 50% | yes yes | no | no no | no yes | no no |
| L-01-34 | -10 Canda albicans -50 -100 | GG aa tgg cta ccc aga agg aaa CCATTCC aa tgg cta ccc aga agg aaa ttt cct tct ggg tag cca tt | Beacon Probe/target Hybrid | 29 20 | 52% 45% | yes yes | no | yes yes | no no | no no |

TABLE 2-continued

| Loop Diagnostics Code number | Target organism | Sequence 5'-3' | | Length | GC content | PNA-suitable? | | | | Final |
|---|---|---|---|---|---|---|---|---|---|---|
| | | | | | | on GC content | on <3-base self complem. | on 4 purins in a row | length inverse seq., (max palindromes/18) repeats/hairpin | |
| L-01-35 | -10 Canda krusei | CCGCTC tgt att agc tct aga ttt cca cgg GAGCGG | Beacon | 36 | 19 53% | yes | no | yes | no | no |
| | -50 | tgt att agc tct aga ttt cca cgg | Probe/target Hybrid | 24 | 9 38% | yes | | no | no | no |
| | -100 | ccg tgg aaa tct aga gct aat aca | | | | | | | | |
| L-01-36 | -10 Candida dubliniensis | GTTTGcc ccg aaa gag taa ctt gca GGCAAAC | Beacon | 32 | 16 50% | yes | no | no | no | no |
| | -50 | cc ccg aaa gag taa ctt gca | Probe/target Hybrid | 20 | 10 50% | yes | | no | no | no |
| | -100 | tgc aag tta ctc ttt cgg gg | | | | | | | | |
| L-01-37 | -10 Candida glabrata | GCCGCCGGCGT gg cca ccc agg ccc aaa TCGCCCAGCGGC | Beacon | 40 | 32 80% | no | no | no | no | no |
| | -50 | gg cca ccc agg ccc aaa | Probe/target Hybrid | 17 | 12 71% | no | | no | yes | yes |
| | -100 | ttt ggg cct ggg tgg cc | | | | | | | | |
| L-01-38 | -10 Candida Parapsilosis | GCCGCCGGCGT gc caa aaa ggc tag cca gaa TCGCCCAGCGGC | Beacon | 43 | 30 70% | no | no | no | no | no |
| | -50 | gc caa aaa ggc tag cca gaa | Probe/target Hybrid | 20 | 10 50% | yes | | no | no | no |
| | -100 | ttc tgg cta gcc ttt ttg gc | | | | | | | | |
| L-01-39 | -10 Candida spp | ACGC gct tgg ctg gcc ggt c GCGT g acc ggc cag cca agc gct tgg ctg gcc ggt c | Beacon Probe/target Hybrid | 16 24 | 12 75% 18 75% | no no | no | no no | yes no | no no |
| L-01-40 | -10 Candida tropicales | ACCGCCGGCGT tac gca tca gaa aga tgg acc TCGCCCAGCGGT | Beacon | 44 | 28 64% | no | | yes | no | no |
| | -50 | tac gca tca gaa aga tgg acc | Probe/target Hybrid | 21 | 10 48% | yes | | no | no | no |
| | -100 | GGT TCA TCT TTC TGA TGC GTA | | | | | | | | |
| L-01-41 | -10 Candida lusitaniae | | Beacon Probe/target Hybrid | | | | | | | |
| | -50 | | | | | | | | | |
| | -100 | | | | | | | | | |
| L-01-42 | -10 Citrobacter freundii | TGCCGGATT C TAC TTG TTA GGT GAC TGC GT AATCCCGGCA | Beacon | 40 | | yes | no | yes | no | no |
| | -50 | C TAC TTG TTA GGT GAC TGC GT | Probe/target Hybrid | 21 | 11 48% | yes | | no | no | no |
| | -100 | AC GCA GTC ACC TAA CAA GTA G | | | | | | | | |
| L-01-43 | -10 Clostridium botulinum | TCTTG TAG T GC CGT TTC ATG CGA AAC TAC AA GA | Beacon | 33 | | yes | no | no | no | no |
| | -50 | GC CGT TTC ATG CGA AAC TAC AA | Probe/target Hybrid | 22 | 10 45% | yes | | no | no | no |
| | -100 | TT GTA GTT TCG CAT GAA ACG GC | | | | | | | | |

TABLE 2-continued

| Loop Diagnostics Code number | Target organism | Sequence 5'-3' | | Length | GC content | PNA-suitable? | | | | Final |
|---|---|---|---|---|---|---|---|---|---|---|
| | | | | | | on GC content | on <3-base self complem. | on 4 purins in a row | length inverse seq., (max palindromes/18) repeats/hairpin | |
| L-01-44 | -10 Clostridium difficile -50 -100 | GCCGCCGGCGT CGAAG TAA ATC GCT CAA CTT GCA TCGCCCAGCGGC CGA AGT AAA TCG CTC AAC TTG CA TGC AAG TTG AGC GAT TTA CTT CG | Beacon | 46 | 65% | no | no | yes | no | no |
| | | | Probe/target Hybrid | 23 | 43% | yes | no | no | no | no |
| L-01-45 | -10 Clostridium spp -50 -100 | CGCTCA CAC CCG TCC GCC GCT AAT GAGCG CAC CCG TCC GCC GCT AAT ATT AGC GGC GGA CGG GTG | Beacon | 29 | 69% | no | no | no | no | no |
| | | | Probe/target Hybrid | 18 | 67% | no | no | no | yes | no |
| L-01-46 | -10 Clostridium perfringens -50 -100 | GCCGCCGGCGT G ATT GCT CCT TTG GTT GAA TGA TG TCGCCCAGCGGC G ATT GCT CCT TTG GTT GAA TGA TG CA TCA TTC AAC CAA AGG AGC AAT C | Beacon | 44 | 68% | no | no | no | no | no |
| | | | Probe/target Hybrid | 21 | 48% | yes | no | no | no | no |
| L-01-47 | -10 Clostridium perfringens -50 -100 | ACGCTC GGT TGA ATG ATG ATG CCA T GAGCGT GGT TGA ATG ATG ATG ATG CCA TCT TT AA AGA TGG CAT CAT CAT CAT TCA ACC | Beacon | 31 | 52% | yes | no | yes | no | no |
| | | | Probe/target Hybrid | 19 | 42% | yes | no | yes | no | no |
| L-01-48 | -10 Clostridium tetani -50 -100 | GCGGAC CT GTG TTA CTC ACC CGT CCG C CT GTG TTA CTC ACC CGT CCG CGG ACG GGT GAG TAA CAC AG | Beacon | 27 | 52% | yes | no | no | no | no |
| | | | Probe/target Hybrid | 20 | 42% | yes | no | no | no | no |
| L-01-49 | -10 Cryptococcus neoformans -50 -100 | | Beacon Probe/target Hybrid | | | | | | | |
| L-01-50 | -10 Enterobacteriaceae -50 -100 | TGCCGGATT TT CGT GTT TGC ACA GTG CTG T AATCCCGGCA TT CGT GTT TGC ACA GTG CTG T A CAG CAC TGT GCA AAC ACG AA | Beacon | 40 | 53% | yes | no | yes | no | no |
| | | | Probe/target Hybrid | 21 | 48% | yes | no | no | no | no |
| L-01-51 | -10 Enterobacteriaceae -50 -100 | TGCCGGATT TCT CGC GAG GTC GCT TCT AATCCCGGCA TCT CGC GAG GTC GCT TCT AGA AGC GAC CTC GCG AGA | Beacon | 27 | 59% | yes | no | no | no | no |
| | | | Probe/target Hybrid | 18 | 61% | no | no | no | yes | no |
| L-01-52 | -10 Enterobacteriaceae -50 -100 | TGCCGGATT CCC CCW CTT TGG TCT TGC GA AATCCCGGCA CCC CCW CTT TGG TCT TGC GA TC GCA AGA CCA AAG WGG GGG | Beacon | 39 | 59% | yes | no | no | no | no |
| | | | Probe/target Hybrid | 20 | 60% | no | no | no | no | no |

TABLE 2-continued

| Loop Diagnostics Code number | Target organism | Sequence 5'-3' | | Length | GC content | on GC content | PNA-suitable? on <3-base self complem. | on 4 purins in a row | length inverse seq., (max palindromes/ 18) repeats/ hairpin | Final |
|---|---|---|---|---|---|---|---|---|---|---|
| L-01-53 | -10 Enterococci | TGCCGGATT ATC CAT CAG CGA CAC CCG AATCCCGGCA | Beacon | 38 | 58% | yes | no | no | no | no |
| -50 | | ATC CAT CAG CGA CAC CCG | Probe/target Hybrid | 18 | 61% | no | | no | yes | no |
| -100 | | CGG GTG TCG CTG ATG GAT | | | | | | | | |
| L-01-54 | -10 Enterococcus faecalis | TGCCGGATT CCC TCT GAT GGG TAG GTT AATCCCGGCA | Beacon | 37 | 57% | yes | no | yes | no | no |
| -50 | | CCC TCT GAT GGG TAG GTT | Probe/target Hybrid | 18 | 56% | yes | no | no | yes | no |
| -100 | | AAC CTA CCC ATC AGA GGG | | | | | | | | |
| L-01-55 | -10 Enterococcus faecium | GCCGCGGCGT TTC AAA TCA AAA CCA TGC GGT TTC TCGCCCAGCCGC | Beacon | 47 | 62% | no | no | no | no | no |
| -50 | | TTC AAA TCA AAA CCA TGC GGT TTC | Probe/target Hybrid | 24 | 38% | yes | no | no | no | no |
| -100 | | GAA ACC GCA TGG TTT TGA TTT GAA | | | | | | | | |
| L-01-56 | -10 Escherichia coli | TGCCGGATT GGA AGA AGC TTG CTT CTT TGC AATCCCGGCA | Beacon | 40 | 53% | yes | no | yes | no | no |
| -50 | | GGA AGA AGC TTG CTT CTT TGC | Probe/target Hybrid | 21 | 48% | yes | no | no | no | no |
| -100 | | GCA AAG AAG GAA GCT TCT TCC | | | | | | | | |
| L-01-57 | -10 Eu-bacteria | CGCTC GCT GCC TCC CGT AGG AGT GAGCG | Beacon | 28 | 71% | no | no | no | no | no |
| -50 | | GCT GCC TCC CGT AGG AGT | Probe/target Hybrid | 18 | 67% | no | no | no | yes | no |
| -100 | | ACT CCT ACG GGA GGC AGC | | | | | | | | |
| L-01-58 | -10 Fusarium spp | | | | | | | | | |
| -50 | | | | | | | | | | |
| -100 | | | | | | | | | | |
| L-01-59 | -10 Gardnerella vaginalis | ACGCTC CAC CAT GAA GCA ACC CGT GAGCGT | Beacon | 30 | 60% | no | no | no | no | no |
| -50 | | CAC CAT GAA GCA ACC CGT | Probe/target Hybrid | 18 | 56% | yes | no | no | yes | no |
| -100 | | ACG GGT TGC TTC ATG GTG | | | | | | | | |
| L-01-60 | -10 Haemophilus influenzae | ACCCGCTA TT CCG ATA ATA CGC GGT ATT AGC GGGT | Beacon | 35 | 51% | yes | no | no | no | no |
| -50 | | TT CCG ATA ATA CGC GGT ATT AGC | Probe/target Hybrid | 23 | 43% | yes | no | no | no | no |
| -100 | | GCT AAT ACC GCG TAT TAT CGG AA | | | | | | | | |
| L-01-61 | -10 Haemophilus influenzae | CGGTGCTC TA ATA CGC GGT ATT AGC GAC AG AGAGCACCG | Beacon | 39 | 56% | yes | no | no | no | no |
| -50 | | TA ATA CGC GGT ATT AGC GAC AG | Probe/target Hybrid | 22 | 45% | yes | no | no | no | no |
| -100 | | CT GTC GCT AAT ACC GCG TAT AT | | | | | | | | |

TABLE 2-continued

| Loop Diagnostics Code number | Target organism | Sequence 5'-3' | | Length | GC content | PNA-suitable? on GC content | on <3- base self complem. | on 4 purins in a row | length inverse seq., (max palindromes/ 18) repeats/ hairpin | Final |
|---|---|---|---|---|---|---|---|---|---|---|
| L-01-62 | -10 Klebsiella pneumoniae -50 -100 | ACGCCGGCGT AGG TTA TTA ACC TCA TCG CCT TCGCCCAGCGT AGG TTA TTA ACC TCA TCG CCT AGG CGA TGA GGT TAA TAA CCT | Beacon Probe/target Hybrid | 40 21 | 63% 9 43% | yes | no | no | no | no no |
| L-01-63 | -10 Klebsiella oxytoca -50 -100 | GGAAGGATAT AGG TTA TTA ACC TCA CTC CCT TCC AGG TTA TTA ACC TCA CTC CCT TCC GGA AGG GAG TGA GGT TAA TAA CCT | Beacon Probe/target Hybrid | 35 24 | 16 46% 111 46% | yes yes | no | yes yes | no | no no |
| L-01-64 | -10 Lactobacillus brevis -50 -100 | CGC TCAT TCA ACG GAA GCT CGT TCG ATGAGCG TCAT TCA ACG GAA GCT CGT TCG CGAAC GAGCTTCCGT TGAATGA | Beacon Probe/target Hybrid | 31 22 | 48% 11 50% | yes yes | no | yes yes | no | no no |
| L-01-65 | -10 Mycobacterium avium -50 -100 | | Beacon Probe/target Hybrid | | | | | | | |
| L-01-66 | -10 Mycobacterium bovis -50 -100 | | | | | | | | | |
| L-01-67 | -10 Mycobacterium chelonae -50 -100 | | | | | | | | | |
| L-01-68 | -10 Mycobacterium fortuitum -50 -100 | | | | | | | | | |
| L-01-69 | -10 Mycobacterium gordonae -50 -100 | | | | | | | | | |
| L-01-70 | -10 Mycobacterium intracellulare -50 -100 | | | | | | | | | |
| L-01-71 | -10 Mycobacterium kansasii -50 -100 | | | | | | | | | |

TABLE 2-continued

| Loop Diagnostics Code number | Target organism | Sequence 5'-3' | | Length | GC content | PNA-suitable? on GC content | on <3-base self complem. | on 4 purins in a row | length inverse seq., (max palindromes/ 18) repeats/ hairpin | Final |
|---|---|---|---|---|---|---|---|---|---|---|
| L-01-72 | -10 Mycobacterium<br>-50 malmoense<br>-100 | | | | | | | | | |
| L-01-73 | -10 Mycobacterium<br>-50 smegmatis<br>-100 | | | | | | | | | |
| L-01-74 | -10 Mycobacterium<br>-50 tuberculosis<br>-100 | | | | | | | | | |
| L-01-75 | -10 Mycobacterium<br>-50 xenopi<br>-100 | | | | | | | | | |
| L-01-76 | -10 Legionella<br>pneumophila | TGCCGGATT ATC TGA CCG TCC CAG<br>GTT AATCCCGGCA | Beacon | 37 | 57% | yes | no | yes | no | no |
| | -50<br>-100 | ATC TGA CCG TCC CAG GTT<br>AAC CTG GGA CGG TCA GAT | Probe/target Hybrid | 18 | 10 56% | yes | | no | yes | |
| L-01-77 | -10 Listeria<br>monocytogenes | ACGCTC ATA AGA TGT GGC GCA TGC<br>GAGCGT | Beacon | 30 | 57% | yes | no | no | no | no |
| | -50<br>-100 | ATA AGA TGT GGC GCA TGC<br>GCA TGC GCC ACA TCT TAT | Probe/target Hybrid | 18 | 9 50% | yes | | no | yes | |
| L-01-78 | -10 Mycoplasma<br>-50 hominis<br>-100 | TBD<br>ATT GCT AAC CTC GCT CGA<br>TCG AGC GAG GTT AGC AAT | Beacon<br>Probe/target Hybrid | | | | | | | |
| L-01-79 | Nocardia spp. | | Beacon<br>Probe/target Hybrid | | | | | | | |
| L-01-80 | -10 Proteus<br>mirabili/vulgaris | GGC GTC ACA CCG G AT ACG<br>TAGTGCTACGCC | Beacon | 30 | 63% | no | no | no | no | no |
| | -50<br>-100 | GGC GTC ACA CCG G AT ACG<br>CCGT ATC CGG TGT GAC GCC | Probe/target Hybrid | 18 | 12 67% | yes | | no | yes | |
| L-01-81 | -10 Pneumocystis-1 | ACTC GGC TTC ATG CCA ACA GTC<br>GAGT | Beacon | 25 | 56% | yes | no | yes | no | no |
| | -50<br>-100 | GGC TTC ATG CCA ACA GTC<br>GAC TGT TGG CAT GAA GCC | Probe/target Hybrid | 21 | 10 57% | yes | | yes | yes | |

TABLE 2-continued

| Loop Diagnostics Code number | Target organism | Sequence 5'-3' | | Length | GC content | PNA-suitable? | | | | Final |
|---|---|---|---|---|---|---|---|---|---|---|
| | | | | | | on GC content | on <3-base self complem. | on 4 purins in a row | length inverse seq., (max palindromes/18) repeats/hairpin | |
| L-01-82 -10 -50 -100 | Pneumocystis-2 | GACAC CAT AAG ATG CCG AGC GAG GTGTC<br>CAT AAG ATG CCG AGC GAG CTC GCT CGG CAT CTT ATG | Beacon<br>Probe/target Hybrid | 28<br>18 | 57%<br>56% | yes<br>yes | no<br>no | no<br>no | no<br>yes | no<br>no |
| L-01-83 | Propionibacterium acnes | | | | | | | | | |
| L-01-84 | Propionibacterium spp (other than Psaer) | | | | | | | | | |
| L-01-85 -10 -50 -100 | Pseudomonas aeruginosa | ACCGCCGGCGT A AGA CGA CTC GTC ATC ACC T TCGCCCAGCGGT<br>A AGA CGA CTC GTC ATC ACC T<br>A GGT GAT GAC GAGTCG TCT T | Beacon<br>Probe/target Hybrid | 42<br>20<br>10 | 67%<br>50% | no<br>yes | no<br>no | yes<br>no | no<br>no | no<br>no |
| L-01-86 -10 -50 -100 | Pseudomonas spp | GCCGCCGGCGT GGC AGA TTC CTA GGC ATT ACT TCGCCCAGCGGC<br>GGC AGA TTC CTA GGC ATT ACT AGT AAT GCC TAG GAA TCT GCC | Beacon<br>Probe/target Hybrid | 44<br>30<br>21<br>10 | 68%<br>48% | no<br>yes | no<br>no | yes<br>no | no<br>no | no<br>no |
| L-01-87 -10 -50 -100 | Salmonellen | AGCTC TGC GCT TTT GTG TAC GGG GCT GAGCT<br>TGC GCT TTT GTG TAC GGG GCT AGC CCC GTA CAC AAA AGC GCA | Beacon<br>Probe/target Hybrid | 31<br>21<br>11 | 58%<br>57% | yes<br>yes | no | no<br>no | no<br>no | no<br>no |
| L-01-88 -10 -50 -100 | Salmonellen 331 Komp | not required, competitor is not labelled<br>G TGCA TTT GTG TAC GGG GC AGC CCC GTA CAC AAA AGC GCA | Beacon<br>Probe/target Hybrid | 18<br>11 | 61% | no<br>yes | no | no<br>no | yes<br>no | no<br>no |
| L-01-89 -10 -50 -100 | Salmonellen | CGCTC CTT CAC CTA CGT GTC AGC G GAGCG<br>CTT CAC CTA CGT GTC AGC G C GCT GAC ACG TAG GTG AAG | Beacon<br>Probe/target Hybrid | 29<br>19<br>11 | 66%<br>58% | no<br>yes | no<br>no | yes<br>no | no<br>no | no<br>no |
| L-01-90 -10 -50 -100 | Salmonellen | not required, competitor is not labelled<br>T CAC CTA CAT ATC AGC GTG C C GCT GAC ACG TAG GTG AAG A | Beacon<br>Probe/target Hybrid | 20<br>10 | 50% | yes | no | yes | no | no |

TABLE 2-continued

| Loop Diagnostics Code number | Target organism | Sequence 5'-3' | | Length | GC content | on GC content | on <3-base self complem. | on 4 purins in a row | length inverse seq., (max palindromes/ 18) repeats/ hairpin | Final |
|---|---|---|---|---|---|---|---|---|---|---|
| L-01-91 | -10 Salmonellen -50 -100 | | Beacon Probe/target Hybrid | | | | | | | |
| L-01-92 | -10 Salmonella -50 -100 | TGCCGGATT CTT CAC CTA CGT GTC AGC G AATCCCGGCA CTT CAC CTA CGT GTC AGC G C GCT GAC ACG TAG GTG AAG | Beacon Probe/target Hybrid | 38 19 | 58% 58% | yes yes | no | yes no | no no | no no |
| L-01-93 | -10 Serratia spp -50 -100 | | Beacon Probe/target Hybrid | | | | | | | |
| L-01-94 | -10 Serratia marcesceris -50 -100 | GCCGCCGGCGT CG AGA CTC TAG CTT GCC AGT TCGCCCAGCGGC CG AGA CTC TAG CTT GCC AGT ACT GGC AAG CTA GAG TCT CG | Beacon Probe/target Hybrid | 43 20 | 72% 55% | no yes | no | yes no | no no | no no |
| L-01-95 | -10 Staphylococcus aureus -50 -100 | TGCCGGATT TTC TCG TCC GTT CGC TCG ACT TGC AATCCCGGCA TTC TCG TCC GTT CGC TCG ACT TGC GCA AGT CGA AGT CGA AAC GGA CGA GAA | Beacon Probe/target Hybrid | 43 24 | 158% 58% | yes yes | no | yes no | no no | no no |
| L-01-96 | -10 Staphylococci -50 -100 | GCAAC TT TCG CAC ATC AGC GTC AGT T GC TT TCG CAC ATC AGC GTC AGT T A ACT GAC GCT GAT GTG CGA AA | Beacon Probe/target Hybrid | 281 21 | 54% 48% | yes yes | no | yes yes | no no | no no |
| L-01-97 | -10 Stenotrophomonas maltofilia -50 -100 | CCC TCT ACC ACA CTC TAG TCG GGT AGA GGG CCC TCT ACC ACA CTC TAG TCG CGA CTA GAG TGT GGT AGA GGG | Beacon Probe/target Hybrid | 30 21 | 57% 52% | yes yes | no | no no | no no | no no |
| L-01-98 | -10 Streptococcus agalactiae -50 -100 | GCCGCCGGCGT ACT CCT ACC AAC GTT CTT CTC TCGCCCAGCGGC ACT CCT ACC GTT CTT CTC GAG AAG AAC GTT GGT AGG AGT | Beacon Probe/target Hybrid | 45 21 | 67% 48% | no yes | no | yes no | no no | no no |
| L-01-99 | -10 Streptococci -50 -100 | GGCCTTC GCC GTC CCT TTC TGG TTA GTT GAAGGCC GCC GTC CCT TTC TGG TTA GTT AAC TAA CCA GAA AGG GAC GGC | Beacon Probe/target Hybrid | 35 21 | 60% 52% | no yes | no | no no | no no | no no |

TABLE 2-continued

| Loop Diagnostics Code number | Target organism | Sequence 5'-3' | | Length | GC content | on GC content | PNA-suitable? on <3- base self complem. | on 4 purins in a row | length inverse seq., (max palindromes/ 18) repeats/ hairpin | Final |
|---|---|---|---|---|---|---|---|---|---|---|
| L-01-100 | -10 Streptococcus pneumoniae | GCGT TAA GCA AAT GTC ATG CAA CAT CTA CTTAACGC | Beacon | 38 | 39% | yes | no | yes | no | no |
| -50 -100 | | T TAA GCA AAT GTC ATG CAA CAT CTA TAG ATG TTG CAT GAC ATT TGC TTA A | Probe/target Hybrid | 25 | 32% | yes | | yes | no | no |
| L-01-101 | -10 Streptococcus pyogenes | TGCCTTC GAG CAA TTG CCC CTT TTA AAT TAC GAAGGCA | Beacon | 38 | 45% | yes | no | no | no | no |
| -50 -100 | | GAG CAA TTG CCC CTT TTA AAT TAC GTA ATT TAA AAG GGG CAA TTG CTC | Probe/target Hybrid | 24 | 38% | yes | | no | no | no |
| L-01-102 | -10 Ureaplasma urealyticum | ACGCTC GTT CCC CAA CTC CCT ACT GAGCGT | Beacon | 30 | 60% | no | no | no | no | no |
| -50 -100 | | GTT CCC CAA CTC CCT ACT AGT AGG GAG TTG GGG AAC | Probe/target Hybrid | 18 | 56% | yes | | no | yes | no |
| L-01-103 | -10 Urogenital-Peptostreptococci | ACTC CCC CTT GTG TM GGC AGG GAGT | Beacon | 28 | 54% | yes | no | no | no | no |
| -50 -100 | | CCC CTT GTG TAA GGC AGG CCT GCC TTA CAC AAG GGG | Probe/target Hybrid | 24 | 54% | yes | | no | no | no |
| L-01-104 | -10 Yersinia enterocolitica | ACGCTC CCC ACT TTG GTC CGA AGA GAGCGT | Beacon | 30 | 60% | no | no | yes | no | no |
| -50 -100 | | CCC ACT TTG GTC CGA AGA TCT TCG GAC CAA AGT GGG | Probe/target Hybrid | 18 | 56% | yes | | no | yes | no |

TABLE 3

List of Beacon probes that work under identical conditions as in
Table 1 and possess very similar physicochemical conditions

| Target organism | Beacon name | Sequence 5'-3' |
|---|---|---|
| Acinetobacter spp. | B-Acibact-1 | TGCCGGTT TTAGGCCAGATGGCTGCC AATCCCGGCA |
| Aspergillus fumigatus, | Aspfum | CCGG CCC CCG AGA GGT GAT ACA T GCCGG |
| Aspergillus niger, | Aspnig | CCGGC AAT TAC AAT GCG GAC TCC GAA G CCGG |
| Klebsiella pneumoniae, | B;Klepne-2 | ACGCCGGCGT AGG TTA TTA ACC TCA TCG CCT TCGCCCAGCGT |
| Mycobacterium avium Complex, | B.Mycav | CCC GGT GTT GAT ATA AGG CAG GTG CCGGG |
| Mycobacterium chelonae, | B-Mchel | CCCGG CA TGA AGT GTG TGG TCC TAT CCGGG |
| Mycobacterium fortuitum, | B-Mfort | CCCGG TGA AGC GCG TGG TCA TAT TC CCGGG |
| Mycobacterium gordonae, | B-Mgord | CCCGG TGT GTC CTG TGG TCC TAT TC CCGGG |
| Mycobacterium intracellulare, | B-Mintra | CCCGG AC ATG CGT CTA AAG GTC CTA CCGGG |
| Mycobacterium kansasii/gastri, | B-Mkan | CCCGG TA GAG CTG AGA CGT ATC GAT C CGGG |
| Mycobacterium malmoense, | B-Mmalm | CCG CG CCA CTG AAA CGC CCT ATT CGCGG |
| Mycobacterium smegmatis, | B-Msmeg | CCCGG CAC GTC GAG GGC TCT GAC CCGGG |
| Mycobacterium tuberculosis complex, | B-Mtb-compl | CCA CCG GAG AGG AAA AGG AGG TGG |
| Mycobacterium xenopi, | B-Mxen | CCGCG C CGC TAC CAA ACG CTT TC GCGG |
| Shigella (some E. coli), | B-Shig | CCGGG tca ccc tgt atc gca cac ct CCCGG |
| Staphylococcus aureus, | B-Staphau | TGCCGGATT TTC TCG TCC GTT CGC TCG ACT TGC AATCCCGGCA |
| Streptococcus agalactiae, | B-Straga-2 | GCCGCGGCGT ACT CCT ACC AAC GTT CTT CTC TCGCCCAGCGGC |
| Streptococcus pyogenes, | B-Strpyo-C | TGCCTTC GAG CAA TTG CCC CTT TTA AAT TAC GAAGGCA |
| Citrobacter freundii, | Citfreu-WI | CCCGGT CGC TTC ATT ACG CTA TGT ATC C ACCGGG |
| Streptococcus pyogenes, | B-Strpyo-D | CGCTC GAG CAA TTG CCC CTT TTA AAT TAC GAGCG |
| Streptococcus pneumoniae, | B-Strepne-2 | CCGT TAA GCA AAT GTC ATG CAA CAT CTA CTTA ACGG |
| Streptococci, F111 | B-Strept-2 | CGCCTTC GCC GTC CCT TTC TGG TTA GTT GAAGGCG |

TABLE 3-continued

List of Beacon probes that work under identical conditions as in
Table 1 and possess very similar physicochemical conditions

| Target organism | Beacon name | Sequence 5'-3' |
|---|---|---|
| Streptococcus agalactiae, | B-Straga-3 | CCGCT ACT CCT ACC AAC GTT CTT CTC AGCGG |
| Serratia marcescens, | B-Sermarc | CCGCTC CG AGA CTC TAG CTT GCC AGT GAGCGG |
| Pseudomonas spp., | B-Psspp | CGCTC GGC AGA TTC CTA GGC ATT ACT GAGCG |
| Staphylococci, | B-Staphspp-2 | CCAAC TT TCG CAC ATC AGC GTC AGT T GG |
| Salmonella, | B-Sal 1686 | CGCTC CTT CAC CTA CGT GTC AGC G GAGCG |
| Pseudomonas aeruginosa, | B-Psaer D | CCCGG A AGA CGA CTC GTC ATC AGC T CCGGG |
| Legionella pneumophila, | B-Legpne | CC GG ATC TGA CCG TCC CAG GTT CC GG |
| Klebsiella oxytoca, | B-Kleboxy | CCGAGGT AGG TTA TTA ACC TCA CTC CCT TCC TCGG |
| Staphylococcus aureus, | B-Staur-W1 | CCCCT CAA GCT TCT CGT CCG TTC G A GGGG |
| Listeria monocytogenes, | Lismon | CCTA GCA TGC GCC ACA TCT TAT CA GCTAGG |
| Klebsiella pneumoniae, | B-Klepne-3 | CAGGCTT AGG TTA TTA ACC TCA TCG CCT G |
| Haemophilus influenzae, | B-Haeinf | CCCGG CC GCA CTT TCA TCT TCC GAT CCGGG |
| Burkholderia spp., | B-Burk. Spp | CCCGG CCA GTC ACC AAT GCA GTT CC CCGGG |
| Burkholderia cepatia & Burkholderia cenocepatia, | B-Burcep-cen WI | CCT GCC TA TGT ATT CAG CCA TGG CAGG |
| Burkholderia malii & Burkholderia pseudomalei, | B-Burpseumal WI | GGGCC T CGC CTC ACT AGA CCT ATG CCGGG |
| Burkholderia vietnamensis, | B-Burviet WI | CCCGG T CGC TTC TCT GGA CCT ATG CCGGG |
| Burkholderia multivorans, | B-Burmult WI | CCCGG CTT CAC CCT TCC AGC GCA CCGGG |
| Burkholderia gladioli, | B-Burgla WI | CCAGC GG TAC GGT CAC TGT TAA ACT GCTGG |
| Acinetobacter spp, | B-Acibact-2 | CCGTAG ACC ATC CTC TCC CAT ACT CTA CGG |
| Acinetobacter baumanii, | B-Acinbaum-3 | C CG CTA GGT CCG GTA GCA AGC GG |
| Aspergillus flavus, | B-Aspfla-3 | CGGCC TAC ATT CCG GGA GCC TTT G GCCG |
| Aspergillus terreus, | Aspter | CCGAT CAG ACA CCC CGC CCC ATA GATCGG |
| Bacteroides/Prevotella, | B-BacPrev | CCGCG GT GTC TCA GTT CCA ATG TGG G CGCGG |
| Borrelia burgdorferi + garinii + afzelii + valaisiana, | B-Borrcompl | CCCGG GGT AAC AGA TAA CAA GGG TTG CCCGGG |

TABLE 3-continued

List of Beacon probes that work under identical conditions as in
Table 1 and possess very similar physicochemical conditions

| Target organism | Beacon name | Sequence 5'-3' |
|---|---|---|
| Bordetella pertussis, | B-Borper | CCGGG CTC CCC ACA CTT TCG TGC A CCCGG |
| Escherichia coli, | B-Ecol-II | CCG GCA AAG AAG CAA GCT TCT TCC CCGG |
| Gardnerella vaginalis, | Garvag | CCGCTC CAC CAT GAA GCA ACC CGT GAGCGG |
| Eu-bacteria, | B-Eub-338 | CCGCGT GCT GCC TCC CGT AGG AGT CGCGG |
| Enterococcus faecium, | B-Encoc-ium | C TTC AAA TCA AAA CCA TGC GGT TTC ATTTGAAG |
| Stenotrophomonas maltophilia, | B-Stemal-2 | CCCGGA CCC TCT ACC ACA CTC TAG TCG CCGGG |
| Enterococcus faecalis, | B-Encoc-alis-1 | CAACCA CCC TCT GAT GGG TAG GTT G |
| Enterococci, | B-Entcoc | CCCGG C ATC CAT CAG CGA CAC CCG CCG GG |
| Enterobacteriaceae, | B-Entero-1247 | CCCGG TCT CGC GAG GTC GCT TCT CCGGG |
| Clostridium perfringens, | B-Cloper-Cp2-10 | GCATCA G ATT GCT CCT TTG GTT GAA TGA TG C |
| Clostridium spp., | B-Clospp | CCC GG TAC CGT CAT TAT CGT CCC CCGGG |
| Chlamydia trachomatis, | ChltraA | CCGC TCG GAT GCC CAA ATA TCGC GG |
| Candida dubliniensis, | B-Can-dub | CCCGG C CCG AAA GAG TAA CTT GCA AAA CCCGG |
| Candida glabrata, | B-Cangla | CCCGG AGG CAA GGG GCG CAA AA CCGGG |
| Candida krusei, (Issatchenkia orientalis) | B-Cankru | CCGTGA CCT GCA GCA AGA ACC GAT CACGG |
| Candida lusitaniae, (Clavispora lusitaniae) | B. Canlus | CACT G CCG ACT CAG ACC ACG AAA GCAGTG |
| Candida albicans, | B-Canalb-3 | CCGCG TT TAC ACA GAC CCG GGT CAT CGCGG |
| Candida tropicalis, | B-Cantrop | CCTCGG AC ATT CCA ACG CAA TTC TCCTAC CGAGG |
| Candida parapsilosis, | B-Can-para | CCCGG CAC ATT TCT TTG CAC TTA TCC TAC CCGGG |
| Chlamydia pneumoniae, | B-Chlapneu | CCGGG CTC TTC CTC AAC CGA AAG GT CCCGG |
| Chlamydia psittaci group, | B-S-S-Cps-1414-a-A-18 | CCGG AAG GCA AAA CCA ACT CCC AT CCGG |
| Campylobacter (pathogenic thermophiles), | B-Ctherm | CCCGG GCC CTA AGC GTC CTT CCA CCGGG |
| Campylobacter coli, | B-Cpcoli | CGCTC TCG ATG GCA TCA GGG GTT GAGCG |
| Campylobacter lari, | Clari | CCCGG CCC GAA GTG TTA GCA ACT AAA TC GCCGGG |
| Campylobacter jejuni, | B-Cjj | CCGGG TA AGC TAA CCA CAC CTT ATA CCG CCCGG |

TABLE 3-continued

List of Beacon probes that work under identical conditions as in Table 1 and possess very similar physicochemical conditions

| Target organism | Beacon name | Sequence 5'-3' |
| --- | --- | --- |
| Campylobacter upsaliensis, | B-Cpups | CCCGGGC CGT GTG TCG CCC TAG GCG TA GCCCGGG |
| Pneumocystis carinii, | B-Pncari | CCCTGC TA TCC AGT AAC TGA AAC CGA TGC AGGG |
| Mycoplasma pneumoniae, | B-Myplapn | CCTCCG TGA TAG CTG TTT CCA ACT ACC GGA GG |
| Cryptococcus neoformans, | B-Cryneo | CCTGG TAT GAT TCA CCA TAG AGG GCC AGG |
| EHEC, | B-EHEC | CCCG GT CAC CCC ATA AAA GAG GCT CCGGG |
| Neisseria meningitidis, | B-Neimeng | CACCG TTA TCC CCC ACT ACT CGG TG |
| Neisseria gonorrhoeae, | B-Neigon | CCCGG ACC CCG CCA ACC AGC TAA CCGGG |
| Clostridium difficile, | B-Clodiff | CGGGT CGA AGT AAA TCG CTC AAC TTG CA CCCG |
| Clostridium botulinum, | B-Clobot | CG TT GC CGT TTC ATG CGA AAC TAC AA CG |
| Clostridium tetani, | B-Clotet | CCGG AA CT GTG TTA CTC ACC CGT CCG G |
| Peptostreptococcus anaerobius, | B-Pepan | CCGGC CTT TGA TAT ATC TAC GAT GCC G G |
| Peptostreptococcus magnus, | B-pepmag | CCGC CTA ATC CGA AAT GAA TTC TGG CG G |
| Peptostreptococcus magnus, | B-pepmag | CCGCC ATG TGT TTC TAC GAT TTT ATG CGG CGG |
| Peptostreptococcus micros, | B-Pepmic | CCCGG ACT TTC ATT TCA TTT CCA TTC CCG GG |
| Enterococcus faecalis, | B-Encoc-alis-2 | CCATCG GCA CTC GGG AGG AAA GAA G CGATGG |
| Enterococcus faecium, | B-entfae-1 | CGC CCA TGC GGT TTT GAT TGT TAT AC GGGCG |
| Enterococcus casseliflavus, | B-Entcas | CCGCG CAA GGG ACG AAC ATT TTA CTC TC GCGG |
| Enterococcus gallinarum, | B-entfae-2 | CCGCG CAA GGG ATG AAC GTT CTA CTC GCGG |
| Candida albicans, | B-Canalb-2 | CCCGG TTT CCT TCT GGG TAG CCA TT CCGGG |
| Morganella morganii (Proteus morganii), | B. Mormorg | CCGG CAA GAC TCT AGC TGA CCA GTA TC GCCGG |
| Proteus mirabilis, | B-Protmir | CG CCGATA GTG CAA GGT CCG AAG CGGCG |
| Proteus vulgaris, | B-Protvul | CCG CCG TAG ACG TCA TGC GGT A GGCGG |
| Treponema pallidum, | B-Trepal | CCCGG TCC GCC ACT CTA GAG AAA CG CCGGG |
| Trichonomas vaginalis, | B-Trivag | CCCGG GAA TGG CGT GCC TCT GAT GA CCGGG |

TABLE 3-continued

List of Beacon probes that work under identical conditions as in
Table 1 and possess very similar physicochemical conditions

| Target organism | Beacon name | Sequence 5'-3' |
|---|---|---|
| Micrococci, | B-Micoc | CCCGG ACC TCA CAG TAT CGC AAC C GGG |
| Lactobacillus brevis, | B-Lacbrev | CGG CCG CGG GAT CAT CCA GAA GGCCG |
| Yersinia enterocolitica, | B-Yerent | CCCGG ATC TCT GCT AAA TTC CGT GGA TG CCGGG |
| Bacillus cereus, | B-Baccer | CCATAC CAC TCT GCT CCC GAA GG TATGG |
| Vibrio cholerae, | B-Vibchol | CTGAT GCA TAT CCG GTA GCG CAA G CATCAG |
| Vibrio parahaemolyticus, | B-Vibpara | CCCGG TGC AGC TAT TAA CTA CAC TAC C CCGGG |
| Cryptosporidium spp., | B-Crypt | CCGTA CAT AAG GTG CTG AAG GAG TAA G TACGG |
| Coxiella burnetii, | B-Cox | CCGGG ACC CTT GAG AAT TTC TTC CCC GG |
| Bartonella spp., | B-Bart | CCG GCA CAA ATT TCT CTG TGT TAT TCC G CCGG |
| Enterobacter sakazakii, | B-Entsak | CCCGG TCT CTG CAG GAT TCT CTG GAT G CCGGG |
| Enterobacter cloacae, | B-Entclo | |
| Enterobacter aerogenes, | B-Entaer | |
| Ehrlichia spp., | B-Ehrlich | CCGC GCT AAT CTA ACG TAG GCT CAT C GCGG |
| Rickettsia spp., | B-Rickspp | CCGCG CAC TCA CTC GGT ATT GCT GGA T CGCGG |
| Rickettsia spotted fever complex, | B-Rickspot | CTA GCC CCA ATT AGT CCG TTC G GCTAG |
| Rickettsia typhi complex, | B-Ricktyph | CG CCC GTC TGC CAC TAA TTA ACT A GGGCG |
| Leishmania spp., | B-Leisch | CCCGG AAA AGG CGT TAC GGC CGG G |
| Toxoplasma gondii, | B-Toxgan | CCGGC TCC AGG GGA AGA GGC ATG CCGG |
| Yeast spp., | B-Yeast | CCCG GGT ATT TAC ATT GTA CTC ATT CCA A CCGGG |
| Francisella tularensis, | B-Frantul | CCAT GCG ACA GCC CGA AAG CCA GCATGG |
| Lactobacillus spp. A, | B-lactspp-A | CCC GGA GTT CCA CTG TCC TCT TC CCGGG |
| Lactobacillus spp. B, | B-lactspp-B | CCCGG ATC AGT CTC TCA ACT CGG C CGGG |
| Burkholderia cepacia complex | B-Bcc | CCC GGTTGGCAACCCTCTGTTCC CCGGG |
| Staphylococcus aureus, | B-Staur-3 | CCT G CAA GCT TCT CGT CCG TTC GC AGG |

TABLE 3-continued

List of Beacon probes that work under identical conditions as in Table 1 and possess very similar physicochemical conditions

| Target organism | Beacon name | Sequence 5'-3' |
|---|---|---|
| *Burkholderia ambifaria* | B-Burkamp | pending due to lack of 23S sequences |
| *Burkholderia antina* | B-Burkant | pending due to lack of 23S sequences |
| *Burkholderia dolosa* | B-Burkdol | pending due to lack of 23S sequences |
| *Burkholderia pyrrocinia* | B-Burkpyrr | pending due to lack of 23S sequences |
| *Burkholderia stabilis* | B-Burkstab | pending due to lack of 23S sequences |
| Lactobacilli, | | |
| *Candida* spp, | see Yeast | |
| Lactobacilli, | | |
| *Staphylococcus corosus*, | | |
| *Staphylococcus aureus*, | B-Staur | CCCCT CAA GCT TCT CGT CCG TTC G AGGGG |
| Eu-bacteria, | B-Eub-338 | CCGCGT GCT GCC TCC CGT AGG AGT CGCGG |
| Eu-bacteria, | B-Eub-338 | CCGCGT GCT GCC TCC CGT AGG AGT CGCGG |
| Eu-bacteria, | B-Eub-338 | CCGCGT GCT GCC TCC CGT AGG AGT CGCGG |
| Eu-bacteria, | B-Eub-338 | CCGCGT GCT GCC TCC CGT AGG AGT CGCGG |

---

The invention claimed is:

1. A nucleic acid capable of forming a hybrid with a target nucleic acid sequence and capable of forming a stem-loop structure if no hybrid is formed with the target sequence, said nucleic acid comprising
  (a) a nucleic acid portion comprising
    (a1) a sequence complementary to the target nucleic acid sequence, wherein the target nucleic acid sequence is a nucleic acid sequence of a microorganism,
    (a2) a pair of two complementary sequences capable of forming a stem,
  (b) an effector and an inhibitor, wherein the inhibitor inhibits the effector when the nucleic acid forms a stem-loop structure, and wherein the effector is active when the nucleic acid is not forming a stem-loop structure, and wherein the effector is a luminescent label, in particular a fluorescent label, and the inhibitor is a quencher, characterised in that the nucleic acid is constructed in a method comprising
  (i) designing the sequence of (a1) such that the ΔG of the hybrid of the sequence of (a1) with its target sequence is in the range of about −17 to about −25 kcal/mol under hybridisation conditions which comprise hybridisation in a buffer having a $Mg^{2+}$ concentration of less than 1 mM, and
  (ii) designing the sequences of (a2) such that the ΔG of the hybrid of the sequences of (a2) is smaller than 0 in the absence of the target sequence and higher than the ΔG of the hybrid of the sequence of (a1) with its target sequence.

2. The nucleic acid of claim 1, wherein the $T_m$ of the hybrid of the sequences of (a2) is essentially equal or lower than the $T_m$ of the hybrid of the sequence of (a1) with the target sequence.

3. The nucleic acid of claim 1, wherein the ΔG of the hybrid of the sequences of (a2) is lower than the ΔG of a hybrid of the nucleic acid with a mismatch sequence and/or a sequence different from the target sequence.

4. The nucleic acid of claim 1, wherein the stem formation takes place in the presence of about 1 to about 20 mM $Mg^{2+}$.

5. The nucleic acid of claim 1, wherein the nucleic acid portion (a) consists of ribonucleotides, ribonucleotide analogues, deoxyribonucleotides and/or deoxyribonucleotide analogues, which nucleotide analogues are different from PNA building blocks.

6. The nucleic acid of claim 1, wherein the nucleic acid portion (a) is selected from the beacon sequences of Table 1.

7. A combination comprising at least two nucleic acids as claimed in claim 1.

8. The combination of claim 7, wherein the ΔG values of the hybrid of the sequences of (a2) and/or the hybrid of the sequence of (a1) with a target sequence of the individual nucleic acids differ at the maximum by about 4 kcal/mol, or/and wherein the $T_m$ values of the hybrid of the sequences of (a2) or/and the hybrid of the sequence of (a1) with a target sequence of the individual nucleic acids differ at the maximum by about 3° C.

9. The combination of claim 7, wherein the individual nucleic acids function uniformly under hybridisation conditions required to hybridise under in-situ hybridisation conditions.

10. An in-situ hybridisation method comprising
  (a) contacting at least one nucleic acid of claim 1 with a biological sample,
  (b) hybridising the nucleic acid or the combination of nucleic acid of (a) with the sample in a buffer having a $Mg^{2+}$ concentration of less than 1 mM so that the stem of the nucleic is open, and (c) inducing conditions which allow for stem formation in those nucleic acid molecules of (a) not forming a hybrid with the sample, wherein the stem formation takes place in a buffer having a $Mg^{2+}$ concentration of about 1 to about 20 mM $Mg^{2+}$.

11. The method of claim 10, wherein stem formation takes place in a buffer having a $Mg^{2+}$ concentration of about 5 to about 10 mM $Mg^{2+}$.

12. The nucleic acid of claim 2, wherein the $T_m$ of the hybrid of the sequences of (a2) is at a maximum about 5° C., about 4° C., about 3° C., about 2° C., or about 1° C. lower than the $T_m$ of the hybrid of the sequence of (a1) with the target sequence.

13. The nucleic acid of claim 4, wherein the $T_m$ of the hybrid of the sequences of (a2) is at a maximum about 5° C., about 4° C., about 3° C., about 2° C., or about 1° C. lower than the $T_m$ of the hybrid of the sequence of (a1) with the target sequence in a buffer having a $Mg^{2+}$ concentration of less than 1 mM.

14. The nucleic acid of claim 4, wherein the stem formation takes place in the presence of about 5 to about 10 mM $Mg^{2+}$.

15. The nucleic acid of claim 14, wherein the stem formation takes place in the presence of about 8 to about 10 mM $Mg^{2+}$.

16. The method of claim 11, wherein stem formation takes place in a buffer having a $Mg^{2+}$ concentration of about 8 to about 10 mM $Mg^{2+}$.

* * * * *